(12) United States Patent
Selinfreund et al.

(10) Patent No.: US 8,501,669 B2
(45) Date of Patent: *Aug. 6, 2013

(54) SYSTEMS AND METHODS OF SCREENING BIOMARKERS IN BODILY FLUIDS

(75) Inventors: Richard H. Selinfreund, Terre Haute, IN (US); Rakesh Vig, Durham, CT (US); Richard P. Gill, Essex, CT (US)

(73) Assignee: Companion Diagnostics Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/906,159

(22) Filed: Oct. 18, 2010

(65) Prior Publication Data

US 2011/0195871 A1 Aug. 11, 2011

Related U.S. Application Data

(60) Provisional application No. 61/390,002, filed on Oct. 5, 2010, provisional application No. 61/385,347, filed on Sep. 22, 2010, provisional application No. 61/383,401, filed on Sep. 16, 2010, provisional application No. 61/379,598, filed on Sep. 2, 2010, provisional application No. 61/378,960, filed on Sep. 1, 2010, provisional application No. 61/373,619, filed on Aug. 13, 2010, provisional application No. 61/364,964, filed on Jul. 16, 2010, provisional application No. 61/364,969, filed on Jul. 16, 2010, provisional application No. 61/364,975, filed on Jul. 16, 2010, provisional application No. 61/364,978, filed on Jul. 16, 2010, provisional application No. 61/364,982, filed on Jul. 16, 2010, provisional application No. 61/365,179, filed on Jul. 16, 2010, provisional application No. 61/322,768, filed on Apr. 9, 2010, provisional application No. 61/303,165, filed on Feb. 10, 2010.

(51) Int. Cl.
*C40B 60/12* (2006.01)

(52) U.S. Cl.
USPC .................. 506/39; 506/40; 435/6.1; 435/7.1; 435/325; 436/501

(58) Field of Classification Search
USPC .......... 435/6.1, 7.1, 325; 506/39, 40; 436/501
See application file for complete search history.

(56) References Cited

U.S. PATENT DOCUMENTS

| 5,532,170 A | 7/1996 | Buckle et al. |
| 6,586,259 B1 | 7/2003 | Mahan et al. |

(Continued)

OTHER PUBLICATIONS

PCT/US11/031935, PCT Search Report and Written Opinion dated Jul. 1, 2011.

*Primary Examiner* — Monique Cole
(74) *Attorney, Agent, or Firm* — Pearl Cohen Zedek Latzer, LLP

(57) ABSTRACT

Systems and methods of screening biomarkers in bodily fluids. According to at least one embodiment of the system for analyzing stabilizing agents of the present disclosure, the system comprises a detection platform comprising a plurality of detection sites each capable of receiving a diagnostic marker, a stabilization agent, and a detection agent. The system, in at least one embodiment, further comprises a detection device capable of determining a binding characteristic between the detection agent and the diagnostic marker in the detection sites. Further, the system may also be able to compare the binding characteristic among a plurality of detection markers to order the level of effect of the stabilizing agents assayed on the binding characteristic between the detection agent and the diagnostic agent.

12 Claims, 59 Drawing Sheets

U.S. PATENT DOCUMENTS

| | | | |
|---|---|---|---|
| 6,887,210 B2 * | 5/2005 | Quay | 600/573 |
| 7,732,490 B2 * | 6/2010 | Richon et al. | 514/575 |
| 2007/0065893 A1 | 3/2007 | Carte et al. | |
| 2007/0248533 A1 | 10/2007 | Kuperus et al. | |
| 2008/0248493 A1 | 10/2008 | Mattingly et al. | |
| 2008/0254481 A1 * | 10/2008 | Love et al. | 435/7.1 |
| 2009/0098533 A1 | 4/2009 | Munnes et al. | |
| 2009/0111121 A1 | 4/2009 | Des Rosiers et al. | |
| 2010/0092978 A1 * | 4/2010 | Luk et al. | 435/6 |

* cited by examiner

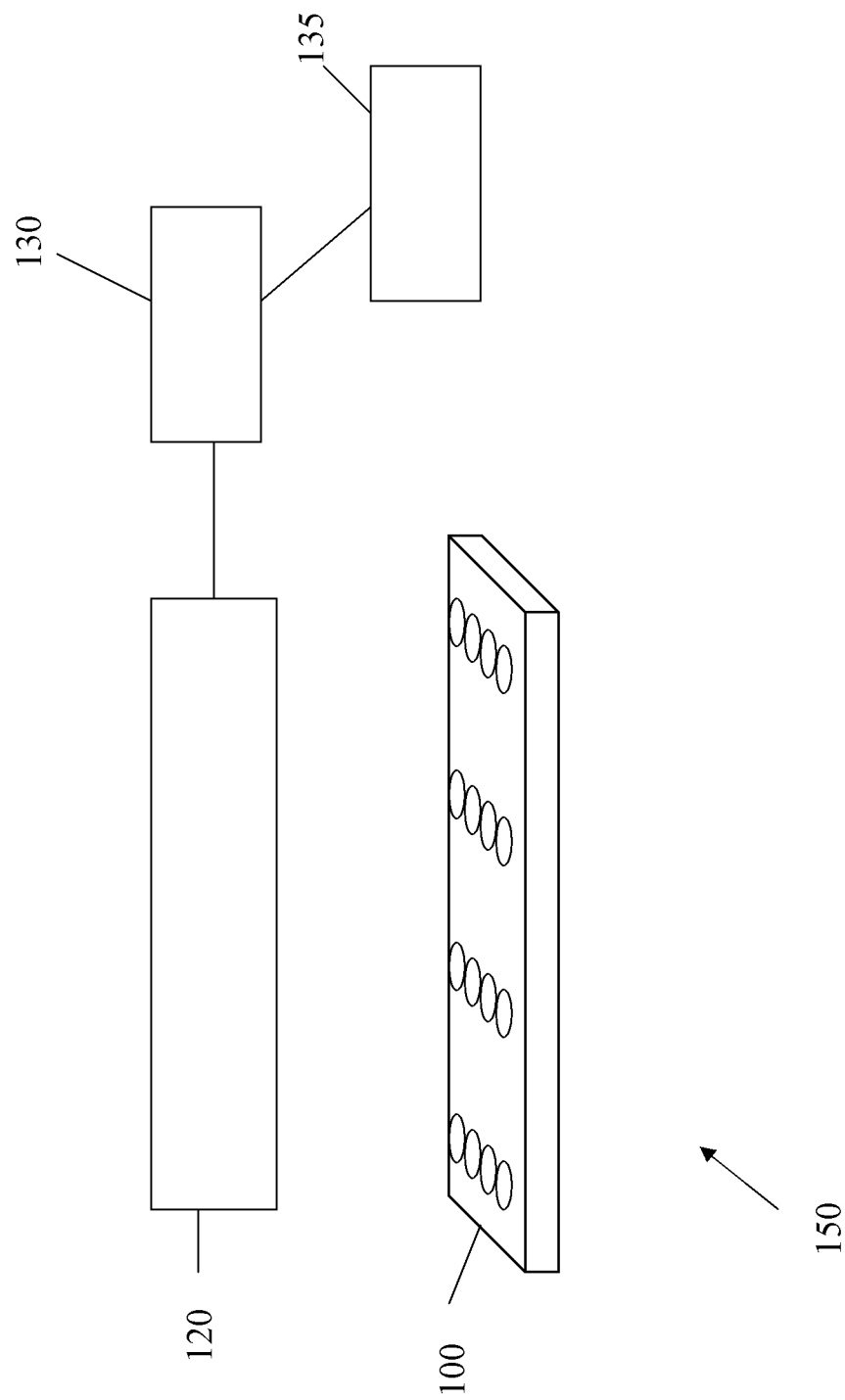

Succinimidyl 4-[*N*-Maleimidomethyl]
Cyclohexane-1-Carboxylate

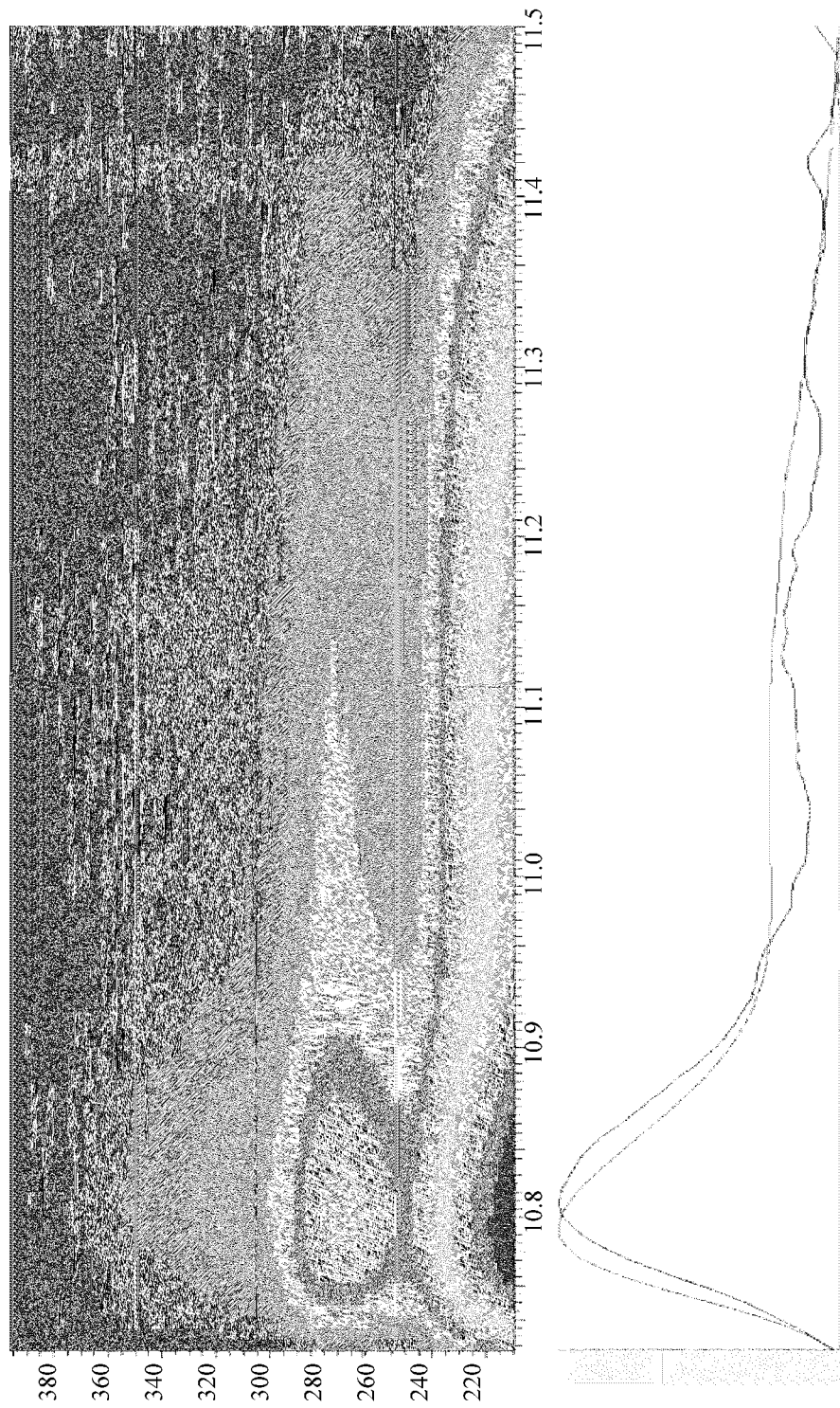

SYSTEMS AND METHODS OF SCREENING BIOMARKERS IN BODILY FLUIDS

PRIORITY

This U.S. utility patent application claims the priority benefit of U.S. Provisional Patent Application Ser. No. 61/390,002, filed Oct. 5, 2010; U.S. Provisional Patent Application Ser. No. 61/385,347, filed Sep. 22, 2010; U.S. Provisional Patent Application Ser. No. 61/383,401, filed Sep. 16, 2010; U.S. Provisional Patent Application Ser. No. 61/379,598, filed Sep. 2, 2010; U.S. Provisional Patent Application Ser. No. 61/378,960, filed Sep. 1, 2010; U.S. Provisional Patent Application Ser. No. 61/373,619, filed Aug. 13, 2010; U.S. Provisional Patent Application Ser. No. 61/364,964, filed Jul. 16, 2010; U.S. Provisional Patent Application Ser. No. 61/364,969, filed Jul. 16, 2010; U.S. Provisional Patent Application Ser. No. 61/364,975, filed Jul. 16, 2010; U.S. Provisional Patent Application Ser. No. 61/364,978, filed Jul. 16, 2010; U.S. Provisional Patent Application Ser. No. 61/364,982, filed Jul. 16, 2010; U.S. Provisional Patent Application Ser. No. 61/365,179, filed Jul. 16, 2010; U.S. Provisional Patent Application Ser. No. 61/322,768, filed Apr. 9, 2010; and U.S. Provisional Patent Application Ser. No. 61/303,165, filed Feb. 10, 2010. The contents of each of these applications are hereby incorporated by reference in their entirety into this disclosure.

BACKGROUND

Biomarkers are molecular indicators of a specific biological property, a biochemical feature or facet that can be used to measure the progress of a disease or the effects of a treatment. For example, serum low-density lipoprotein (LDL) is a biomarker of cholesterol and blood pressure, while the P53 gene is a biomarker for cancer. For chronic diseases and conditions, such as diabetes and allergies, accurate diagnosis is particularly important, especially where the side effects of a treatment are severe.

Diagnostic tests using biomarkers as molecular indicators not only detect the presence or absence of the biomarker, but often must measure the exact concentration of a biomarker to determine whether an abnormal condition exists. Because of the requirement for accuracy, the process of sample collection, preparation, and analysis are often complicated and time consuming. Currently, blood-based assays for biomarker presence or activity are considered to be the "gold standard" for biomarker-type assays.

Despite the desire for accurate results, rapid, point of care analysis of biological samples using biomarkers is becoming increasingly important in the present medical environment due to the need for quick results.

SUMMARY

The disclosure of the present application provides systems for analyzing stabilizing agents.

According to at least one embodiment of the system for analyzing stabilizing agents of the present disclosure, the system comprises a detection platform comprising a plurality of detection sites each capable of receiving a diagnostic marker, a stabilization agent, and a detection agent. The system, in at least one embodiment, further comprises a detection device capable of determining a binding characteristic between the detection agent and the diagnostic marker in the detection sites, a computer database capable of receiving a plurality of binding characteristics, the plurality of binding characteristics comprising at least one binding property of a diagnostic marker to a detection agent, a processor operably coupled to the computer database and the detection device, the processor having and executing a software program operational to determine the binding characteristic of the detection agent to the diagnostic marker in each of the plurality of detection sites, compare the binding characteristic among each of the plurality of detection sites to order the level of effect of the stabilizing agents assayed on the binding characteristic between the detection agent and the diagnostic agent, generate a binding report using the compared binding characteristics, and deliver the binding report to a recipient.

In at least one embodiment of the system for analyzing stabilizing agents of the present disclosure, the stabilizing agent is selected from the group consisting of a protease inhibitor, a DNase inhibitor, and a RNase inhibitor. Further, the stabilizing agent may act to prevent the degradation or inactivation of the diagnostic marker for at least a twenty four hour period following interaction with the diagnostic agent.

In at least one embodiment of the system for analyzing stabilizing agents of the present disclosure, the diagnostic marker is selected from the group consisting of a protein, a glycoprotein, a nucleic acid, an enzyme, an enzyme inhibitor, and a metabolite.

In at least one embodiment of the system for analyzing stabilizing agents of the present disclosure, the stabilizing agent is useful to completely or substantially inactivate an enzyme selected from the group consisting of an amylase, a lysozyme, a peroxidase, a glycosidase, an esterase, a protease, and a peptidase. Moreover, in at least one embodiment, the stabilizing agent may be selected from the group consisting of Fixanal® Buffer 6.0 (Sigma-Aldrich Co.), acetic acid, aluminum hydroxide bentonite, aluminum sulfate hydrate, aluminum potassium sulfate dodecahydrate, benzoic acid, caffeine, and 3-tert-butyl-hydroxyanisole, or a combination thereof. Additionally, an embodiment of the stabilizing agent may comprise a plurality of stabilizing agents each present in approximately the same concentration.

In at least one embodiment of the system for analyzing stabilizing agents of the present disclosure, the stabilizing agent is capable of inhibiting degradation of the diagnostic marker to an inhibitory degree, wherein the inhibitory degree is selected from the group consisting of at least about 40%, at least about 45%, at least about 50%, at least about 55%, at least about 60%, at least about 65%, at least about 70%, at least about 75%, at least about 80%, at least about 85%, at least about 90%, at least about 95%, and at least about 99%.

In at least one embodiment of the system for analyzing stabilizing agents of the present disclosure, the stabilizing agent has a concentration selected from the group consisting of about 200 parts per million (ppm) to about 2000 ppm, about 400 ppm to about 1600 ppm, about 600 ppm to about 1400 ppm, about 800 ppm to about 1200 ppm, and about 400 ppm to about 600 ppm.

In at least one embodiment of the system for analyzing stabilizing agents of the present disclosure, the stabilizing agent is able to inhibit the degradation or inactivation of the diagnostic marker for an inhibitory period selected from the group consisting of at least one minute, at least about five minutes, at least about ten minutes, at least about fifteen minutes, at least about thirty minutes, at least about one hour, at least about two hours, at least about four hours, and at least about eight hours.

In at least one embodiment of the system for analyzing stabilizing agents of the present disclosure, the diagnostic marker is selected from the group consisting of Aldose reductase, Angiogenin, Annexin A1, B-cell activating factor (BAFF), B-cell lymphoma 2 (BCL2)-like 2, Beta Human chorionic gonadotropin, Ca15-3, Calcyclin, Calvasculin, Cancer Antigen CA 19-9, Cancer Antigen CA 15-3, Cathepsin D, Caveolin-1, Chromogranin A, Alpha-crystallin B chain (CRYAB), Endostatin, Eotaxin-2, Epithelial cell adhesion molecule (EpCAM), Ezrin, fatty acid binding protein 4 (FABP4), Galectin-3, γ-glutamylcysteine ligase regulatory chain (GCLR), Gelsolin, Glucose 6-phosphate (G6P), Glycoprotein 130 (gp130), Glutathione S-transferase Mu 1 (GSTM1), Hepsin, High-mobility group protein B1 (HMGB-1), Insulin-like growth factor binding protein 1 (IGFBP-1), Insulin-like growth factor binding protein 4 (IGFBP-4), Insulin-like growth factor binding protein 5 (IGFBP-5), Insulin-like growth factor binding protein 6 (IGFBP-6), LGL, latency associated peptide (LAP), macrophage stimulating protein (MSP), MHC class I polypeptide-related sequence A (MICA), Nucleoside diphosphate kinase B (NME2), Neuron-specific Enolase (NSE), Osteopontin, Osteoprotegerin, Pepsinogen, Peroxiredoxin, Phosphoserine aminotransferase (PSAT1), Prostate Specific Antigen, Receptor tyrosine-protein kinase erbB-3 (ErbB3), Serpin B3, Vascular smooth muscle cell growth factor R2 (VSGF R2/KDR), Vascular endothelial growth factor R3 (VEGF R3/Flt-4), Thyroglobulin, Tyrosine kinase with immunoglobulin-like and EGF-like domains 2 (TIE-2), Tissue plasminogen activator (tPA), Transforming growth factor beta (TGF-β1), Tumor necrosis factor receptor 1 (TNF-R1), urokinase-type Plasminogen Activator (uPA), urokinase-type Plasminogen Activator Receptor (uPAR), BrcaI, BrcaII, kallikreins, e-cadherin, Hox peptide, and Engrailed-2.

DESCRIPTION OF THE DRAWINGS

The features and advantages of the present disclosure, and the manner of attaining them, will be more apparent and better understood by reference to the following descriptions taken in conjunction with the accompanying figures, wherein.

DETAILED DESCRIPTION

Figure 1A:
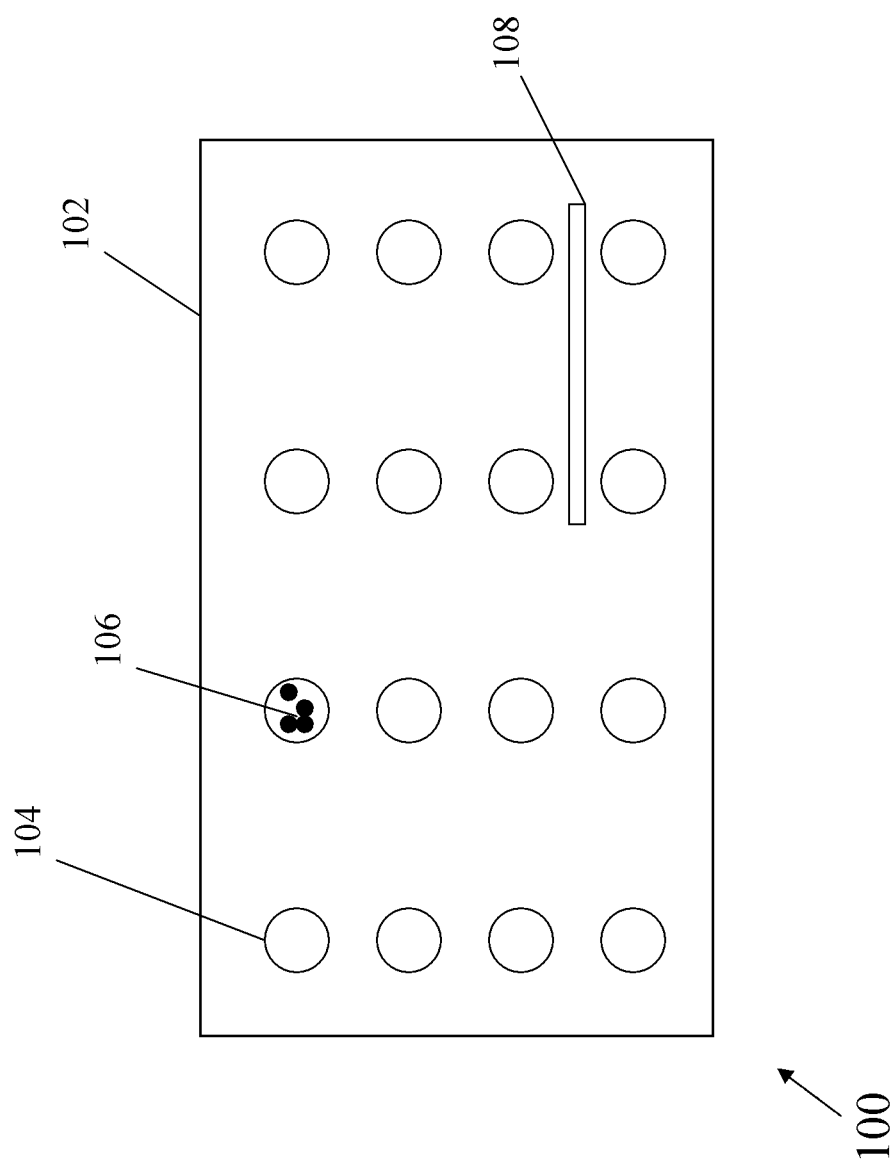
FIGS. 1A and B show a diagram of a detection system, according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosure of the present application provides various compositions, systems, and methods for biomarker stabilization and analysis. Specifically, formulations are disclosed herein, which function to preserve the level of diagnostic markers, such as biomarkers, in body fluids, from enzymatic alteration, or degradation. Additionally, methods for the collection and analysis of body fluids are disclosed. The methods and formulations disclosed herein can be used to improve the sampling and testing of a body fluid by conditioning the body fluids for the stabilization of specific biomolecules and/or drug metabolites. As used herein, the term "body fluids" includes fluids produced by the body, such as saliva, or fractions thereof, mucous secretions, tears, sweat, bile, semen, urine, vaginal secretions, exhalations, anal secretions, blood, plasma, serum and mixtures of thereof. Body fluids may also comprise cancer cells, peripheral blood mononuclear cells, lymphocytes, lymph fluid, and other tissue secretions or fluid.

Saliva

Saliva is clear, viscous fluid with a slightly alkaline pH and a pI range from 11.5-3.0. It is hypotonic, composed of about 99.5% water, and also contains ions (e.g., $K^+$, $Na^+$, $Ca^{2+}$, $Mg^{2+}$, $H^+$, $Cl^-$, $HCO_3^-$, $F^-$, $HPO_4^{2-}$), and small organic molecules (e.g., ureas, hormones, lipids, DNA, and RNA). There are multiple contributors to the composition of saliva. Saliva has a complex "proteome"—$10^6$ D glycoproteins to 1000D peptides. It contains secretory products of salivary glands, products of B cells, PMNs, epithelial cells, and bacteria. Major (e.g., parotid, submandibular, and sublingual) and minor (e.g., palatine and retromolar) glands contribute to the composition of saliva, along with extraneous contributors such as gingival crevicular fluid, serum proteins, white blood cells and their byproducts, oral epithelial cells, oral bacteria, food debris and dissolved food components.

Saliva from different glands may differ in composition. For example, saliva from the parotid gland is dominated by serous secretory cells, whereas saliva from the submandibular and sublingual glands and minor glands are mixed serous or mostly mucous. There can also be qualitative and quantitative differences in saliva output that affect its composition. Glandular contribution to saliva is affected by level of gland activity. The amount of saliva secreted per minute or the salivary flow rate influences the concentration of the constituents as well as the proportion of the constituents from each of the three pairs of major salivary glands and the minor salivary glands.

I. Stabilizing Agents

According to at least one embodiment of the present disclosure, conditioning of body fluids for the preservation of diagnostic markers may be accomplished through the use of stabilizing agents, which may be incorporated into one or more carrier vehicles, such as rinses, gums, beverages, and confectionaries. For example, specific rinses and/or pre-rinses specially formulated according to the specific molecule or molecules (the diagnostic marker) to be detected in the body fluid, may contain a stabilization agent. The use of rinses and pre-rinses of the present disclosure to condition the body fluid may enhance the sensitivity for detection of specific diagnostic markers for clinical diagnosis. Additionally, this process may improve the signal-to-noise ratio for a better diagnostic yield. Further, each rinse/pre-rinse can be specifically formulated to reduce or prevent false positive and false negative results.

In at least one embodiment of a stabilizing agent of the present disclosure, the stabilizing agent may act to prevent/decrease the degradation, or reduction of activity, of diagnostic markers. In at least one embodiment, the stabilizing agent may be comprised of one or more Generally Regarded as Safe (GRAS) compound, as determined by the Food and Drug Administration of the United States of America, such as those listed in Table I. An exemplary embodiment of a stabilization agent may act to stabilize a diagnostic marker, and/or to bind to a destructive component to prevent the destructive component from degrading or decreasing the activity of the diagnostic marker.

In additional exemplary embodiments of the stabilization agent, the stabilizing agent may comprise at least 2, at least 3, at least 4, at least 5, at least 6, at least 7, at least 8, at least 9, at least 10, at least 15, at least 20, or at least 25 compounds which acts to stabilize the diagnostic marker, and/or to bind to a destructive component to prevent the destructive component from degrading or decreasing the activity of the diagnostic marker. Further, in various embodiments the stabilizing agent of the present disclosure may be present in at a level of between about 200 ppm to about 2,000 ppm, about 400 ppm to about 1600 ppm, about 600 ppm to about 1400 ppm, about 800 ppm to about 1200 ppm. Moreover, in at least one embodiment, the stabilizing agent may be present at a level of approximately 500 ppm.

TABLE I

GRAS Compounds as Stabilizing Agents

| | | |
|---|---|---|
| 1 | Agar | Sigma-Aldrich |
| 2 | Alginic acid sodium salt | Sigma-Aldrich |
| 3 | L-Ascorbic acid | Sigma-Aldrich |
| 4 | (+)-Sodium ascorbate | Sigma-Aldrich |
| 5 | Buffer solution | Fluka |
| 6 | Sodium citrate | Sigma-Aldrich |
| 7 | Tragacanth | Sigma-Aldrich |
| 8 | Gum arabic, from *acacia* tree | Sigma-Aldrich |
| 9 | Sodium tripolyphosphate | Sigma-Aldrich |
| 10 | Potassium citrate monobasic | Sigma-Aldrich |
| 11 | Sodium pyrophosphate tetrabasic | Sigma-Aldrich |
| 12 | Calcium citrate | Sigma-Aldrich |
| 13 | Citric acid | Sigma-Aldrich |
| 14 | Potassium sodium tartrate tetrahydrate | Sigma-Aldrich |
| 15 | Sodium benzoate | Sigma-Aldrich |
| 16 | Benzoic acid | Sigma-Aldrich |
| 17 | D-aspartic acid | Sigma-Aldrich |
| 18 | Sodium phosphate dibasic | Sigma-Aldrich |
| 19 | Malic acid | Sigma-Aldrich |
| 20 | Sodium propionate | Sigma-Aldrich |
| 21 | Sodium L-ascorbate | Sigma-Aldrich |
| 22 | DL-Phenylalanine | Sigma-Aldrich |
| 23 | Calcium L-ascorbate dihydrate | Sigma-Aldrich |
| 24 | Choline chloride | Sigma-Aldrich |
| 25 | L-Ascorbic acid | Sigma-Aldrich |
| 26 | Sodium diacetate | SAFC |
| 27 | PH buffer 4.01 | Orion |
| 28 | PH Buffer 7.00 | Orion |
| 29 | PH buffer 10.0 | Orion |
| 30 | Fixanal Buffer 6.0 | Sigma-Aldrich |
| 31 | Ammonium Chloride | Sigma-Aldrich |
| 32 | Ammonium Citrate tribasic, anhydrous | Sigma-Aldrich |
| 33 | Caffeine | Sigma-Aldrich |
| 34 | Aluminum sulfate hydrate | Sigma-Aldrich |
| 35 | Beeswax refined | Sigma-Aldrich |
| 36 | Aluminum Hydroxide | Sigma-Aldrich |
| 37 | Bentonite | Sigma-Aldrich |
| 38 | Ammonium bicarbonate | Sigma-Aldrich |
| 39 | 3-tert--butyl-hydroxyanisole | Sigma-Aldrich |
| 40 | Benzoic acid | Sigma-Aldrich |
| 41 | trans-aconitic acid | Sigma-Aldrich |
| 42 | Aluminum potassium sulfate dodecahydrate | Sigma-Aldrich |
| 43 | Adpic acid | Sigma-Aldrich |
| 44 | Ammonium hydrogen phosphate | Sigma-Aldrich |
| 45 | Ammonium dihydrogen phosphate | Sigma-Aldrich |
| 46 | Ammonium carbonate | Sigma-Aldrich |
| 47 | Acetic acid | Sigma-Aldrich |

According to at least one exemplary embodiment, the stabilizing agent may block at least one enzymatic activity of a destructive component. The destructive component may be one or more component of a bodily fluid which acts to degrade, or decrease the activity of a diagnostic marker. Further, the destructive component may be one or more Amylases, Lysozymes, Peroxidases, Glycosidases, Esterases, Proteases, and/or Peptidases. In an exemplary embodiment, the stabilizing agent may be a naturally occurring or artificial protease inhibitor, DNase inhibitor, or RNase inhibitor. Specifically, a natural stabilizing agent may include any component found from food products (including, but not limited to, the Solanaceae family), herbs, or spices that acts to decrease the effect of a destructive component. For example, exemplary embodiments of the natural stabilizing agents may be any of the inhibitors found in lima beans, soybeans, or avian eggs (such as ovomucoid glycoprotein protease inhibitors) (See Table II). Moreover, an embodiment of the stabilizing agent may also comprise a molecule which specifically inhibits the activity of a molecule which targets the diagnostic marker for degradation or inactivation. Further, the stabilizing agent may act to alter the composition of the body fluid (such as pH, or ion concentration) to decrease the degradation or inactivation of the diagnostic marker.

TABLE II

| Material | Molecular weight | Inhibitory power | Details |
|---|---|---|---|
| Lima beans | 8-10 kDa | 2.2 times weight | There are six different lima bean inhibitors. |
| Ovomucoid | 8-10 kDa | 1.2 times weight | Ovomucoids are the glycoprotein protease inhibitors found in raw avian egg white. There are other protease inhibitors in ovomucoids as well. |
| Soybeans | 20.7-22.3 kDa | 1.2 times weight | Soybeans contain several inhibitors; the one in the chart is considered the primary one. All of them bind chymotrypsin to a lesser degree. |

As used herein, "diagnostic marker" may be any biological molecule whose presence, specific concentration, or specific activity may be indicative of a disease state or heath/lifestyle characteristic. As used herein, "indicative of a disease state" refers to the presence, progression, prevention, remission, amelioration, or prognosis of a disease. This also includes, but is not limited to, the effects of a therapeutic on a disease. The disease state analyzed through use of the diagnostic marker may in an exemplary embodiment be directed towards any cancer, metabolic disease (such as diabetes I or II), cardiovascular disease, or the predisposition of any of the same. Additionally, a disease state may also include the infection of the patient by a bacterial, virus, yeast, fungus, or parasite.

A. Disease States

Bacterial infections, as referenced herein, may include a mammalian infection by any bacterial species. Embodiments of the bacterial species, as used herein, may include, but are not limited to, *Bacillus anthracis, Bacillus cereus, Staphylococcus aureus, Listeria monocytogenes, Streptococcus pneumoniae, Streptococcus pyogenes, Clostridium botulinum, Clostridium difficile, Clostridium perfringens, Clostridium tetani, Borrelia burgdorferi, Treponema pallidum, Chlamydia trachomatis, Chlamydophila psittaci, Corynebacterium diphtherias, Mycobacterium tuberculosis,* and *Mycobacterium avium, Rickettsia prowazekii, Rickettsia rickettsii, Rickettsia typhi, Anaplasma phagocytophilum, Ehrlichia chaffeensis, Brucella melitensis, Bordetella pertussis, Burkholderia mallei, B. pseudomallei, Neisseria gonorrhoeae, Neisseria meningitides, Campylobacter jejuni, Helicobacter pylori, Legionella pneumophila, Acinetobacter baumannii, Moraxella catarrhalis, Pseudomonas aerugi-*

*nosa, Aeromonas* sp., *Vibrio cholerae, Vibrio parahaemolyticus, Thiotrichales* sp., *Haemophilus influenzae, Klebsiella pneumoniae, Proteus mirabilis, Yersinia pestis, Yersinia enterocolitica, Shigella flexneri, Salmonella enterica,* and *Escherichia coli.*

Viral infections, as referenced herein, may include a mammalian infection by any viral species. Embodiments of the viral species, as used herein, may include, but are not limited to, single-stranded DNA viruses, including the genus Parvoviridae, double-stranded DNA viruses, including the genus *Papillomaviridae, Polyomaviridae, Poxviridae, Herpesviridae* (ex. Herpes Simplex Virus 1, 2, 6, Varicella-zoster virus, Epstein-Barr virus EBV, Human cytomegalovirus, and human herpesvirus 7), single-stranded RNA viruses, Reo- and Retroviruses (ex. Hepatitis B virus, Human immunodeficiency virus 1 and 2, and Human T-lymphotropic virus 1).

Fungal infections, as referenced herein, may include a mammalian infection by any bacterial species. Embodiments of the fungal species, as used herein, may include, but are not limited to, *Fusarium oxysporum, Pneumocystis jirovecii, Aspergillus* spp., *Coccidioides immitis/posadasii, Candida albicans, Filobasidiella neoformans, Trichosporon, Encephalitozoon cuniculi, Enterocytozoon bieneusi, Mucor circinelloides, Rhizopus oryzae,* and *Lichtheimia corymbifera.*

Parasite infections, as referenced herein, may include a mammalian infection by any parasite. Embodiments of the parasite may be, but are not limited to, *Entamoeba histolytica, Babesia microti, Babesia* sp. WA1, *Trypanosoma cruzi, Taenia solium, Echinococcus granulosus, Leishmania braziliensis, L. donovani, L. tropica, Plasmodium falciparum, Plasmodium vivax, Plasmodium ovale* and *Plasmodium malariae, Plasmodium knowlesi, Paragonimus westermani, chistosoma* sp., *S. mansoni, S. haematobium, S. japonicum, Strongyloides stercoralis, Toxocara canis, Toxoplasma gondii, Trichinella spiralis African trypanosomiasis, Ancylostoma, Angiostrongylus, Anisakis, Baylisascaris procyonis, Clonorchis (Opisthorchis) sinensis, Echinococcus multilocularis, Fasciola hepatica,* Filariasis, *Gnathostoma*

Exemplary embodiments of diagnostic markers include those listed in Table III. Further exemplary embodiments for the diagnosis of type-II diabetes include, but are not limited to, Albumin, Alpha-1 antitrypsin (A1AT)—G Protein, Cystatin C, Cystatin A, alpha-2-macroglobulin (A2MG), Uteroglobin, Transthyretin (TTR), Annexin A1, Annexin A2, Annexin A3 and Calnexin.

Diagnostic markers directed towards cardiovascular disease, in an exemplary embodiment, may include, but are not limited to, any isoform of creatine kinase, troponin I and T, LD, Myoglobin, ALT/AST, H-FABP, and Glycogen phosphorylase B.

Diagnostic markers directed towards cancer, in addition to those described in Table III, may include, but are not limited to, Aldose reductase, Angiogenin, Annexin A1, B-cell activating factor (BAFF), B-cell lymphoma 2 (BCL2)-like 2, Beta Human chorionic gonadotropin, Ca15-3, Calcyclin, Calvasculin, Cathepsin D, Caveolin-1, Chromogranin A, Alpha-crystallin B chain (CRYAB), Endostatin, Eotaxin-2, Epithelial cell adhesion molecule (EpCAM), Ezrin, fatty acid binding protein 4 (FABP4), Galectin-3, γ-glutamylcysteine ligase regulatory chain (GCLR), Gelsolin, Glucose 6-phosphate (G6P), Glycoprotein 130 (gp130), Glutathione S-transferase Mu 1 (GSTM1), Hepsin, High-mobility group protein B1 (HMGB-1), Insulin-like growth factor binding protein 1 (IGFBP-1), Insulin-like growth factor binding protein 4 (IGFBP-4), Insulin-like growth factor binding protein 5 (IGFBP-5), Insulin-like growth factor binding protein 6 (IGFBP-6), LGL, latency associated peptide (LAP), macrophage stimulating protein (MSP), MHC class I polypeptide-related sequence A (MICA), Nucleoside diphosphate kinase B (NME2), Neuron-specific Enolase (NSE), Osteopontin, Osteoprotegerin, Pepsinogen, Peroxiredoxin, Phosphoserine aminotransferase (PSAT1), Prostate Specific Antigen, Receptor tyrosine-protein kinase erbB-3 (ErbB3), Serpin B3, Vascular smooth muscle cell growth factor R2 (VSGF R2/KDR), Vascular endothelial growth factor R3 (VEGF R3/Flt-4), Thyroglobulin, Tyrosine kinase with immunoglobulin-like and EGF-like domains 2 (TIE-2), Tissue plasminogen activator (tPA), Transforming growth factor beta (TGF-β1), Tumor necrosis factor receptor 1 (TNF-R1), urokinase-type Plasminogen Activator (uPA), urokinase-type Plasminogen Activator Receptor (uPAR), Brca1, BrcaII, kallikreins, e-cadherin, Hox peptide, and Engrailed-2.

Diagnostic markers directed towards a bacterial or virus may include any surface or secreted antigen from the bacteria or virus, or a conserved nucleotide sequence.

TABLE III

| Tumor Marker | Relevant Cancer | Present in Serum/ Plasma | Present in Saliva | Class of Molecules |
|---|---|---|---|---|
| α-fetoprotein | Heptacellular carcinoma | Yes | Yes | Protein |
| Cancer Antigen (CA15-3) | Breast cancer | Yes | Yes | Protein |
| Cancer Antigen (CA 125) | Ovarian cancer | Yes | Yes | Protein |
| Carcinoembryonic antigen | Many epithelial cancers | Yes | Yes | |
| Prostate specific antigen | Prostate cancer | Yes | Yes | Protein |
| c-erb-2 | Breast cancer | | Yes | Nucleic acid |
| P16, p53 | Oral SCC | | | |
| BRACA1, BRACA2 | Breast cancer | Yes | Yes | Nucleic acid |
| Hemoglobin-A1c | | | Yes | Protein |

B. Diagnostic Markers

Further, diagnostic markers according to an embodiment of the present disclosure may include one or more of: 1,25 dihydroxy-vitamin D, 17-Hydroxyprogesterone, 25-hydroxy-vitamin D, Antineutrophil Cytoplasmic Antibodies, 5-Hydroxy Tryptamine, 5-hydroxyindoleacetic acid, Acetoacetate, Activated Partial Thromboplastin Time, Adrenocorticotropic Hormone, Alanine aminotransferase, Alanine transaminase, Albumin, Albumin-to-Creatinine ratio, Albumin/Globulin ratio, Alcohol, Aldolase, Aldosterone, Aldosterone and plasma renin activity, Aldosterone and Renin, Alkaline Phosphatase, Allergen-specific IgE, Alpha tryptase, Alpha-1 Antitrypsin, Alpha-fetoprotein, Alpha1-antitrypsin, Alzheimer biomarkers (including Tau protein and Amyloid Beta 42 peptides), Amylase, ANCA Antibodies, ANCA/MPO/PR3 Antibodies, Angiotensin-Converting Enzyme, Anti-citrulline antibody, anti-cyclic citrullinated peptide antibody, Anti-retroviral drug resistance testing, anti-ribonucleoprotein, anti-Sjögren's Syndrome A, anti-Sjögren's Syndrome B, Anti-Smooth Muscle Antibody, anti-topoisomerase, Anticardiolipin Antibodies, Antidiuretic Hormone, Antifactor Xa heparin, Antiglobulin, Antihistidyl Transfer RNA, Synthase Antibodies, Antimicrosomal antibody, Antimitochondrial Antibody and Antimitochondrial M2 Antibody, Antineutrophil Cytoplasmic Antibodies, Antinuclear Antibody test, Antiphospholipid antibodies, Antiphospholipids, Antistreptolysin O titer, Antithrombin, Antithyroglobulin antibody, Antithyroid antibodies, Apolipoprotein A-I, Apolipoprotein B-100, Arginine Vasopressin, Aspartate aminotransferase, Aspartate transaminase, B-type natriuretic peptide, Beta hCG, Beta tryptase, Beta-2 Microglobulin, Beta-hydroxybutyrate, Beta-hydroxybutyric acid, Beta2 Microglobulin, Bicarbonate, Bilirubin, cholesterol, Blood clotting factors, *Bordetella pertussis* Antibodies, *Borrelia burgdorferi* antibodies, IgM/IgG, Brain natriuretic peptide, Breast Cancer Gene 1 and Breast Cancer Gene 2, c-ANCA, c-erbB-2, C-peptide, C-Reactive Protein, Caffeine, Calcidiol, Calcifidiol, Calcitonin, Calcitriol, Calcium, Calcofluor white stain, Cancer Antigen 125, Cancer Antigen 15-3, Cancer Antigen 19-9, Cancer antigen-breast, Cancer antigen-GI, Carbamazepine, Carcinoembryonic Antigen, Cardiac-specific Troponin I and Troponin T, Cardiolipin Antibodies, Catecholamines, Celiac Disease Tests, Ceruloplasmin, Chickenpox, Chickenpox and Shingles Tests, Chlamydia, Chloride, Cholesterol, Chromogranin A, Chymotrypsin, Citrulline antibody, Coagulation Factors, Cobalamin, Complement Component C3, Complement Component C4, Complexed PSA, Conjugated bilirubin, Copper, Corticotropin, Cortisol, Cotinine, Creatine Kinase, Creatine Kinase-MB, Creatinine, Cryoglobulin, Cryoprotein, Cyclic Citrullinated Peptide Antibody, Cyclosporine, Cystatin C, Cystic Fibrosis Gene Mutation Panel, Cystic fibrosis genotyping, Cytomegalovirus, Cytotoxic T-cells, Dehydroepiandrosterone Sulfate, Delta-aminolevulinic acid, Depakene, Depakote, Des-gamma-carboxy prothrombin, DHEA Sulfate, Diabetes mellitus autoantibody panel, Digoxin, Dilantin, Direct Anti-human Globulin test, Direct Antiglobulin Test, Direct bilirubin, Direct Low-density lipoprotein cholesterol, Dopamine, Drug screen, eGFR, Epidermal Growth Factor Receptor, Epinephrine, Epstein-Barr Virus Antibodies, Erythropoietin, Estradiol, Estriol, Estrogens, Estrone, Ethanol, F-Actin Antibody, Factor I, Factor V Leiden, Factor V Leiden Mutation and PT 20210 Mutation, Factor V Leiden mutation: Activated protein C resistance, Factor V R506Q, Ferritin, Fetal fibronectin, Fibrin degradation fragment, Fibrinogen, Fluorescent Antinuclear Antibody, Fluorescent treponemal antibody absorption, Folic Acid, Follicle-stimulating hormone, Fragment D-dimer, Fructosamine, Gamma-glutamyl transferase, Gamma-glutamyl transpeptidase, Gastrin, Genital Human Papillomavirus, Glucose-6-Phosphate Dehydrogenase, Glutamic Acid Decarboxylase Autoantibodies, Gluten-Sensitive Enteropathy Tests, Glycated Albumin, Glycated hemoglobin, Heavy Metals (such as lead, mercury, iron, copper, and zinc), Hemoglobin, Hemoglobin-binding Protein, Hemogram, Heparin Anti-Xa, Hepatitis A, Hepatitis B, Hepatitis C, Herpes Simplex Virus, Type1 and Type 2, Herpes Zoster, Heterophile Antibodies, High-density lipoprotein cholesterol, High-sensitivity C-reactive protein, Homocysteine, Human calcitonin, Human chorionic gonadotropin, Human epidermal growth factor receptor, Human Growth Hormone, Human immunodeficiency virus antibody test, Human Immunodeficiency Virus Genotypic Resistance Testing, Human Leukocyte Antigen, Immunoreactive trypsinogen, Insulin Autoantibodies, Insulin C-peptide, Insulin-like Growth Factor-1, Insulinoma-Associated-2 Autoantibodies, Intact PTH, Interstitial Cell Stimulating Hormone, Iron, Ischemia-Modified Albumin, Islet autoantibodies Islet Cell Cytoplasmic Autoantibodies, Janus Kinase 2, Ketone bodies Ketones, blood, Lactate, Lactate dehydrogenase, Lactic Acid, Lactic dehydrogenase, Lead, Lipoprotein, Lithium, Low-density lipoprotein cholesterol, Lupus Antibody, Luteinizing hormone, Lyme antibodies IgM/IgG by Western blot, Magnesium, Mast cell tryptase, Measles or Mumps IgM and IgG Antibodies, Mercury, Metanephrine and Normetanephrine, Methotrexate, Methylmalonic Acid, Microalbumin, Mitochondrial Antibody, Mononuclear heterophile test, Mycophenolic acid, Mycoplasma, Mycoplasma pneumoniae IgG and IgM antibodies, Myeloperoxidase Antibodies, Myoglobin, N-terminal pro b-type natriuretic peptide, Neonatal bilirubin, Nicotine, Norepinephrine, p24 antigen, Parathyroid Hormone, Parvovirus, Pertussis, Phenobarbital, Phenytoin, Phosphate, Phosphorus, Platelet-activating factor acetylhydrolase, porphobilinogen, Potassium, Prealbumin, Presenilin 1 gene, Procalcitonin, Progesterone, Proinsulin C-peptide, Prolactin, Prostate Specific Antigen, Protein C, Protein C and Protein S, Protein Tyrosine Phosphatase-like Autoantibodies, Proteinase 3 Antibodies, Prothrombin 20210 mutation, Prothrombin 20210 mutation: PT G20210A, factor II 20210, Red Blood Cell Antibody Identification, Renin, Respiratory Syncytial Virus, Rheumatoid Factor, Ristocetin Cofactor, Rubella, Scleroderma antibodies, Serine Protease 3, Serotonin, Siderophilin, Sirolimus, Smith antibody, Smooth Muscle Antibody, Sodium, Soluble Mesothelin-Related Peptides, Somatomedin C, Somatotropin, Syphilis, Tacrolimus, Tegretol®, Testosterone, Testosterone-estrogen Binding Globulin, Theophylline, Theophylline and Caffeine, Thiopurine methyltransferase, Thiopurine S-methyltransferase, Thymotaxin, Thyrocalcitonin, Thyroglobulin, Thyroid peroxidase antibody, Thyroid stimulating hormone receptor antibody, Thyroid stimulating immunoglobulin, Thyroid-stimulating hormone, Thyroperoxidase antibody, Thyrotropin, Thyroxine, Thyroxine-binding prealbumin, Transferrin, Transthyretin test, Treponema pallidum particle agglutination assay, Trichomonas, Trichomoniasis, Triglycerides, Triiodothyronine, Troponins, Trypsin, Trypsin and Chymotrypsin, Trypsinogen, Tryptase, Valproic acid, Vancomycin, Vanillylmandelic acid, Zoster Virus, Vasopressin, Very Low-Density Lipoprotein Cholesterol, Viral Hepatitis A Antibody, Viral Hepatitis C. Viral Load (HIV), Vitamin B12, Vitamin B12 & Folate, Vitamin D, Vitamin D2, Vitamin D3, Vitamin K, von Willebrand Factor, West Nile Virus, Westergren sedimentation rate, and Zinc Protoporphyrin.

C. Exemplary Targets for Stabilizing Agent(s)

1. Amylase

Amylase is an enzyme that breaks down starch into sugar, and is found in such places as human saliva, where it begins the chemical process of digestion. The α-amylases are calciummetalloenzymes that are completely unable to function in the absence of calcium. Through acting at random locations on the starch chain, α-amylase breaks down carbohydrates into maltotriose and maltose from amylase. In animals, α-amylase is a major digestive enzyme that has an optimum pH of 6.7 to 7.0.

In at least one embodiment of a stabilizing agent of the present disclosure, the stabilizing agent may be an inhibitor of α-amylase. Further, the stabilizing agent may be active in a biological fluid, such as in saliva. In an exemplary embodiment, a stabilizing agent may comprise one or more of Fixanal® Buffer 6.0 (Sigma-Aldrich Co.), aluminum sulfate hydrate, aluminum hydroxide, bentonite, and aluminum potassium sulfate dodecahydrate.

2. Lysozyme

Lysozyme, also known as muramidase or N-acetylmuramide glycanhydrolase, is a glycoside hydrolase, that damage bacterial cell walls by catalyzing hydrolysis of 1,4-beta-linkages between N-acetylmuramic acid and N-acetyl-D-glucosamine residues in a peptidoglycan and between N-acetyl-D-glucosamine residues in chitodextrins. Lysozyme is abundant in a number of secretions, such as tears, saliva, human milk, and mucus. It is also present in cytoplasmic granules of the polymorphonuclear neutrophils (PMN).

In at least one embodiment, a stabilizing agent of the present disclosure may be an inhibitor of lysozyme. Further, the stabilizing agent may be active in a biological fluid, such as saliva. In an exemplary embodiment, a stabilizing agent may comprise one or more of Fixanal® Buffer 6.0 (Sigma-Aldrich Co.), bentonite, benzoic acid, and acetic acid.

3. Peroxidase

Peroxidase are a class of oxidoreductase enzymes that catalyze the oxidation of a compound by the decomposition of hydrogen peroxide or an organic peroxide. These peroxidases may be found in many different bodily fluids. For example, saliva contains both salivary peroxidase (SPX) and myeloperoxidase (MPO). These peroxides may act on a number of different diagnostic markers found in bodily fluids to mask the detection or analysis of the markers.

In at least one embodiment of a stabilizing agent of the present disclosure, the stabilizing agent may be an inhibitor peroxidase activity. Further, the stabilizing agent may be active in a biological fluid, such as saliva, blood, serum, or cancer cells. In an exemplary embodiment, a stabilizing agent may comprise one or more of aluminum sulfate hydrate, benzoic acid, and aluminum potassium sulfate dodecahydrate.

4. Insulin Resistance

In at least one embodiment of a stabilizing agent of the present disclosure, the stabilizing agent may preserve a diagnostic marker for insulin resistance and/or glucose intolerance. Further, the stabilizing agent may be active in a biological fluid, such as saliva. In an exemplary embodiment, a diagnostic marker may be one or more of α-hydroxybutyrate, 1-linoleoyl-GPC, palmitate, Glycine, 3-methyl-2-oxybutyrate. Moreover, a diagnostic marker may be any marker of early stage insulin resistance and glucose intolerance in a non-diabetic individual.

5. Galactose Oxidase

Galactose oxidase is a member of the family of oxidoreductaases, and has been shown to participate in galactose metabolism. Because of this activity, galactose oxidase may be used to detect mucin-like glycoproteins. These glycoproteins are a major component of mucus secreted by epithelial and glandular cells and are primarily responsible for the protective properties of the viscoeleastic mucous barrier. Mucins have been implicated in the process of cholesterol gallstone formation, and has been identified as having abnormal expression in some cancers.

In at least one embodiment of a stabilizing agent of the present disclosure, the stabilizing agent may be an inhibitor of galactose oxidase. Further, the stabilizing agent may be active in a biological fluid, such as saliva. In an exemplary embodiment, a stabilizing agent may comprise one or more of aluminum potassium sulfate dodecahydrate, 3-tert-butyl-hydroxyanisole, benzoic acid, and acetic acid.

6. Glycated Hemoglobin

Glycated hemoglobin (HbA1c) is a form of hemoglobin that is indicative of the average plasma glucose concentration over a period of time. Due to the transport of components of the plasma into bodily fluids, such as saliva, the level of HbA1 c may be determined in bodily fluids in addition to plasma.

In at least one embodiment of a stabilizing agent of the present disclosure, the stabilizing agent may be an inhibitor of HbA1c degradation. Further, the stabilizing agent may be active in a biological fluid, such as saliva. In an exemplary embodiment, a stabilizing agent may comprise one or more of acetic acid, aluminum hydroxide bentonite, aluminum sulfate hydrate, aluminum potassium sulfate dodecahydrate, benzoic acid, caffeine, and 3-tert-butyl-hydroxyanisole, or a combination thereof.

7. Cancer Antigen 19-9 (CA 19-9)

Cancer Antigen 19-9 (CA 19-9), which may in some instances be referred to as Cancer Angigen 19.9, Cancer antigen-GI or CA-GI, is an antigen associated with various cancers, such as prostate and colon cancer. At least one use of CA 19-9 may be see whether a pancreatic tumor is secreting antigen. If that is the case, then the levels may decrease when the tumor is treated, and they may rise again if the disease recurs.

In at least one embodiment of a stabilizing agent of the present disclosure, the stabilizing agent may be an inhibitor of CA 19-9 degradation. Further, the stabilizing agent may be active in a biological fluid, such as saliva, blood, serum, or cancer cells. In an exemplary embodiment, a stabilizing agent may comprise one or more of aluminum sulfate hydrate, benzoic acid, and aluminum potassium sulfate dodecahydrate.

Further, in an additional exemplary embodiment, the components of a stabilizing agent may be present at or about equal amounts, such as for example 1:1:1 in a stabilizing agent with three active components. Additionally, the stabilizing agents may in at least one embodiment inhibit degradation or inactivation of a diagnostic marker by at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. Moreover, the stabilizing agent may, in at least one embodiment, inhibit degradation of a diagnostic marker for at least about 1 minute, at least about 5 minutes, at least about 10 minutes, at least about 15 minutes, at least about 30 minutes, at least about 1 hour, at least about 2 hours, at least about 4 hours, or at least about 8 hours.

Additional Components for Stabilizing Agent Carriers:

According to at least one embodiment of the present disclosure, stabilizing agents may be incorporated into various carriers for their use with mammals. Such carriers may include various rinses, gums, lozenge, mouthwash, beverages, confectionary, washes, or other applicable vehicles to deliver a stabilizing agent to the site of a diagnostic marker.

Embodiments of a carrier, such as a rinse, according to the present disclosure may also comprise one or more additional component which may include an anti-caking agent, a chemical preservative, an emulsifying agent, a nutrient and dietary supplement, a sequestrant, a stabilizer, an additive, a synthetic and flavoring substance. Exemplary embodiments of these components are listed herein (See section entitled "Additional Components for Rinse"). Further, the one or more additional component may be a substance which has been labeled as Generally Recognized As Safe (GRAS) by the Food and Drug Administration of the United States of America.

At least one embodiment of a carrier of the present application may comprise a liquid. The liquid, in at least one embodiment, is a non-toxic liquid. Further, the liquid may comprise water, a beverage containing water, or glycerin. Moreover, in at least one embodiment, a stabilizing agent may be at least partially dissolved in the liquid.

It will be appreciated that the above list of excipients and/or additives is provided merely by way of example and that various other such components may be used in the formulation of the present invention.

The following components, in at least one embodiment of the rinse of the present disclosure, may include:

1. ANTI-CAKING AGENTS: aluminum calcium silicate, calcium silicate, magnesium silicate, sodium calcium aluminosilicate, and tricalcium silicate.

2. CHEMICAL PRESERVATIVES: ascorbic acid, ascorbyl palmitate, benzoic acid, butylated hydroxyanisole, butylated hydroxytoluene, calcium ascorbate, calcium propionate, calcium sorbate, caprylic acid, dilauryl thiodipropionate, erythorbic acid, gum guaiac, methylparaben, potassium bisulfite, potassium metabisulfite, potassium sorbate, propionic acid, propyl gallate, propylparaben, sodium ascorbate, sodium benzoate, sodium bisulfite, sodium metahisulfite, sodium propionate, sodium sorbate, sodium sulfite, sorbic acid, stannous chloride, sulfur dioxide, thiodipropionic acid, tocopherols.

3. EMULSIFYING AGENTS: cholic acid, desoxycholic acid, diacetyl tartaric acid esters of (M)mono- and diglycerides, glycocholic acid, mono- and diglycerides, monosodium phosphate derivatives of above, propylene glycol, ox bile extract, taurocholic acid.

4. NUTRIENTS AND DIETARY SUPPLEMENTS: alanine, arginine, ascorbic acid, aspartic acid, biotin, calcium carbonate, calcium citrate, calcium glycerophosphate, calcium oxide, calcium pantothenate, calcium phosphate, calcium pyrophosphate, calcium sulfate, carotene, choline bitartrate, choline chloride, copper gluconate, cuprous iodide, cysteine, cystine, ferric phosphate, ferric pyrophosphate, ferric sodium pyrophosphate, ferrous gluconate, ferrous lactate, ferrous sulfate, glycine, histidine, inositol, iron (reduced), isoleucine, leucine, linoleic acid, lysine, magnesium oxide, magnesium phosphate, magnesium sulfate, manganese chloride, manganese citrate, manganese gluconate, manganese glycerophosphate, manganese hypophosphite, manganese sulfate, manganous oxide, mannitol, methionine, methionine hydroxy analogue, niacin, niacinamide D-pantothenyl alcohol, phenylalanine, potassium chloride, potassium glycerophosphate, potassium iodide, proline, pyridoxine hydrochloride, riboflavin, riboflavin-5-phosphate, serine, sodium pantothenate, sodium phosphate, sorbitol, thiamine hydrochloride, thiamine mononitrate, threonine, tocopherols, tocopherol acetate, tyrosine, valine, vitamin A, vitamin A acetate, vitamin A palmitate, vitamin B12, vitamin D2, vitamin D3, zinc sulfate, zinc gluconate, zinc chloride, zinc oxide, zinc stearate.

5. SEQUESTRANTS: calcium acetate, calcium chloride, calcium citrate, calcium diacetate, calcium gluconate, calcium hexametaphosphate, calcium phosphate. monobasic, calcium phytate, citric acid, dipotassium phosphate, disodium phosphate, isopropyl citrate, monoisopropyl citrate, potassium citrate, sodium acid phosphate, sodium citrate, sodium diacetate, sodium gluconate, sodium hexametaphosphate, sodium metaphosphate, sodium phosphate, sodium potassium tartrate, sodium pyrophosphate, sodium pyrophosphate, tetra, sodium tartrate, sodium thiosulfate, sodium tripolyphosphate, stecaryl citrate, tartaric acid.

6. STABILIZERS: acacia (gum arabic), agar-agar, ammonium alginate, calcium alginate, carob bean gum, chondrus extract, ghatti gum, guar gum, potassium alginate, sodium alginate, sterculia (or karaya) gum, tragacanth.

7. ADDITIVES: acetic acid, adipic acid, aluminum ammonium sulfate, aluminum potassium sulfate aluminum sodium sulfate, aluminum sulfate, ammonium bicarbonate, ammonium carbonate, ammonium hydroxide, ammonium phosphate, ammonium sulfate, bees wax, bentonite, butane, caffeine, calcium carbonate, calcium chloride, calcium citrate, calcium gluconate, calcium hydroxide, calcium lactate, calcium oxide, calcium phosphate, caramel, carbon dioxide, carnauba wax, citric acid, dextrans, ethyl formate, glutamic acid, glutamic acid hydrochloride, glycerin, glyceryl monostearate, helium, hydrochloric acid, hydrogen peroxide, lactic acid, lecithin, magnesium carbonate, magnesium hydroxide, magnesium oxide, magnesium stearate, malic acid, methylcellulose, monoammonium glutamate, monopotassium glutamate, nitrogen, nitrous oxide, papain, phosphoric acid, potassium acid tartrate, potassium bicarbonate, potassium carbonate, potassium citrate, potassium hydroxide, potassium sulfate, propane, propylene glycol, rennet, silica aerogel, sodium acetate, sodium acid pyrophosphate, sodium aluminum phosphate, sodium bicarbonate, sodium carbonate, sodium citrate, sodium carboxy-methylcellulose, sodium caseinate, sodium citrate, sodium hydroxide, sodium pectinate, sodium phosphate, sodium potassium tartrate, sodium sesquicarbonate, sodium tripolyphosphate, succinic acid, sulfuric acid, tartaric acid, triacetin, triethyl citrate.

8. SYNTHETIC FLAVORING SUBSTANCES: acetaldehyde, acetoin, aconitic acid, anethole, benzaldehyde, N-butyric acid, d- or l-carvone cinnamaldehyde, citral, decanal, diacetyl, ethyl acetate, ethyl butyrate, ethyl vanillin, eugenol, geraniol, geranyl acetate, glycerol tributyrate limonene, linalool, linalyl acetate, l-malic acid, methyl anthranilate, 3-methyl-3-phenyl glycidic acid, ethyl ester, piperonal, vanillin.

II. Indicator Carriers

In at least one additional embodiment of a carrier, of the present disclosure, the carrier comprises an indicator compound capable of binding to and/or reacting with a target to produce an indicator signal. The target in an exemplary embodiment may be a diagnostic marker, such as the presence of glucose or glucose in excess of a defined threshold, the presence of one or more glycosylated protein related to diabetes or pre-diabetes, the presence of cancer (or pre-cancer) markers, and the presence of cardiac (or pre-cardiac) markers.

A. Indicators

The indicator compound in an exemplary embodiment of a carrier according to the present disclosure may be any compound, chemical, or biological component which may interact with a target or byproduct of a target. For example, an indicator compound may comprise an antibody, a reactive chemical compound, a labeled molecule, or any combination thereof. Antibodies used in an embodiment of the present disclosure may be monoclonal or polyclonal and derived from any species (e.g. human, rat, mouse, rabbit, pig). Further, indicator molecules may be aptamers, proteins, peptides, small organic molecules, natural compounds (e.g. steroids), non-peptide polymers, MHC multimers (including MHC-dextramers, MHC-tetramers, MHC-pentamers and other MHC-multimers), or any other molecules that specifically and efficiently bind to other molecules are also marker molecules.

Labeled molecules, for use as indicator compounds, may be any molecule that absorbs, excites, or modifies radiation, such as the absorption of light (e.g. dyes and chromophores) and the emission of light after excitation (fluorescence from flurochromes). Additionally, labeled molecules may have an enzymatic activity, by which it catalyzes a reaction between chemicals in the near environment of the labeling molecules, producing a signal which include production of light (chemiluminescence) or precipitation of chromophors, dyes, or a precipitate that can be detected by an additional layer of detection molecules.

Fluorescence labels may produce the presence of light at a single wavelength, or a shift in wavelengths. Exemplary fluorescent labels may include:

Fluor dyes, Pacific Blue™, Pacific Orange™, Cascade Yellow™;

AlexaFluor®(AF); o AF405, AF488 AF500, AF514, AF532, AF546, AF555, AF568, AF594, AF610, AF633, AF635, AF647, AF680, AF700, AF710, AF750, AF800;

Fluorescein (Flu) or any derivate of that, ex. FITC (fluorescein isothiocyanate) Cy—Dyes o Cy2, Cy3, Cy3.5, Cy5, Cy5.5, Cy7 Fluorescent Proteins; o RPE(R-phycoerythrin), PerCp, APC(Allophycocyanin); other of phycobillin containing proteins, e.g. phycobiliprotein o Green fluorescent proteins (GFP);

GFP and GFP derivated mutant proteins; BFP1CFP, YFP, DsRed, T1, Dimer2, mRFP1, MBanana, mOrange, dTomato, tdTomato, mTangerine, mStrawberry, mCherry Tandem dyes: o RPE-Cy5, RPE-Cy5.5, RPE-Cy7, RPE-AlexaFluor® tandem conjugates;

RPE-Alexa610, RPE-TxRed o APC-Aleca600, APC-Alexa610, APC-Alexa750, APC-Cy5, APC-Cy5.5 Multi fluorochrome assemblies o Multiple fluorochromes attached to a polymer molecule, such as a peptide/protein, Dex, or poly-sacceride. o Any combination of the fluorescent dyes involving in generation of FRET;

(Fluorescence resonance energy transfer) based techniques, Multiple fluorochromes associated or coupled to a polymeric molecule, or consisting of polymeric residues, Ionophors; ion chelating fluorescent probes or Probes that change wavelength when binding a specific ion, such as calcium;

Probes that change intensity when binding to a specific ion, such as calcium; and Combinations of fluorochromes on the same marker. The marker is not identified by a single fluorochrome but by a code of identification being a specific combination of fluorochromes, as well as inter related ratio's of intensities.

B. Target

The target of an exemplary indicator compound of the present disclosure may be any diagnostic marker or diagnostic condition for a disease state (or pre-disease state) of an individual. For example, the disease state may be diabetes, pre-diabetes, cardiac disease, pre-cardiac conditions, cancers of any stage and type, or pre-cancerous conditions. Specifically, the target may be the presence, or level of, glucose found in saliva for diabetes. Alternately, the target may be the presence, or level of, glycosylated proteins, such as advanced glycosylation end products. Further, the target may be the presence or level of cardiac markers, such as Creatine kinase-MB (CK-MB), myoglobin, homocysteine, C-reactive protein (CRP), troponin T (cTnT), and troponin I (cTnI). Moreover, the target may be the presence of cancer markers, such as Cancer Antigen 125, Cancer Antigen 15.3, Cancer Antigen 19.9, Prostate specific antigen, Carcinoembryonic Antigen, Alpha Feto-Protein, Epidermal growth factor receptor, Kallikrein 3, Vascular endothelial growth factor A (VEGF), Calcitonin, Chromogranin A, Gastrin, S100 alpha chain, Somatostatin, Thyroglobulin, V-erb-b2, cyckub-dependent kinase inhibitor 1 (p21), Breast Cancer Antigen 1 and 2 (BRCA1 and 2), MutL homolog 1 (MLH1), MutS homolog 2 (MSH2), MutS homolog 6 (MSH6), and postmeiotic segregation increased 1 and 2 (PMS1 and 2). Moreover, the target may be the presence or level of any diagnostic marker included herein.

C. Indicator Signal

The indictor signal in at least one embodiment of the present disclosure may comprise any detectable signal, including but not limited to, color change, fluorescence, and chemical/structural change of the target (and/or indicator compound) so as to be amenable to reacting with a secondary detection marker. Further, the detection of a signal may involve a secondary reactive molecule.

D. Glucose

In an embodiment of the present disclosure, glucose may be detected through an indicator rinse by a chemical or enzymatic method. Exemplary embodiments of this method may include alkaline copper reduction, alkaline ferricyanide reduction, glucose oxidase, and/or hexokinase.

In an exemplary embodiment of an indicator rinse of the present disclosure, the rinse may further comprise one or more additional component as described herein. These additional components may include stabilizing agents, as well as GRAS components (such as those listed herein).

E. Glycosylated Hemoglobin

In an embodiment of the present disclosure, glycated Hemoglobin A1c (HbA1c) may be detected through any known method for the detection of HbA1c or fragments thereof, such as high pressure liquid chromatography, immunoassays, and an indicator rinse by a chemical or enzymatic method. In an exemplary embodiment of an indicator rinse of the present disclosure, the rinse may further comprise one or more additional component as described herein. These additional components may include stabilizing agents, as well as GRAS components (such as those listed herein).

F. Cancer Antigen 19-9

In an embodiment of the present disclosure, cancer antigen 19-9 (CA 19-9) may be detected through any known method for the detection of CA 19-9 or fragments thereof, such as high pressure liquid chromatography, immunoassays, and an indicator rinse by a chemical or enzymatic method. In an exemplary embodiment of an indicator rinse of the present disclosure, the rinse may further comprise one or more additional component as described herein. These additional components may include stabilizing agents, as well as GRAS components (such as those listed herein).

III. Diagnostic Marker Detection

In an embodiment of the present disclosure, a diagnostic marker susceptible to degradation or alteration by a destructive component may be detected through any known method, including, but not limited to, high pressure liquid chromatography, immunoassays, and an indicator rinse by a chemical or enzymatic method. Further, the detection may be conducted in a micro well, deep well, microarray, microfluidic device, high throughput screen, or any applicable diagnostic device.

A. Rapid Diagnostic

Detection of a diagnostic marker may be conducted according to a rapid detection system of the present disclosure. Turning to FIG. 1A, a detection platform 100 may comprise a platform 102 having a plurality of test wells 104, where each well is capable of containing a plurality of test spots 106. The plurality of test wells 104 may include at least 2, at least 4, at least 8, at least 16, at least 32, at least 64, or at least 256 wells. The plurality of tests spots 106 may include at least 2, at least 4, at least 8, at least 16, at least 32, or at least 64 test spots 106. Further, each of the plurality of test spots 106 may comprise one or more diagnostic marker or control marker.

An embodiment of detection platform 100 may further be sized and shaped to allow for automated detection and analysis of a diagnostic or control marker. In at least one embodiment, the detection system 100 may comprise an identifier 108, such as a barcode or Radio-frequency identification (RFID) tag, to allow for the identification of the detection system 100 and data collected from the analysis of test spots 106.

Further, detection platform 100 may be comprised of any applicable material sufficient to house or define test wells 104. Exemplary embodiments of applicable materials for detection platform 100 may be a polymer, glass, metal, quartz, nylon, silica-based material, resin, or combination thereof. Further, embodiments of test wells 104 may include not only a depression defined or housed by platform 102, but may also include a defined area or region of the platform 102 (such as may be found on a microarray based platform).

Turning to FIG. 1B, at least one embodiment of detection system 150 of the present disclosure is shown. An exemplary embodiment of detection system 150 comprises an embodiment of detection platform 100, a detection device 120 capable of determining a binding characteristic between a detection agent and a diagnostic marker on the detection platform 100, and a computer processor 130 coupled to a computer database 135 and to the detection device 120. In at least embodiment, the computer processor 130 controlling the detection device 120 is able to (1) determine the binding characteristic of a detection agent to a diagnostic agent, (2) compare the binding characteristic among each of a plurality of samples tested, (3) generate a binding report using the compared binding characteristics, and deliver the binding report to a recipient or external computer (not shown) in communication with the computer processor 130.

A binding characteristic as used herein may include any measurement of the attraction (or repulsion) of two molecules (such as a detection agent and a diagnostic marker).

Detection system 100 may also comprise an embodiment of a bead-based system of the present disclosure having at least one bead type. For example, a dual bead system may be used wherein at least one bead type is magnetic or paramagnetic. These beads may also be bound to a carrier protein with a conjugated hapten. Further, the beads may have an analyte capture monoclonal antibody reagent bound to it. Additionally, the beads, in at least one embodiment, do not retain their magnetic properties when removed from a magnetic field. In at least one embodiment, the beads may be Europium micro-particles. The sizes of the Europium micro-particles may be varied as needed to accommodate the method of detection used.

Figure 2:
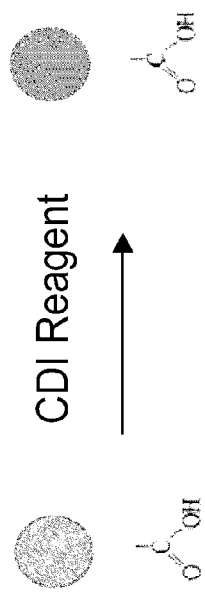
FIGS. 2-4 shows a diagram of a method of producing a bead system, according to at least one embodiment of the present disclosure.
Figure 2:
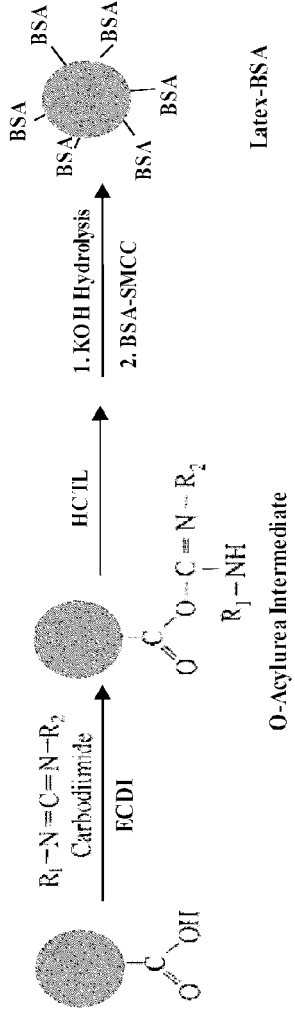
Figure 2:
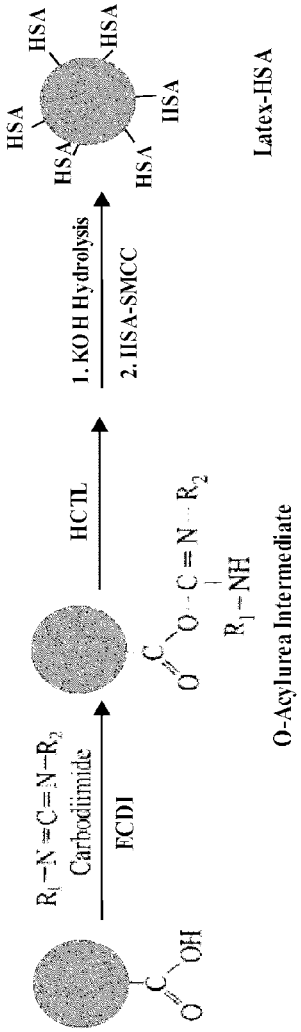
Figure 3:
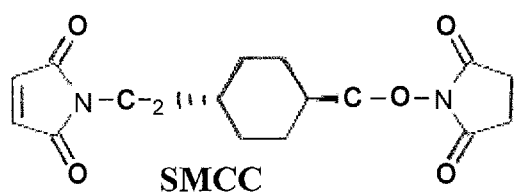
Figure 4:
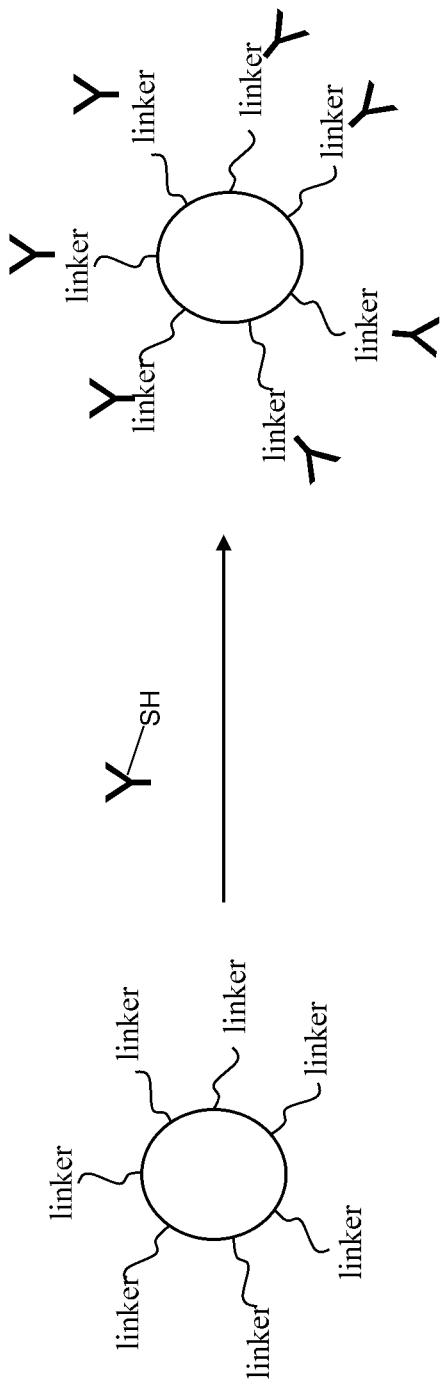

At least one embodiment of a bead based system may comprise a latex particle (See FIGS. 2-4). The latex particle according to at least one embodiment may be a Carboxylate modified latex (CML) bead. Further, an exemplary embodiment of a bead may include bovine serum albumin (BSA) and/or human serum albumin (HSA). Additionally, an embodiment of a bead based system of the present disclosure may include a linker coupled to HSA and/or BAS. The linker according to an embodiment, may comprise a maleimide compound. At least one exemplary embodiment of a maleimide compound may be Succinimidyl 4-[N-Maleimidomethyl] Cyclohexane-1-Carboxylate (SMCC) or N-Hydroxysuccinimide-activated hexa(ethylene glycol)undecane Thiol (NHS). Moreover, at least one exemplary embodiment of a bead based system may further comprise an antibody linked to maleimide on the bead. Accordingly, at least one embodiment of the bead based system comprises a latex particle coupled to BAS or HSA, maleimide coupled to BAS or HSA, and an antibody coupled to maleimide.

The latex particle, according to at least one embodiment may be in a size range from about 0.02 μm to about 7.0 μm.

Figure 5:
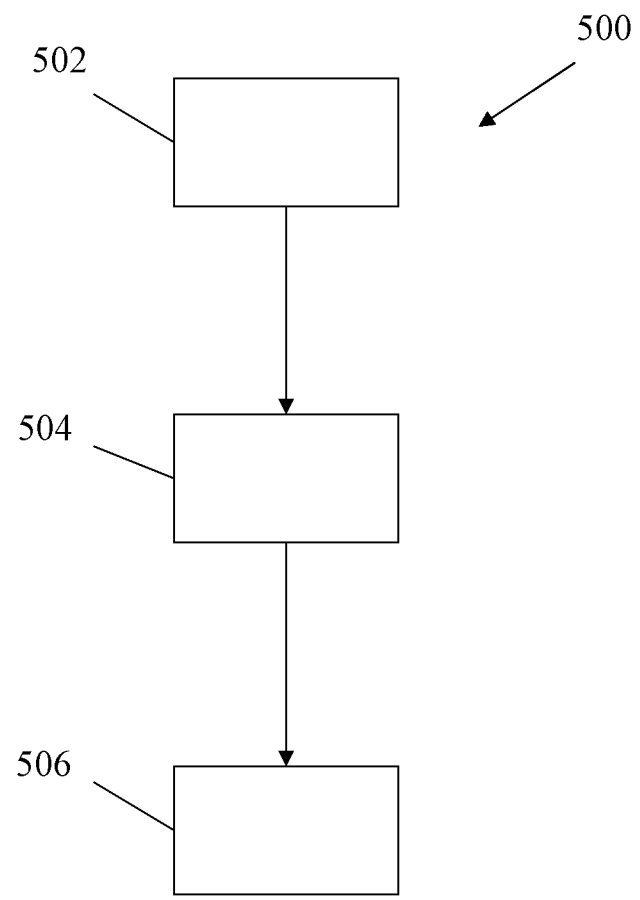
FIG. 5 shows a flowchart of a method for creating a bead system, according to at least one embodiment of the present disclosure.

Turning to FIG. 5, at least one at least one method 500 of coupling an antibody to a bead comprises the step 502 of modifying an embodiment of a bead (such as a latex bead/particle) with BSA or HAS, wherein the BSA or HSA may further comprise a maleimide containing molecule, such as SMCC or NHS. Additionally, an embodiment of the method 500 may further comprise the step 504 of attaching a diagnostic marker binding agent (such as an antibody) to the bead. Step 504 of attaching the diagnostic marker binding agent to the bead may be accomplished through binding the diagnostic marker binding agent to maleimide. Further, method 500 may also comprise the step 506 of attaching one or more stabilizing agent to an embodiment of a bead. Additionally, while an embodiment of method 500 may use latex beads for attachment of a maleimide containing molecule and/or a stabilizing agent, alternate embodiments of the bead may comprise silicon, a polymer, or other applicable materials.

According to at least one embodiment of the present disclosure, one or more stabilizing agent may be attached or adsorbed to any one of an embodiment of a detection platform, test strip, microchip, or microfluidic device.

B. Test Strip

Figure 6A:
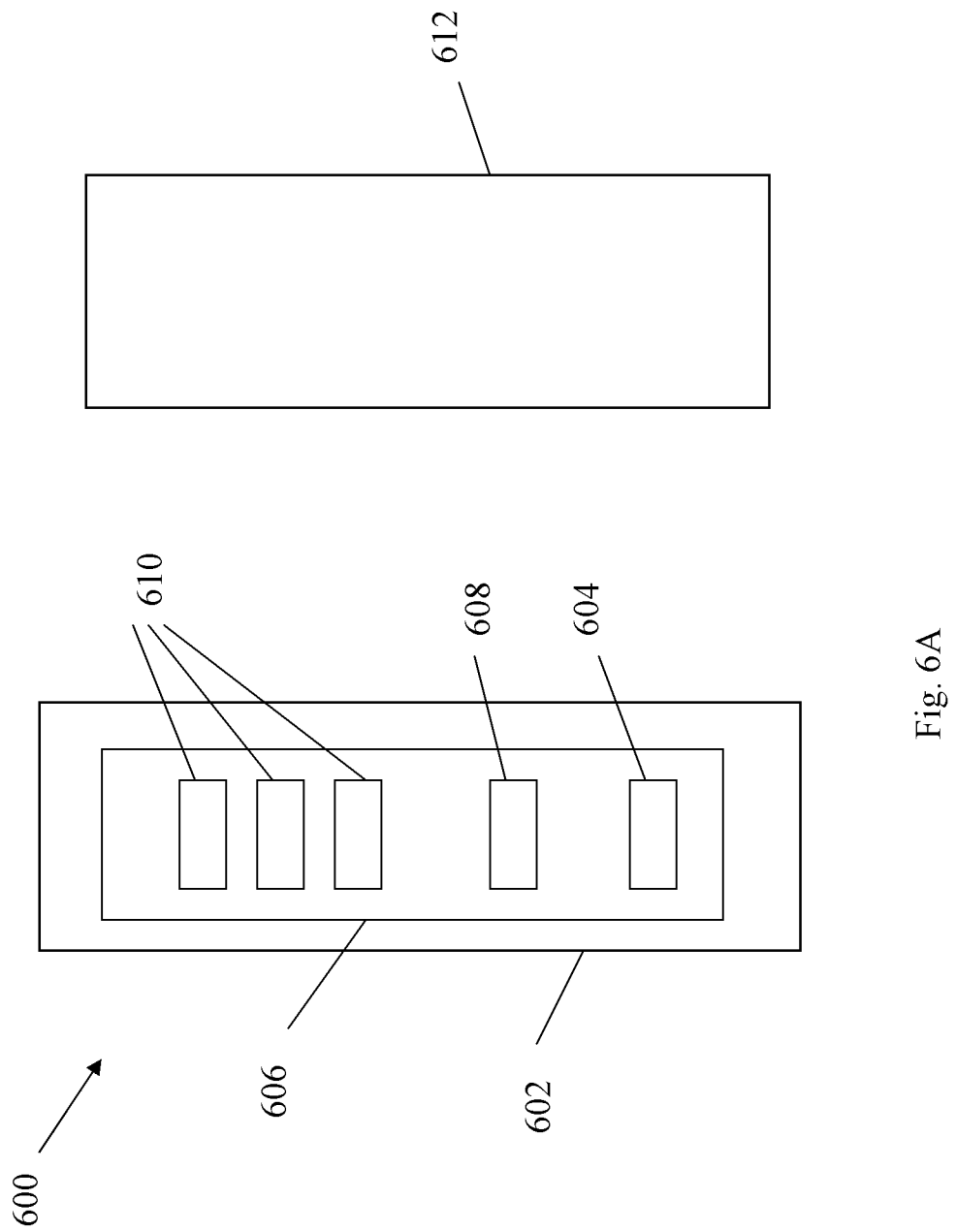
FIGS. 6A and B show a diagram of a test strip, according to at least one embodiment of the present disclosure.
Figure 6B:
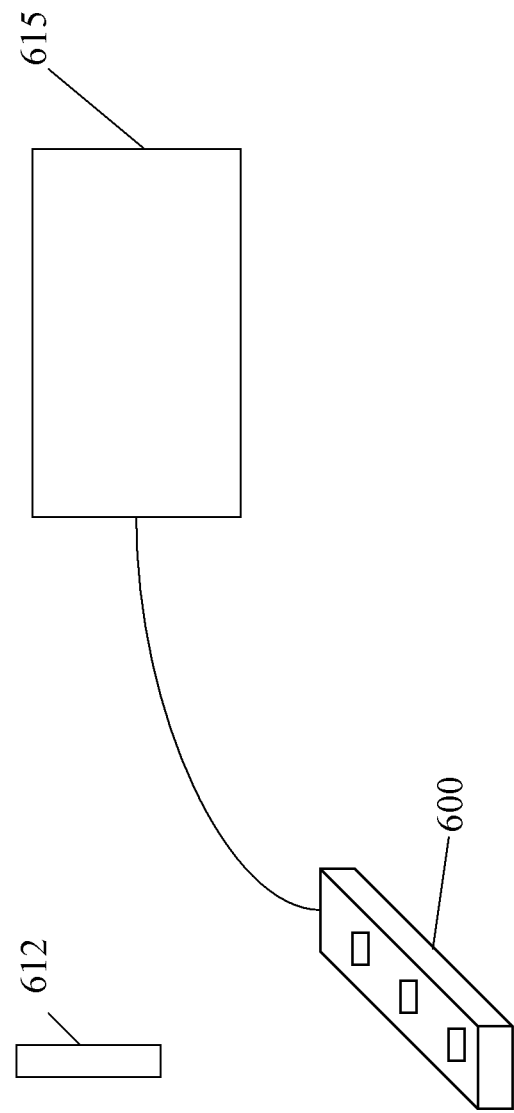
FIG. 6C show a diagram of a microarray, according to at least one embodiment of the present disclosure.
FIG. 6D shows a diagram of a microfluidic system, according to at least one embodiment of the present disclosure.

Turning to FIGS. 6A and B, exemplary embodiments of a diagnostic testing device 600 are described. An exemplary embodiment of diagnostic testing device 600 comprises housing structure 602 which comprises a collection chamber 604 capable of receiving body fluid, at least one membrane strip 606 in fluid communication with collection chamber 604, an immunoassay-based fingerprint acquisition pad 608 in fluid communication with the collection chamber 604, and a plurality of reaction zones 610 which may allow the visual display of the presence of a predetermined diagnostic marker. For example, reaction zone 610 may in an exemplary embodiment be capable of displaying a characteristic of the predetermined diagnostic marker, such as the presence of, the concentration of, or a concentration above or below a predetermined value for the predetermined diagnostic agent.

In an exemplary embodiment of diagnostic testing device 600, diagnostic testing device 600 further comprises a fluid collector 612 which is operable to collect body fluid from a subject, and wherein the fluid collector is capable of supply collected body fluid to collection chamber 604.

Exemplary embodiments of test strip 606 may comprise any material capable of adsorbing or attaching a stabilizing agent and may bind a diagnostic marker. Further, exemplary embodiments of test strip 606 may comprise compositions comprising a polyvinyl chloride-silica combination, nitrocellulose, or any suitable synthetic, resinous material. At least one embodiment, housing 602 is capable of reducing the exposure of the test strip 606 at sites other than the collection chamber 604 to foreign material. Test strip 606 in at least one embodiment may be capable of interfacing with an analysis device 615. The analysis device 615 in an exemplary embodiment may be capable of measuring the level of the predetermined diagnostic marker in the sample.

Figure 6C:
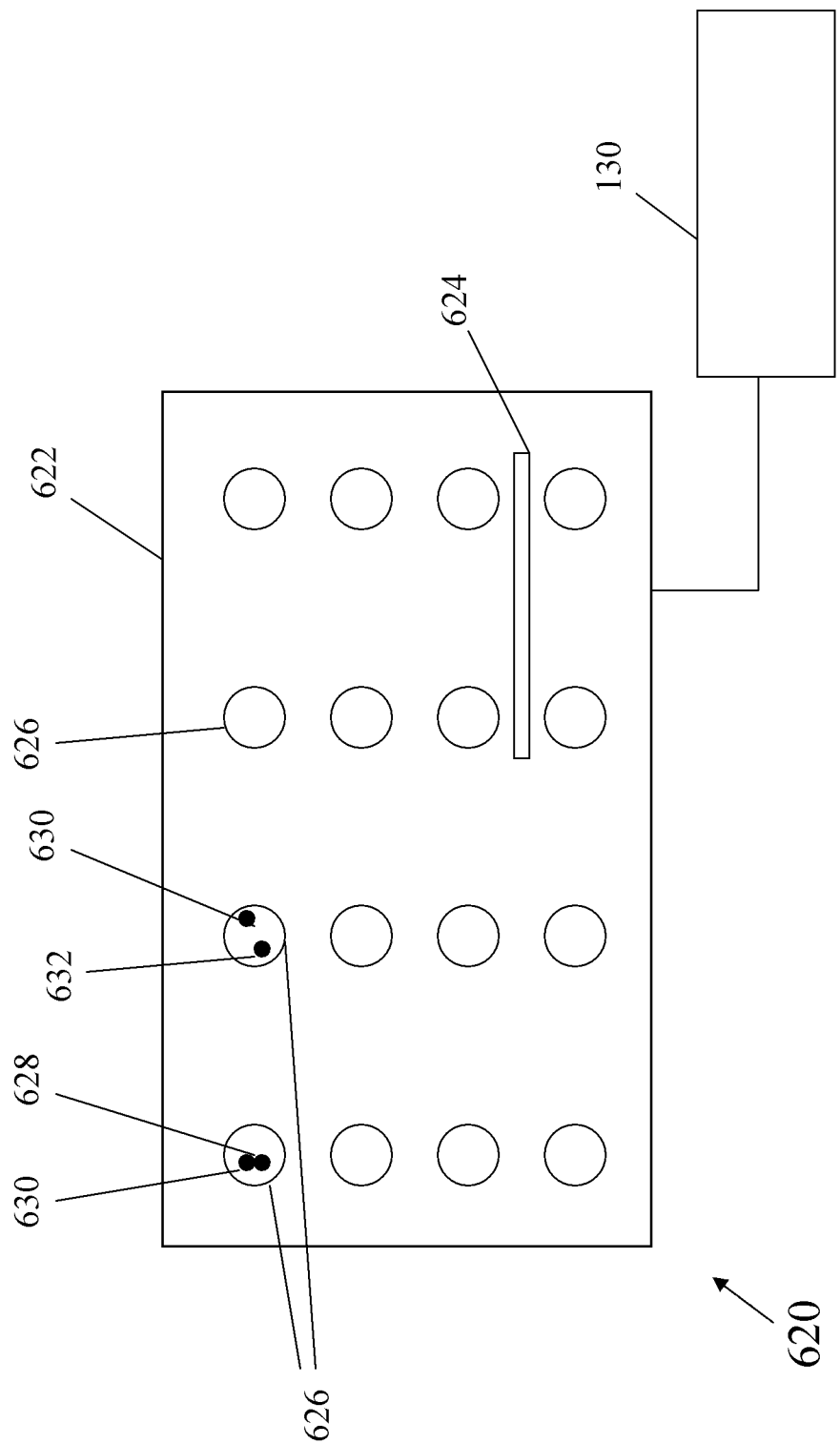

Turning to FIG. 6C, an exemplary embodiment of a microarray system 620 is described. An exemplary embodiment of microarray system 620 may comprise a microarray product 622 having a microarray identifier 624, and a plurality of microarray sites 626, a control microarray product 628 located on at least one microarray site 626 and bound to microarray product 622, and operably connected to a computer processor 130 for providing information regarding the identification and concentration of markers on the microarray product 622 based on the microarray identifier 624. Additionally, microarray product 622 may further comprise, in at least one embodiment, an embodiment of a stabilization agent 630 located on at least one microarray site 626 and bound to microarray product 622. Further, microarray product 622 may comprise one or more diagnostic marker 632 located on at least one microarray site 626 and bound to microarray product 622. Moreover, microarray system 620, in at least one embodiment, may further comprise a microarray detector 634 operable to detect a signal from at least one of the control microarray product 628 and/or diagnostic marker 632.

A microchip or microarrays may refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In an embodiment, the microarray may be prepared and used at least according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), all of which are incorporated herein in their entirety by reference.

Figure 6D:
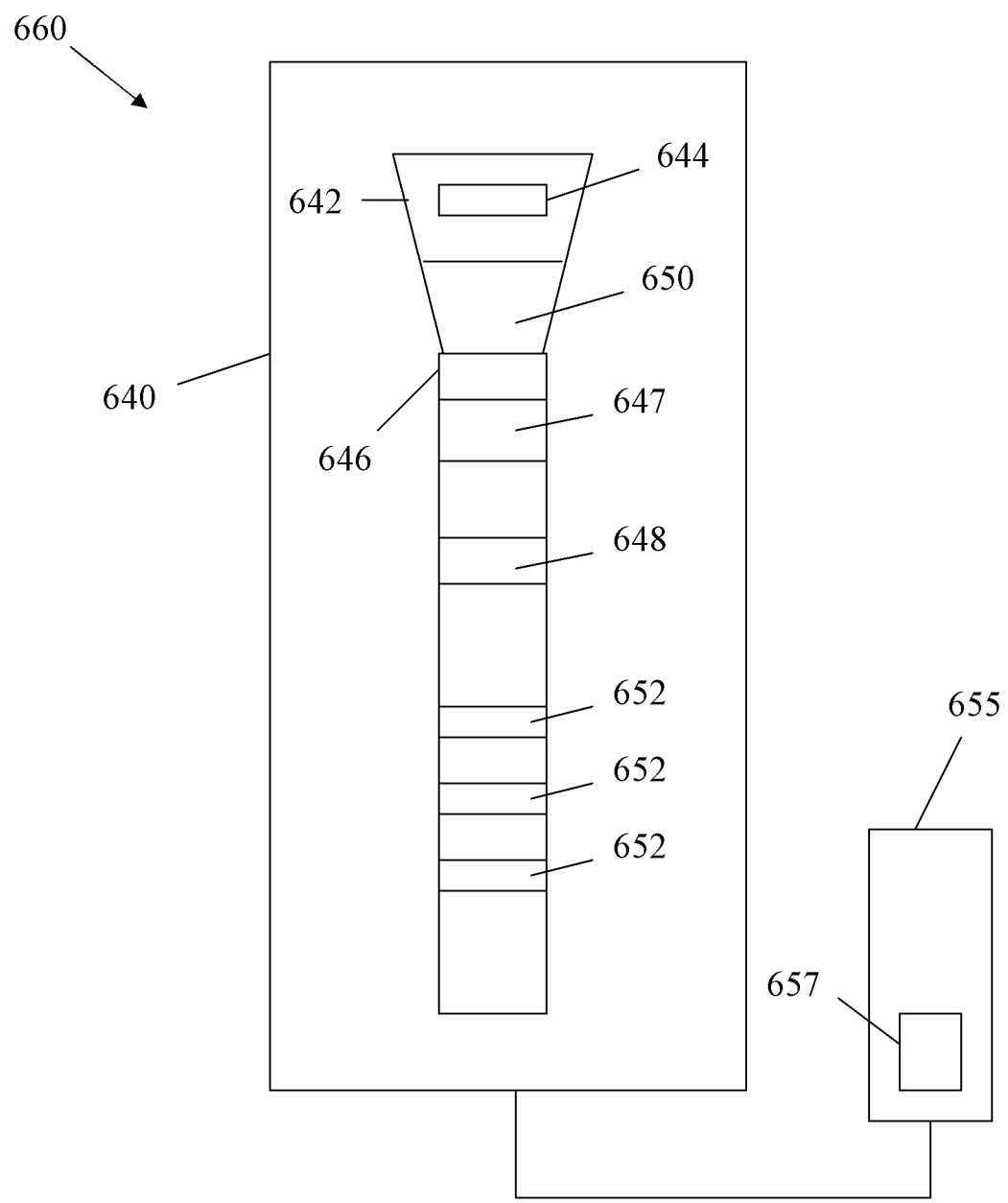

Turning to FIG. 6D, an exemplary embodiment of microfluidic device 640 is described. An embodiment of microfluidic device 640 comprises a sample reservoir 642 for receiving a body fluid (or other fluid sample) through a sample input 644, where the sample reservoir 642 is fluidly connected to a detector array 646. Additionally, in at least one embodiment of microfluidic device 640, detector array 646 comprises a reaction site 647 and a results display 648. Moreover, an exemplary embodiment of microfluidic device 640 may further comprise a filter device 650 capable of separating at least one unwanted component from a fluid sample and fluidly coupled between sample reservoir 642 and detector array 646. Detector array 646 may also, in at least one embodiment comprise a control reagent display 652, where at least one control reagent may be visually detected.

Further, microfluidic device 640 may also, in at least one embodiment, be able to couple to a processor 655. Processor 655 may be able to compare at least one reading, such as from results display 648 or control reagent display 652 from an embodiment of microfluidic device 640 to at least one additional stored reading on a computer database 657 of the processor 655. An embodiment of microfluidic system 660 of the present disclosure, may comprise one or more microfluidic device 640 operationally coupled to a processor 655.

Embodiments of microfluidic devices 640, which may also be referred to as "lab-on-a-chip" systems, biomedical microelectro-mechanical systems (bioMEMs), or multicomponent integrated systems, are exemplary kits/systems for analyzing polynucleotide regions. Such systems may miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more polynucleotide region of the present disclosure. Exemplary microfluidic devices 640 may comprise a pattern of microchannels designed onto a glass, silicon, quartz, or plastic wafer included on a microchip. The movements of the samples may be controlled by electric, electroosmotic or hydrostatic forces applied across different areas of the microchip to create functional microscopic valves and pumps with no moving parts. Varying the voltage can be used as a means to control the liquid flow at intersections between the micro-machined channels and to change the liquid flow rate for pumping across different sections of the microchip.

In at least one embodiment of a microarray or microfludic device 640, the microarray or microfluidic device may comprise one or more stabilizing agent capable of reducing the degradation of a predefined diagnostic marker. For example, a stabilizing agent may be incorporated onto the surface of the microarray device, and/or on at least one part of the microfluidic device.

IV. Methods of Biomarker Stabilization

Figure 7:
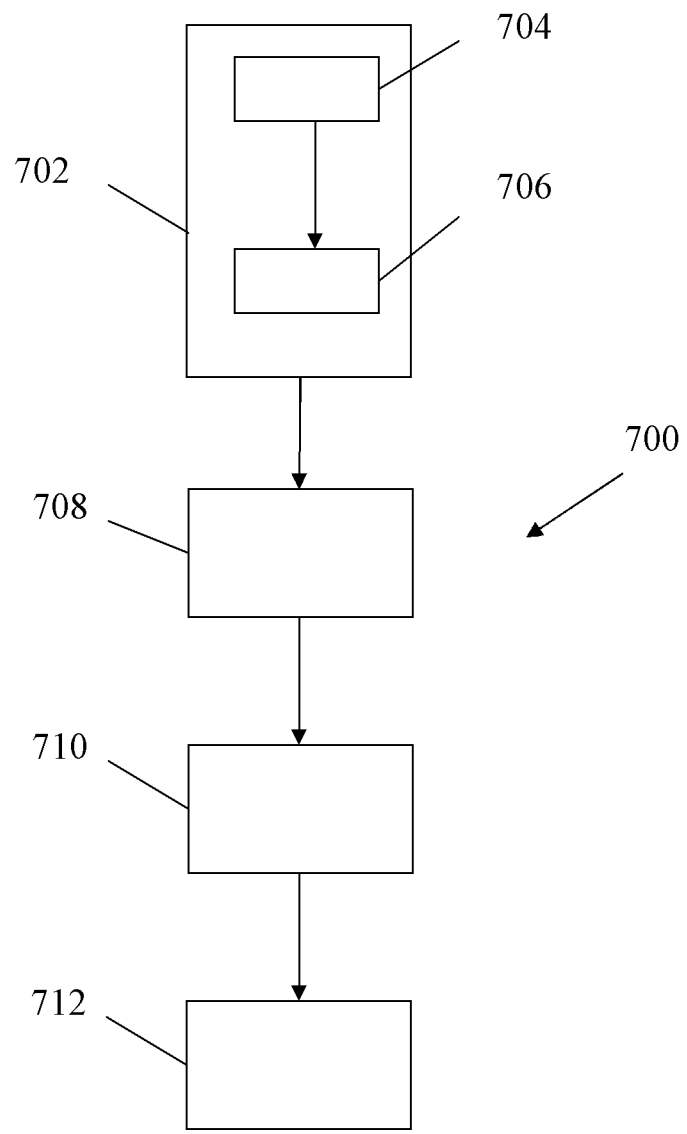
FIG. 7 shows a flowchart of a method of stabilizing diagnostic markers, according to at least one embodiment of the present disclosure.

In at least one embodiment of a method for stabilizing biomarkers, as described in FIG. 7, the method 700 comprises the step 702 of mixing a body fluid with an embodiment of a stabilizing agent. Optionally, the step of mixing a body fluid with a stabilizing agent may comprise the step 704 of introducing the stabilizing agent into the patient, such as through the oral cavity, so that the stabilizing agent mixes with the bodily fluid, and the step 706 of retrieving a body fluid comprising a stabilized diagnostic marker. In an additional exemplary embodiment of a method of stabilizing a diagnostic marker, the method comprises the step 708 of isolating a body fluid having a diagnostic marker, the step 710 of treating the body fluid with an embodiment of a carrier, such as a rinse, gum, or beverage, as described herein, and the step 712 of analyzing the diagnostic marker. Isolation of the body fluid may occur through any customary mechanism, including, but not limited to, rinsing, swabbing, suction, collection, and lavage. Further, the rinse in an exemplary embodiment of a method 700 of the present disclosure, may be ingested to stabilize a diagnostic marker present in the bodily fluid, such as in urine, semen, anal secretions, and vaginal secretions.

The step 702 of mixing a body fluid with a carrier may occur prior to, or after isolation step 708 of the body fluid. As an exemplary embodiment, a rinse may be used to rinse the mouth. Afterwards, the rinse containing the treated body fluid may be collected by spitting, suction, or other means. Alternately, expirated saliva may be mixed with a rinse to treat the saliva ex vivo. Similar treatment of body fluids may be performed with any type of body fluid.

In analyzing the treated body fluid, the diagnostic marker may be analyzed through any known means. Optionally, the analysis of the treated body fluid may include the separation of solid materials from soluble materials through means such as filtration, or by centrifugation. Analysis of the treated body fluid may use any appropriate technique, such as western blot analysis, Enzyme-Linked Immunosorbent Assay (ELISA), protein activity assays, reverse transcription polymerase chain reaction (RT-PCR), microarray, high pressure liquid chromatography, or any comparable assay to determine a characteristic of the diagnostic marker. Such an analysis, in an exemplary embodiment, may be of a modified product, a cleavage product, or cleavage pattern, of a diagnostic marker.

In an exemplary embodiment of the analyzing step 712, the treated body fluid may be placed in contact with an embodiment of a test strip, such as a nitrocellulose strip, prior to detection with an appropriate probe specific for the diagnostic marker. The nitrocellulose strip may be designed to trap or filter particulates in the body fluid. This may reduce or eliminate potential contaminants or other substances in the oral fluid that would otherwise reduce the signal to noise ration during the detection step. A probe (such as an antibody) with affinity to the diagnostic marker may be affixed or immobilized to a specific location on the nitrocellulose membrane for detection of the analyte. Utilizing standard principles of immunoassay detection (or nucleotide detection), the signal generated may be visible to the eye or detectable by an instrument.

Figure 8:
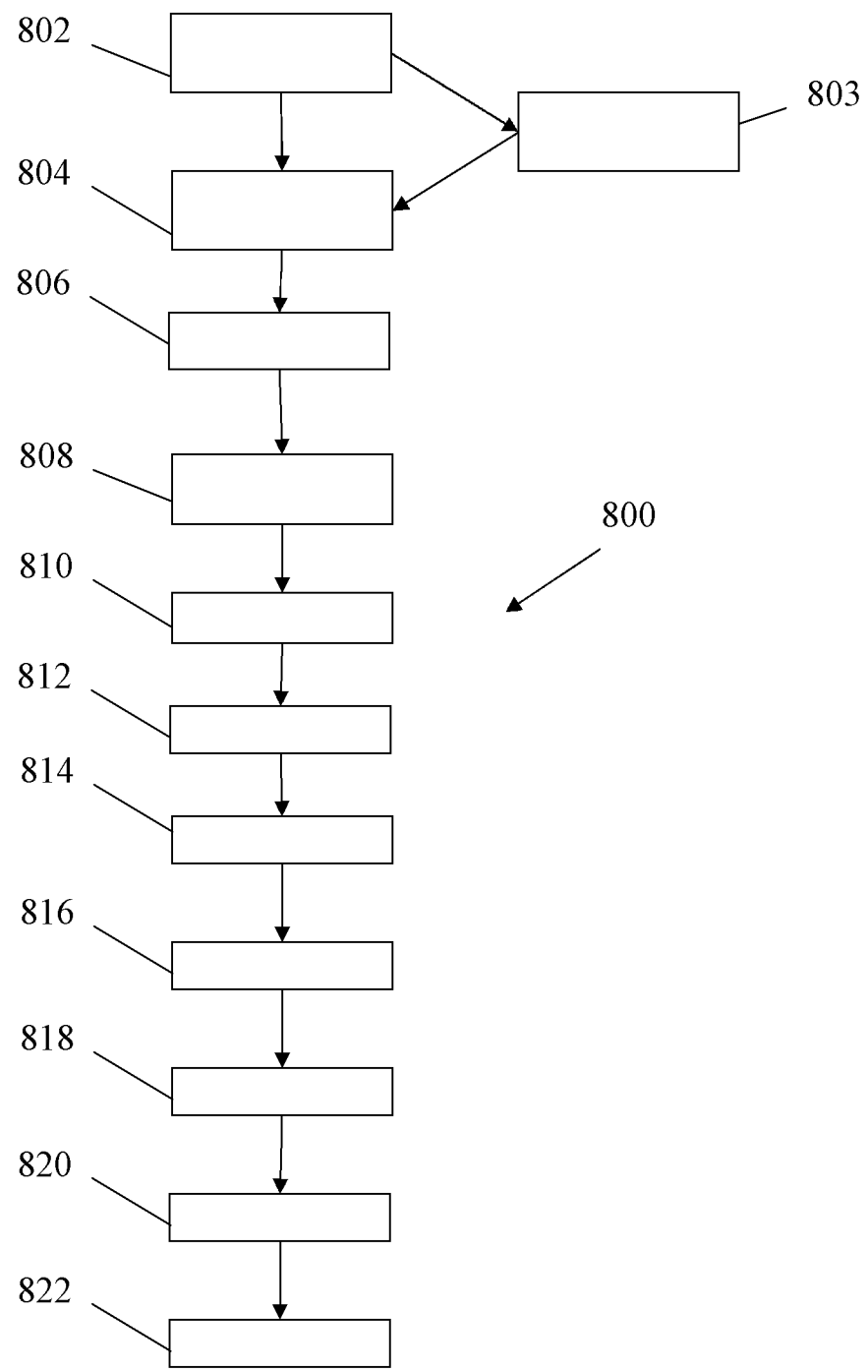
FIG. 8 shows a flowchart of a method analyzing a diagnostic markers, according to at least one embodiment of the present disclosure.

In an exemplary embodiment of a method of analyzing a stabilized diagnostic marker of the present disclosure as depicted in FIG. 8, the method 800 comprises the step 802 of operating a system for the detection of a diagnostic marker in a body fluid, where the system comprises a diagnostic device having a plurality of test wells each capable of containing at least one diagnostic marker binding agent, and a detection device capable of interacting with diagnostic device, wherein the detection device is capable of detecting an interaction between the at least one diagnostic marker binding agent and a diagnostic marker. Following step 802, the sample of bodily fluid may be diluted in step 803 with a reagent which may contain an embodiment of stabilizing agent as described herein. At least one embodiment of method 800 further comprises the steps of: contacting 804 a sample of a bodily fluid with at least one diagnostic marker binding agent, incubating 806 the contacted sample in the test well at a first temperature for a pre-determined period of time. The step 804 of contacting of the sample of bodily fluid with at least one diagnostic marker binding agent may be accomplished through a magnetic field applied to the test well.

In at least one embodiment of method 800, the first temperature may be at room or at body temperature (such as about 22° C. or about 37° C.). The pre-determined period of time may, for example, be between five and fifteen minutes. The incubated and contacted sample may then be removed in step 808 from the plurality of test wells, and the test wells analyzed in step 810 to detect a binding event with the detection device. Alternately, a stabilizing agent may be incubated with the diagnostic marker binding agent (also referred to as a detection agent) prior to introduction of a bodily fluid. In at least one embodiment of the method, each diagnostic marker binding agent may have a different monoclonal antibody designed to bind a specific hapten molecule.

Following the detection of a characteristic of a treated diagnostic marker (the results of which may be termed a "profile" such as a "cancer profile"), the characteristic may in step 812 be compared to a standard value to determine the presence or absence of a disease state. The characteristic determined may be an activity level, the concentration of the diagnostic marker, or a particular modification, such as glycosylation or methylation.

Optionally, an embodiment of the method 800 may further comprise the step 814 of customizing a detection method through screening of applicable pre-clinical samples through a database of stabilizing agents/cocktails. Further, an embodiment of method 800 of diagnostic marker detection may further comprise the step 816 of comparing a level or characteristic (such as a predictable degradation products) of a diagnostic agent with a library of known characteristics. Moreover, an exemplary embodiment of method 800 may additionally comprise the step 818 of determining a diagnosis of a disease state using the compared characteristic. In at least one embodiment, a method of diagnostic marker detection may be automated, and capable of detecting at least about ten thousand samples in a twenty-four hour period. Method 800 in at least one embodiment, may be at least partially completed by a computer processor. Additionally, the processor may be in communication with at least one more processor and/or a computer database. For instance, in at least one embodiment of method 800, most of the steps of the method may be completed with or monitored by a computer processor. Moreover, method 800, in at least one embodiment, may use a computer processor to perform additional step 820 of generating a report by using a comparison of determined characteristics (such as a binding report where a comparison is performed of binding characteristics), and step 822 of delivering the report to a recipient (such as a user, or secondary processor).

A method of biomarker stabilization may, in an exemplary embodiment, be used to diagnose a particular disease state or condition of a patient. For example, a disease state or condition as used with this method may include one or more of Acid-Base Disorders, Acidosis and Alkalosis, Acidosis/Alkalosis, Acute inflammatory demyelinating polyneuropathy, Acute myocardial infarct, Addison's Disease, Adrenal Insufficiency, Adrenal Insufficiency & Addison's Disease, Alcohol dependence, Alcoholism, Allergies, Alzheimer's Disease, Anemia, Angina Pectoris, Anthrax, Arthritis, Asthma, Atypical Pneumonia, Autoimmune Disorders, Autoimmune thyroiditis, Avian flu, Benign Prostatic Hyperplasia, Benign Prostatic Hypertrophy, Bioterrorism Agents, Bleeding Disorders, Bone Marrow Disorders, Breast Cancer, Cardiovascular Disease, Celiac Disease, Cervical Cancer, Chlamydia, Chronic Fatigue and Immune Dysfunction Syndrome, Chronic Fatigue Syndrome, Chronic thyroiditis, Colon Cancer, Community-Acquired Pneumonia, Congestive Heart Failure, Conn's Syndrome, Cushing's Syndrome, Cystic Fibrosis, Degenerative Joint Disease, Diabetes, Diarrhea, Diffuse thyrotoxic goiter, Diseases of the Pancreas, Disseminated lupus erythematosus, Double pneumonia, Down Syndrome, Encephalitis, Endocrine Syndromes, Endocrine System and Syndromes, Epilepsy, Fibromyalgia, Flu, Folate Deficiency, Fungal Infections, Genital Herpes, Gonorrhea, Gout, Gouty arthritis, Graves' Disease, Guillain-Barre Syndrome, Influenza H1N1, Hashimoto's Thyroiditis, Healthcare-Associated Pneumonia, Heart Attack, Heart Attack and Acute Coronary Syndrome, Heart Disease, Hemochromatosis, Hepatitis, Herpes, Herpes Zoster, High blood pressure, Hospital-Acquired Pneumonia, Human Immunodeficiency Virus, Human Papillomavirus, Hypercoagulable Disorders, Hypersensitivity, Hypertension, Hyperthyroidism, Hypothyroidism, Infectious Arthritis, Infectious polyneuritis, Infertility, Inflammatory Bowel Disease, Influenza, Influenza A, Influenza B, Insulin Resistance, Jaundice, Juvenile Rheumatoid Arthritis, Kidney and Urinary Tract Function, Disorders, and Diseases, Kidney Disease, Landry's ascending paralysis, Lead Poisoning, Leukemia, Liver Disease, Lobar pneumonia, Lower Respiratory Tract Infection, Lung Diseases, Lupus, Lupus erythematosus, Lyme Disease, Lymphoma, Malnutrition, Meningitis, Meningitis and Encephalitis, Menopause, Metabolic Syndrome, Metabolic Syndrome/Syndrome X, Multiple Myeloma, Multiple Sclerosis, Myeloproliferative Disorders, Myocardial infarct, Neural Tube Defects, Nontuberculous Mycobacteria, Osteoarthritis, Osteoporosis, Ovarian Cancer, Pancreatic Cancer, Pancreatic Diseases, Pancreatic Insufficiency, Pancreatitis, Pelvic Inflammatory Disease, Peptic Ulcer, Pituitary Disorders, Pneumonia, Polycystic ovarian syndrome, Pregnancy, Primary hyperaldosteronism, Prostate Cancer, Proteinuria, Rheumatoid Arthritis, Septic Arthritis, Sexually Transmitted Diseases, Sexually transmitted infections, Shingles, Sickle Cell Anemia, Sickle Cell Disease, Sjögren's Syndrome, Staph Wound Infections, Staph Wound Infections and Methicillin Resistant *Staphylococcus aureus*, Stein-Leventhal syndrome, Stroke, Swine flu, Syphilis, Systemic Lupus Erythematosus, Testicular Cancer, Thalassemia, Thyroid Diseases, Travelers' Diseases, Trichomonas, Tuberculosis, Types of Liver Disease, Urinary Tract Infection, Venereal diseases, Vitamin B12 and Folate Deficiency, Vitamin B12 Deficiency, Vitamin K Deficiency, Walking pneumonia, West Nile Virus, Wilson's Disease, Wound and Skin Infections.

V. Methods to Determine Efficacy and Specificity of a Therapeutic

Figure 9:
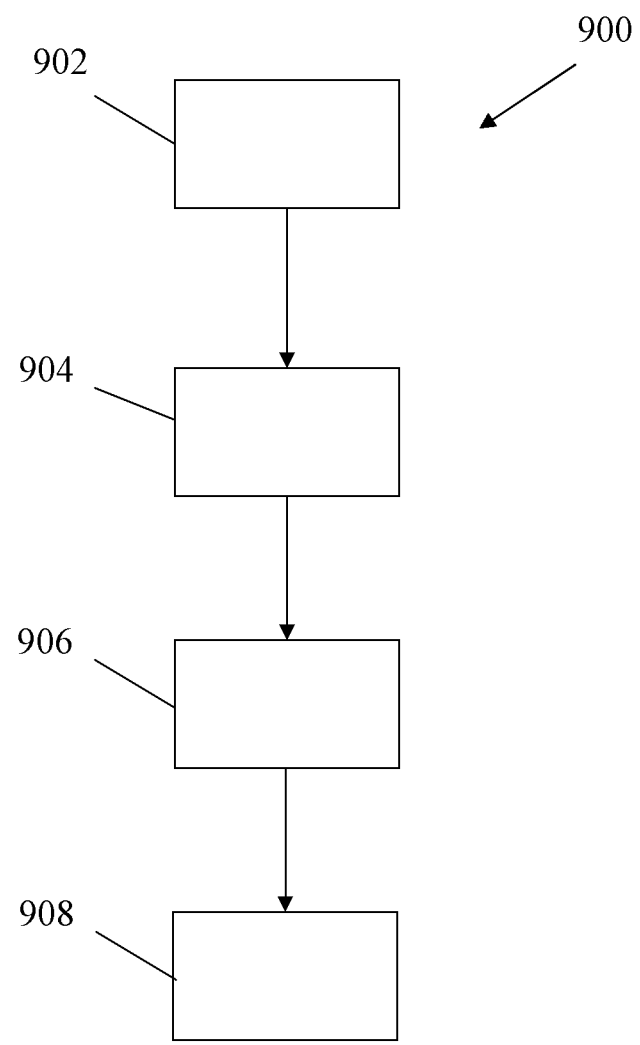
FIG. 9 shows a flowchart of a method of improving biomarker availability, according to at least one embodiment of the present disclosure.

According to FIG. 9, in at least one embodiment of the present disclosure, a method 900 of improving biomarker availability is described and shown. Method 900 comprises the step 902 of contacting a diagnostic marker from a patient with a stabilization agent, the step 904 of introducing a therapeutic agent to the diagnostic marker and the stabilization agent, and the step 906 of analyzing the interaction of the therapeutic agent with the diagnostic marker to determine a therapeutic profile, such as the binding affinity of the agent to the diagnostic marker. Further, method 900 may also comprise the step 908 of comparing the therapeutic profile with at least one other therapeutic profile to determine a stabilizing impact from the stabilizing agent on the diagnostic marker. Step 908 of comparing a plurality of therapeutic profiles may be performed using a computer processor and may further utilize a computer database of previously documented therapeutic profiles. Moreover, in an exemplary embodiment of method 900, the step 902 of contacting a diagnostic marker with a stabilization agent may be repeated with a plurality of different stabilization agents and/or therapeutic agents. Additionally, the therapeutic profile may be used to determine a therapeutic course to treat the patient.

Figure 10:
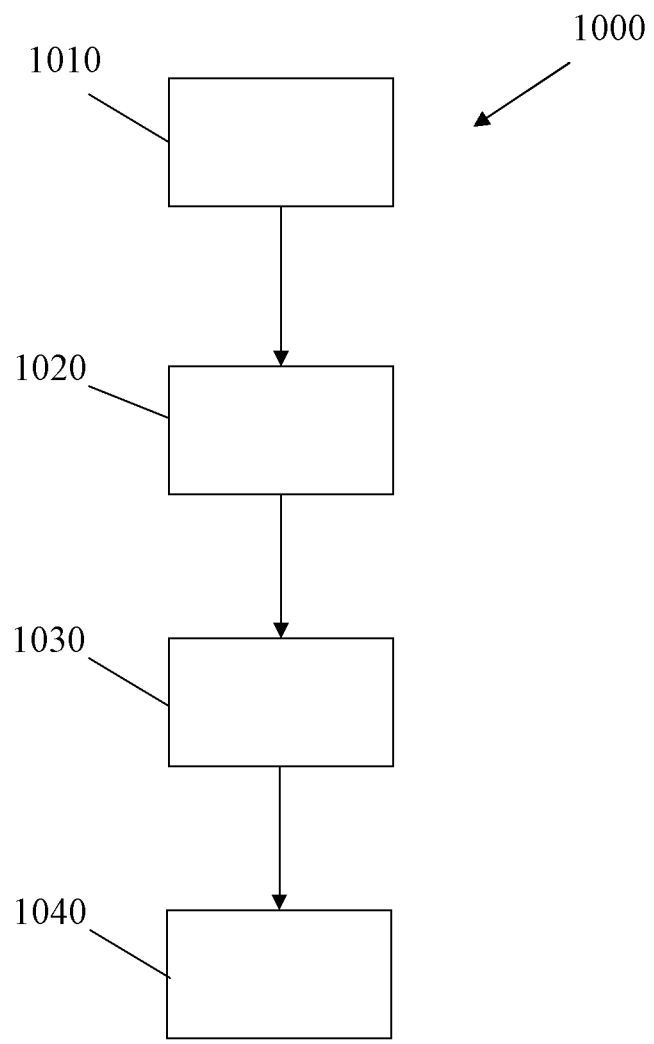
FIG. 10 shows a flowchart of a method of identifying diagnostic markers of a disease state, according to at least one embodiment of the present disclosure.

In FIG. 10, a method of identifying diagnostic markers of a disease state is shown. Method 1000, according to at least one embodiment, comprises the step 1010 of contacting a bodily fluid from a subject having a disease state with a stabilizing agent, and the step 1020 of analyzing the stabilized bodily fluid to determine at least one property of a diagnostic agent, to create a disease state profile. An exemplary embodiment of method 1000 may further comprise the step 1030 of comparing the disease state profile with a profile generated in a like manner from a subject not having the disease state, and the step 1040 of generating a disease state identifier panel from the compared disease state profile. In at least one embodiment of method 1000, the disease state is cancer. Exemplary embodiments of cancer may include at least bladder cancer, lung cancer, breast cancer, melanoma, colon and rectal cancer, non-hodgkin lymphoma, endometrial cancer, pancreatic cancer, kidney (renal cell) cancer, prostate cancer, leukemia, and thyroid cancer. In at least one embodiment of method 1000, the subject is currently receiving treatment with an original treatment agent, and the disease state profile may be compared with a disease profile of the same subject while receiving a different treatment agent, a different concentration of the same treatment agent, or at an earlier point of time.

Figure 11:
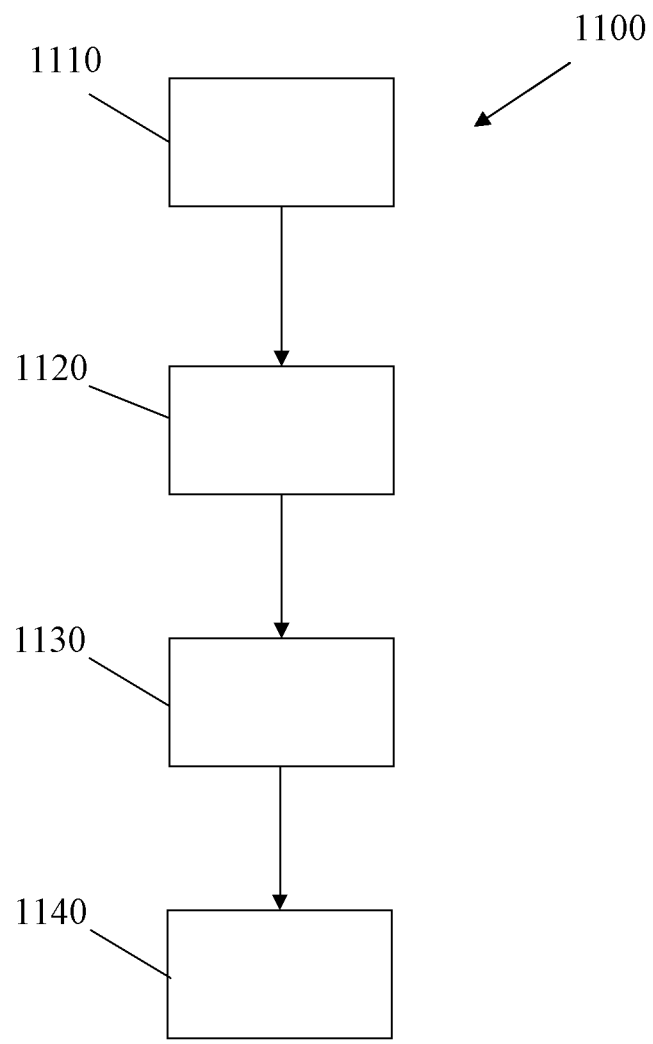
FIG. 11 shows a flowchart of a method for screening biomarkers, according to at least one embodiment of the present disclosure.

In FIG. 11, an exemplary embodiment of a method for screening biomarkers is described. Method 1100 comprises the steps of (a) contacting 1110 a cell from a subject having a disease state with a stabilizing agent, (b) incubating 1120 the stabilized cell with a therapeutic compound, and (c) analyzing 1130 the incubated cell for at least one diagnostic marker to create a marker profile. Optionally, method 1100 may further comprise the step 1140 of comparing the marker profile with at least one additional marker profile to determine the efficacy of the therapeutic compound.

Figure 12:
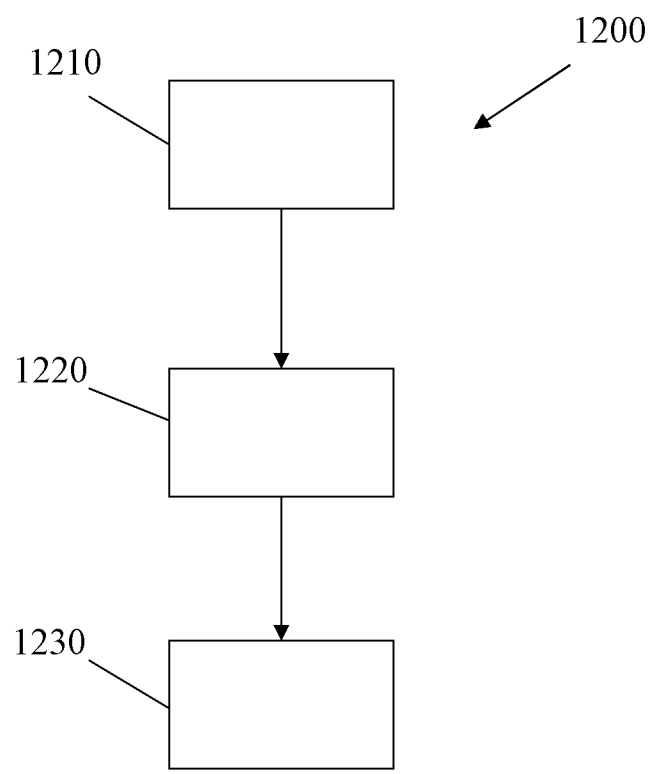
FIG. 12 shows a flowchart of a method of stabilizing diagnostic markers, according to at least one embodiment of the present disclosure.

In at least one method of stabilizing diagnostic markers of the present disclosure, as shown in FIG. 12, the method 1200 comprises the step 1210 of measuring the level of diagnostic marker in a subject with a disease state, the step 1220 of treating the subject with a therapeutic agent, and the step 1230 of determining the post-treatment level of diagnostic marker. Wherein the step 1210 of measuring the level of diagnostic marker includes the step of incubation of the diagnostic marker with a stabilization agent.

In at least one embodiment of method 900, 1000, 1100, or 1200, the method may be used with a device as described herein, such as an embodiment of diagnostic system 100, test strip 600, a microarray 640, or microfluidic device 660, any of which may also be performed in conjunction with a computer processor.

VI. Computational Analysis

In at least one embodiment of the systems, methods, and devices of the present disclosure, a computer processor and a database may be used in or during the system, method, or device. An exemplary embodiment of a system framework comprising at least one computer processor and at least one database, as may be used in the embodiments of the present disclosure is shown in FIG. 13.

In at least one embodiment, a result from a diagnostic method may be compared using a computer processor to at least one additional result from the diagnostic test, and/or to a result stored on a database. Such a comparison, in at least one embodiment of the present disclosure, may reveal the stabilizing agent with a greater effect on the binding characteristic, may allow for the diagnosis of a disease state or health/lifestyle characteristic. Further, such a comparison, in at least one embodiment, may be used to develop, confirm, or modify a therapeutic treatment of a patient having a disease state or health/lifestyle characteristic.

Figure 13:
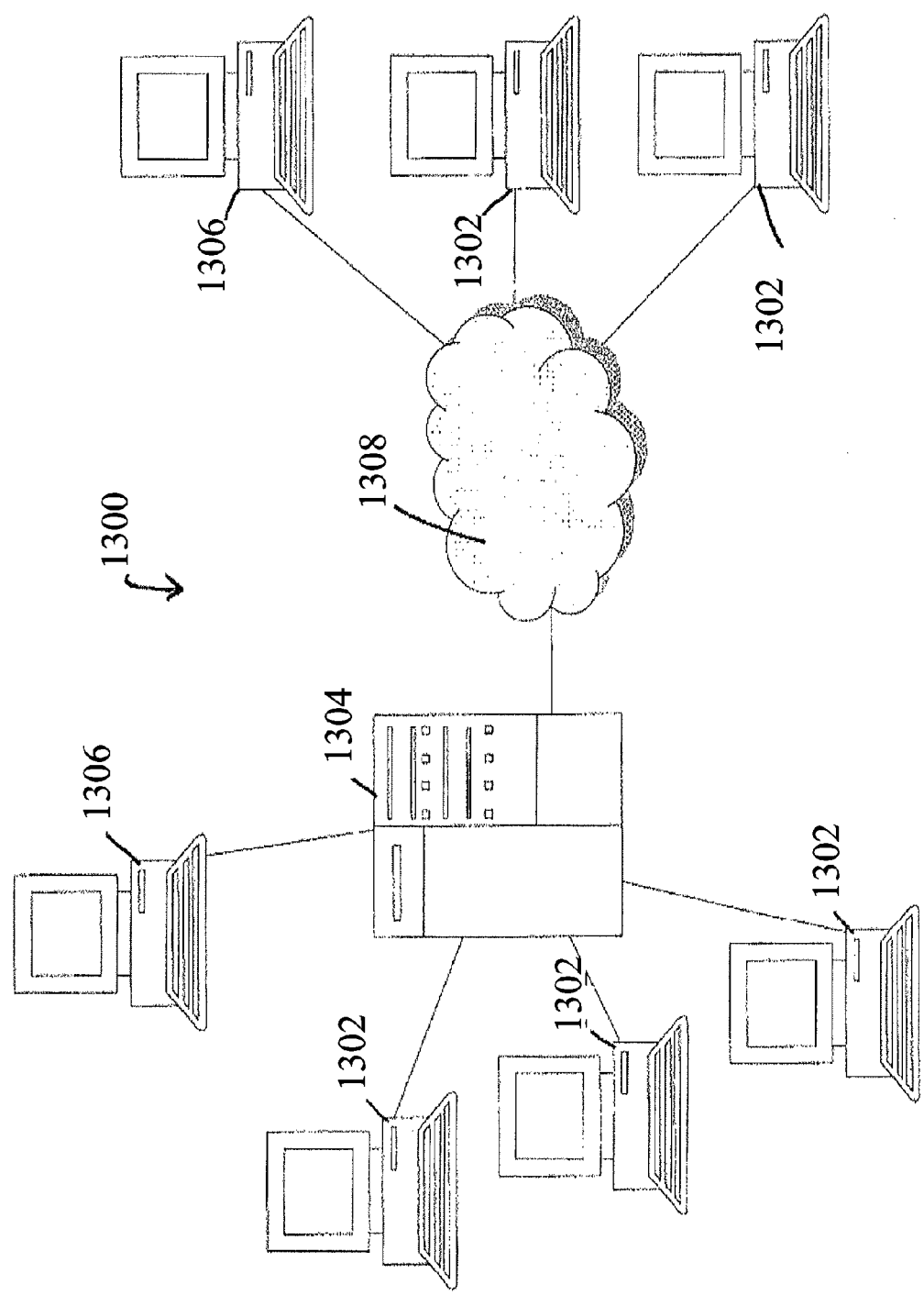
FIG. 13 shows a an exemplary system framework, according to at least one embodiment of the present disclosure.

As shown in exemplary system framework 1300 shown in FIG. 13, one or more user computers 1302 may be operably connected to a system server 1304. A user computer 1302 may be a computer, computing device, or system of a type known in the art, such as a personal computer, mainframe computer, workstation, notebook computer, laptop computer, hand-held computer, wireless mobile telephone, personal digital assistant device, and the like.

One or more administrator computers 1306 may also be operably connected to system server 1304 including through a network 1308 such as the Internet. Administrator computers 1306, similar to user computers, may be computers, computing devices, or systems of a type known in the art, such as personal computers, mainframe computers, workstations, notebook computers, laptop computers, hand-held computers, wireless mobile telephones, personal digital assistant devices, and the like. In addition, user computers and administrator computers may each comprise such software (operational and application), hardware, and componentry as would occur to one of skill of the art, such as, for example, one or more microprocessors, memory, input/output devices, device controllers, and the like. User computers and administrator computers may also comprise one or more data entry means (not shown in FIG. 13) operable by a user of client computer and/or an administrator computer, such as, for example, a keyboard, keypad, pointing device, mouse, touchpad, touchscreen, microphone, and/or other data entry means known in the art. User computers and administrator computers also may comprise an audio display means (not shown in FIG. 13) such as one or more loudspeakers and/or other means known in the art for emitting an audibly perceptible output. The configuration of user computers and administrator computers in a particular implementation of one or more systems of the present disclosure is left to the discretion of the practitioner.

System server 1304 may comprise one or more server computers, computing devices, or systems of a type known in the art. System server 1304 may comprise server memory. System server 1304 may comprise one or more components of solid-state electronic memory, such as random access memory. System server 1304 may also comprise an electromagnetic memory such as one or more hard disk drives and/or one or more floppy disk drives or magnetic tape drives, and may comprise an optical memory such as a Compact Disk Read Only Memory (CD-ROM) drive. System server 1304 may further comprise such software (operational and application), hardware, and componentry, as would occur to one of skill of the art, such as, for example, microprocessors, input/output devices, device controllers, video display means, and the like.

System server 1304 may comprise one or more host servers, computing devices, or computing systems configured and programmed to carry out the functions allocated to system server 1304. System server 1304 may be operated by, or under the control of, a "system operator," which may be an individual or a business entity. For purposes of clarity, System server 1304 is shown in FIG. 13 and referred to herein as a single server. System server 1304 need not, however, be a single server. System server 1304 may comprise a plurality of servers or other computing devices or systems connected by hardware and software that collectively are operable to perform the functions allocated to the various systems of present disclosure. Specifically, system server 1304 may be operable to be a web server, configured and programmed to carry out the functions allocated to a system server according to the present disclosure. Further, although user computers 1302 and administrator computers 1306 may be connected directly to system server 1304, these computers may be connected to system server 1304 through any suitable network, such as network 1308. Further, in one embodiment, the users need not be provided access to system server 1304, but instead the content posts from users are made by the user(s) and saved to one or more particular locations and the posts are accessed or harvested by the administrator or system automatically.

System server 1304 may be operably connected to the various user computers 1302 and/or an administrator computers 1306 by network 1308, which in an embodiment of the present disclosure comprises the Internet, a global computer network. However, network 1308 need not comprise the Internet. Network 1308 may comprise any means for electronically interconnecting system server 1304 and a user computer 1302 and/or an administrator computer 1306. Thus, it will be appreciated by those of ordinary skill in the art that the network 1308 may comprise the Internet, the commercial telephone network, one or more local area networks, one or more wide area networks, one or more wireless communications networks, coaxial cable, fiber optic cable, twisted-pair cable, the equivalents of any of the foregoing, or the combination of any two or more of the foregoing. In an embodiment where system server 1304 and user computer 1302 and/or an administrator computer 1306 comprise a single computing device operable to perform the functions delegated to both system server 1304 and user computer 1302 and/or an administrator computer 1306 according to the present disclosure, network 1308 comprises the hardware and software means interconnecting system server 1304 and user computer 1302 and/or an administrator computer 1306 within the single computing device. Network 1308 may comprise packet switched facilities, such as the Internet, circuit switched facilities, such as the public switched telephone network, radio based facilities, such as a wireless network, etc.

The various systems, methods, schema, ontologies, and architectures of the present disclosure may be used for purposes outside of the medical transcription field as referenced in the various examples cited herein. For example, the system for analyzing verbal records may comprise various components and relationships suitable for use in any number of areas where various experiences are utilized and processed, with feedback being fed back into system componentry to improve overall system outcomes. In addition, various components described herein may share a name (or a portion thereof) but have duplicative reference numbers, and therefore the descriptions for the various components should read in view of one another.

In addition, and regarding the various systems of the present disclosure, such systems may be operable, as desired by a user of such systems, to generate visual, electronic (video, audio, database, transcript, etc.), and/or printed reports, outputs, outcomes, and the like. Such exemplary outputs may be used for any number of purposes, and may be useful generally to "report" results, data, and/or knowledge contained within and generated from such systems. Furthermore, the disclosure of the present application further encompasses uses of the various methods, systems, architectures, etc., to perform various tasks in connection therewith.

EXAMPLES

Examples

1. α-Amylase Inhibition Saliva Screening Method

At least one assay used for the detection of α-amylases activity, as used herein includes the use of a chromagenic substrate, 2-chloro-p-nitrophenol linked to maltotriose. Enzymatic activity of α-amylase on the substrate yields 2-chloro-p-nitrophenol, which can be measured spectrophotometrically at 405 nm. The amount of α-amylase activity present in the experimental sample is directly proportional to the increase in absorbance at 405 nm.

For the assay, test compounds are mixed with saliva, prior to the addition of α-amylase substrate. The test compounds, such as GRAS materials, are prepared at a concentration of 5,000 ppm in distilled water. Following this preparation, 300 μl of α-amylase substrate (Salimetrics α-amylase Assay Kit) that has been pre-heated to 37° C. is added to 20 μl of the test compound. To initiate the assay, 10 μl of a dilute (3.5%) or full strength (100%) saliva solution is added to the mixture. Following the initiation, each mixture is measured at 1 minute intervals using a spectrophotometer (such as Molecular Devices M5 reader) at 405 nm. Temperatures of the mixtures are kept constant at 37° C. during the assay.

2. α-Amylase Inhibitor Assays.

Figure 14:
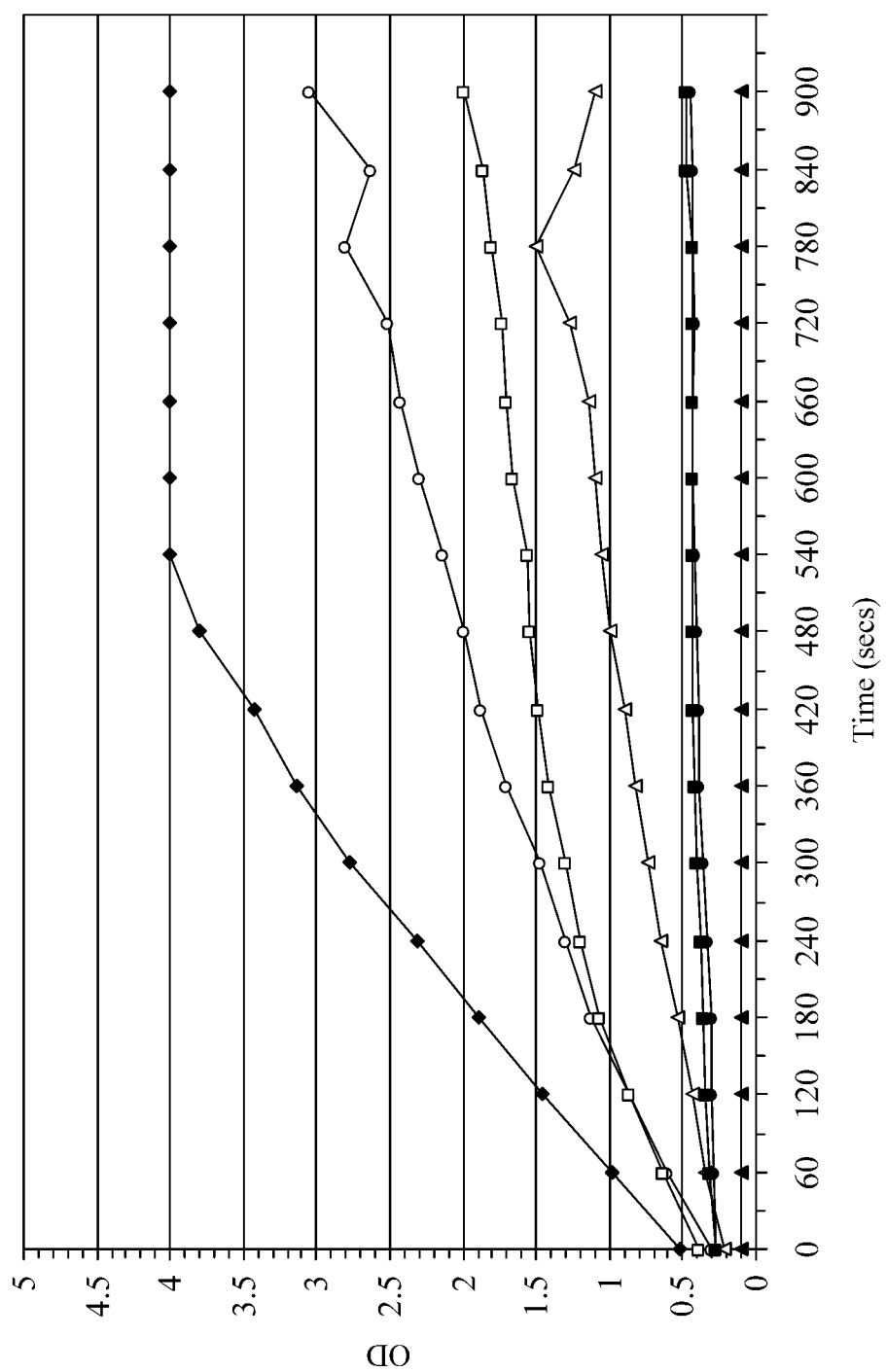
FIG. 14 shows a graphical depiction of α-amylase inhibition according to at least one embodiment of the present disclosure.

A series of GRAS compounds were tested using the α-amylase assay protocol described here. The tested compounds are included in Table I. From the screen of GRAS compounds, five compounds (CDI-030,034,036,037 and 042) were shown to have α-Amylase Inhibitor Activity in dilute (3.5%) saliva (See FIG. 14). Further details of these five compounds may also be seen in Table 4.

TABLE 4

| Time | | CDI-30 | CDI-34 | CDI-36 | CDI-37 | CDI-42 | 100% Saliva Control | 0% Amylase Control |
|---|---|---|---|---|---|---|---|---|
| 0 min | | 1.60 | 0.40 | 3.63 | 4.00 | 0.80 | 4.00 | 0.09 |
| | | 2.03 | 0.36 | 3.20 | 3.85 | 1.13 | 4.00 | 0.09 |
| | | 2.02 | 0.40 | 3.46 | 4.00 | 0.90 | 4.00 | 0.09 |
| | | 1.87 | 0.45 | 4.00 | 4.00 | 0.84 | 4.00 | 0.10 |
| | % CV | 10.67 | 9.13 | 9.42 | 1.85 | 16.35 | 0.00 | 1.84 |
| | Ave | 1.88 | 0.40 | 3.57 | 3.96 | 0.92 | 4.00 | 0.09 |
| | % Std | 46.96 | 10.04 | 89.29 | 99.08 | 22.93 | 100.00 | 2.34 |
| | % Inhibition | 53.04 | 89.96 | 10.71 | 0.92 | 77.07 | 0.00 | 97.66 |
| 5 min | | 4.00 | 0.49 | 4.00 | 4.00 | 1.65 | 4.00 | 0.09 |
| | | 4.00 | 0.50 | 4.00 | 4.00 | 2.15 | 4.00 | 0.09 |

TABLE 4-continued

| Time | | CDI-30 | CDI-34 | CDI-36 | CDI-37 | CDI-42 | 100% Saliva Control | 0% Amylase Control |
|---|---|---|---|---|---|---|---|---|
| | | 4.00 | 0.50 | 4.00 | 4.00 | 1.80 | 4.00 | 0.09 |
| | | 4.00 | 0.52 | 4.00 | 4.00 | 1.81 | 4.00 | 0.10 |
| | % CV | 0.00 | 2.32 | 0.00 | 0.00 | 11.31 | 0.00 | 2.79 |
| | Ave | 4.00 | 0.50 | 4.00 | 4.00 | 1.85 | 4.00 | 0.09 |
| | % Std | 100.00 | 12.61 | 100.00 | 100.00 | 46.24 | 100.00 | 2.36 |
| | % Inhibition | 0.00 | 87.39 | 0.00 | 0.00 | 53.76 | 0.00 | 97.64 |
| 15 min | | 4.00 | 0.53 | 4.00 | 4.00 | 2.37 | 4.00 | 0.09 |
| | | 4.00 | 0.61 | 4.00 | 4.00 | 2.38 | 4.00 | 0.10 |
| | | 4.00 | 0.54 | 4.00 | 4.00 | 2.25 | 4.00 | 0.09 |
| | | 4.00 | 0.56 | 4.00 | 4.00 | 2.17 | 4.00 | 0.10 |
| | % CV | 0.00 | 6.67 | 0.00 | 0.00 | 4.33 | 0.00 | 1.88 |
| | Ave | 4.00 | 0.56 | 4.00 | 4.00 | 2.29 | 4.00 | 0.09 |
| | % Std | 100.00 | 14.02 | 100.00 | 100.00 | 57.35 | 100.00 | 2.37 |
| | % Inhibition | 0.00 | 85.98 | 0.00 | 0.00 | 42.65 | 0.00 | 97.64 |

Figure 15:
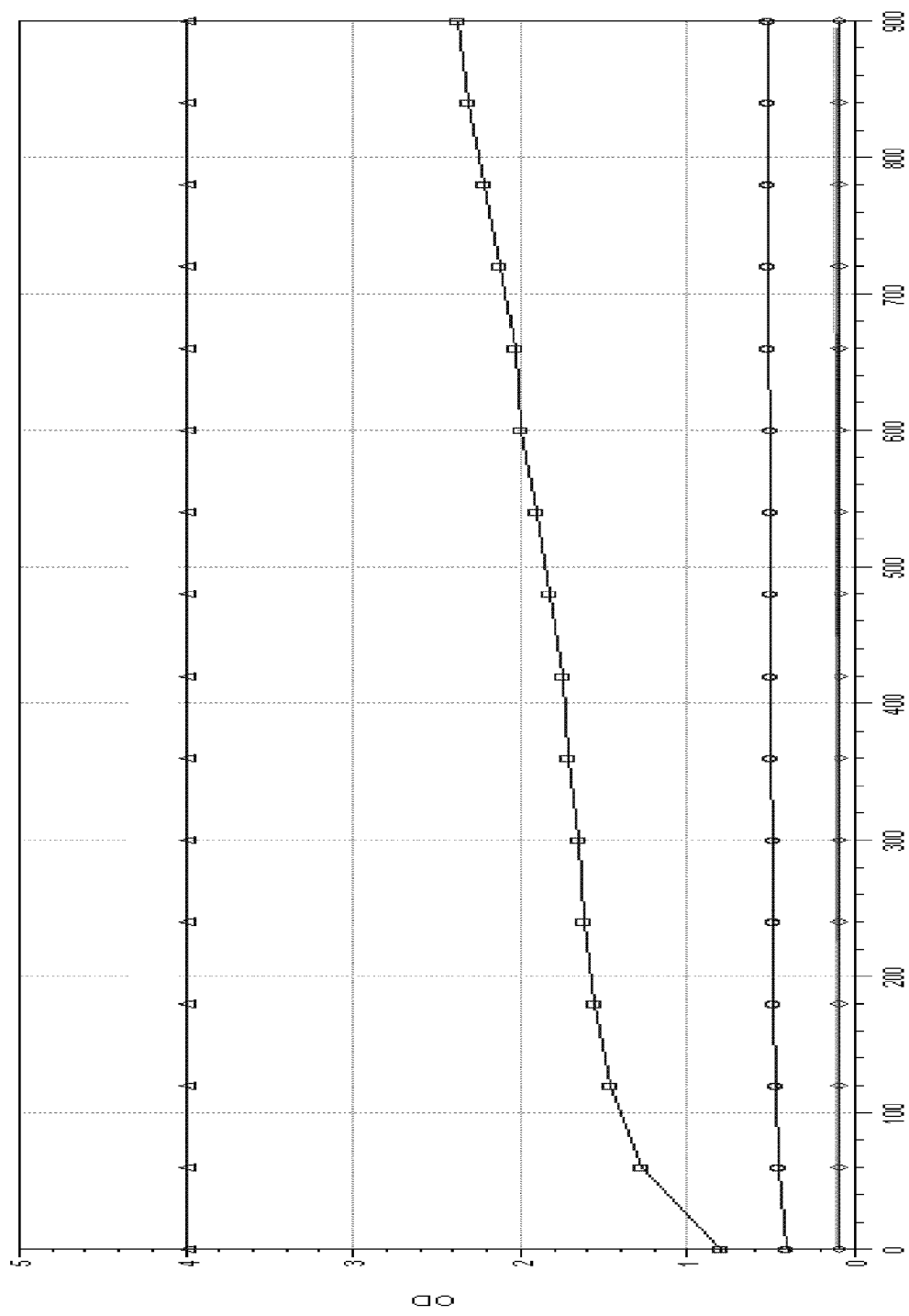
FIG. 15 shows a graphical depiction of α-amylase inhibition according to at least one embodiment of the present disclosure.

Among these five compounds, CDI-034 and CDI-42 were shown to inhibit α-Amylase in 100% saliva samples (See FIG. 15).

3. Lysozyme Inhibition Saliva Screening Method

At least one assay used for the detection of α-amylases activity, as used herein includes the use of a *Micrococcus lysodeikticus* labeled with fluorescein. The assay measures lysozyme activity on *Micrococcus lysodeikticus* cell walls, which are labeled to such a degree that the fluorescence is quenched. Lysozyme activity can relieve this quenching; yielding increased fluorescence that is proportional to lysozyme activity.

For the assay, test compounds are mixed with saliva, prior to the addition of lysozyme substrate. The test compounds, such as GRAS materials, are prepared at a concentration of 5,000 ppm in distilled water. Following this preparation, 50 μl of lysozyme substrate at 1 mg/ml (Molecular Probes EnzChek Lysozyme Assay Kit) that has been pre-heated to 37° C. is added to 50 μl of the test compound. To initiate the assay, 50 μl of a dilute (3.5%) or full strength (100%) saliva solution is added to the mixture. Following the initiation, each mixture is measured at 1 minute intervals using a spectrophotometer (such as Molecular Devices M5 reader) for absorption at 494 nm and fluorescence emission at 518 nm. Temperatures of the mixtures are kept constant at 37° C. during the assay.

4. Lysozyme Inhibitor Assays.

Figure 16:
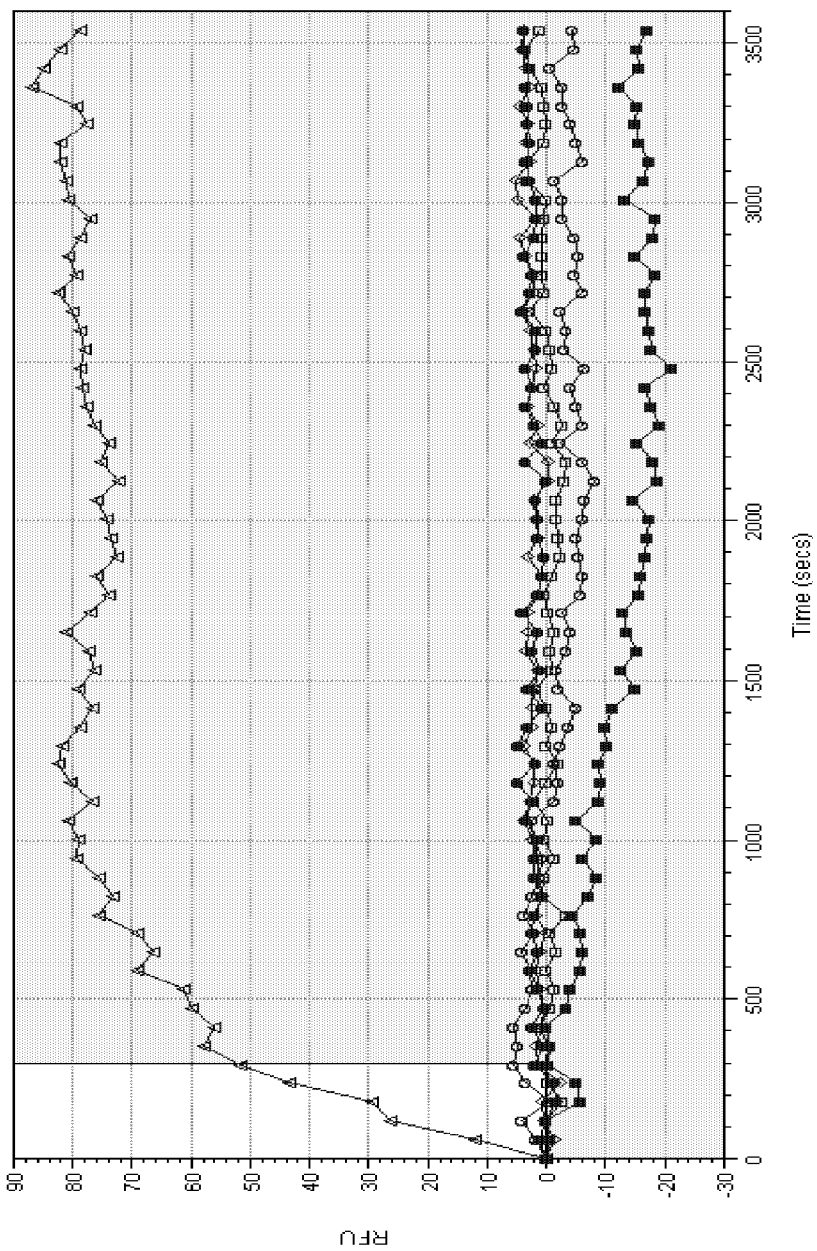
FIG. 16 shows a graphical depiction of lysozyme inhibition according to at least one embodiment of the present disclosure.

A series of GRAS compounds were tested using the Lysozyme assay protocol described above. The tested compounds are included in Table I. From the screen of GRAS compounds, four compounds including Fixanal® Buffer 6.0 (Sigma-Aldrich Co., CDI-030), bentonite (CDI-37), benzoic acid (CDI-40), and acetic acid (CDI-047) were shown to have Lysozyme Inhibitor Activity in dilute (3.5%) saliva (See FIG. 16). Further details of these five compounds may also be seen in Table 5.

TABLE 5

| | Cell Location | RFU Reading (60 mins) |
|---|---|---|
| CDI Candidate # | | |
| 30 | F | 4 | 51.13 |
| 37 | E | 5 | 92.06 |
| 40 | H | 5 | 35.82 |
| 47 | G | 6 | 33.53 |

TABLE 5-continued

| | Cell Location | RFU Reading (60 mins) |
|---|---|---|
| CONTROLS | | |
| Pooled Saliva | E | 12 | 127.33 |
| Fresh Saliva | F | 12 | 182.02 |
| Lysozyme | G | 12 | 233.43 |

Among these four compounds, benzoic acid (CDI-40), and acetic acid (CDI-047) were shown to inhibit Lysozyme in 100% saliva samples (data not shown).

5. Galactose Oxidase Inhibition Saliva Screening Method

At least one assay used for the detection of galactose oxidase activity, as used herein, includes the use of a chromagenic or fluorogenic substrate, such as with Amplex® Red (Molecular Probes). In an embodiment of the assay used herein, galactose oxidase catalyzes the oxidation of galactose at the C6 position and generates hydrogen peroxide (H2O2). The H2O2 then, in the presence of horseradish peroxidase (HRP), reacts with 1:1 stoichiometry with Amplex® Red reagent to generate the red-fluorescent oxidation product, resorufin. Resorufin has absorption and fluorescence emission maxima of approximately 571 nm and 585 nm, respectively, and because the extinction coefficient is high (54,000 cm-1M-1), the assay can be performed either fluorometrically or spectrophotometrically.

For the assay, test compounds are mixed with Amplex Red, reaction buffer, horseradish peroxidase (HRP) at 100 U/ml, and galactose stock solution (according to manufacturers recommended protocol, Molecular Probes A22179), prior to the addition of saliva. The test compounds, such as GRAS materials, are prepared under various concentration for testing. Following this preparation, 50 μl of the test compound solution (with Amplex Red, reaction buffer, and HRP) is added to 50 μl of saliva. Following the initiation, each mixture is measured at 1 minute intervals using a spectrophotometer (such as Molecular Devices M5 reader) using excitation in the range of 530-560 nm and emission detection at about 590 nm or absorbance at 560 nm. Temperatures of the mixtures are kept constant at 37° C. during the assay.

6. Galactose Oxidase Inhibitor Assays.

Figure 17:
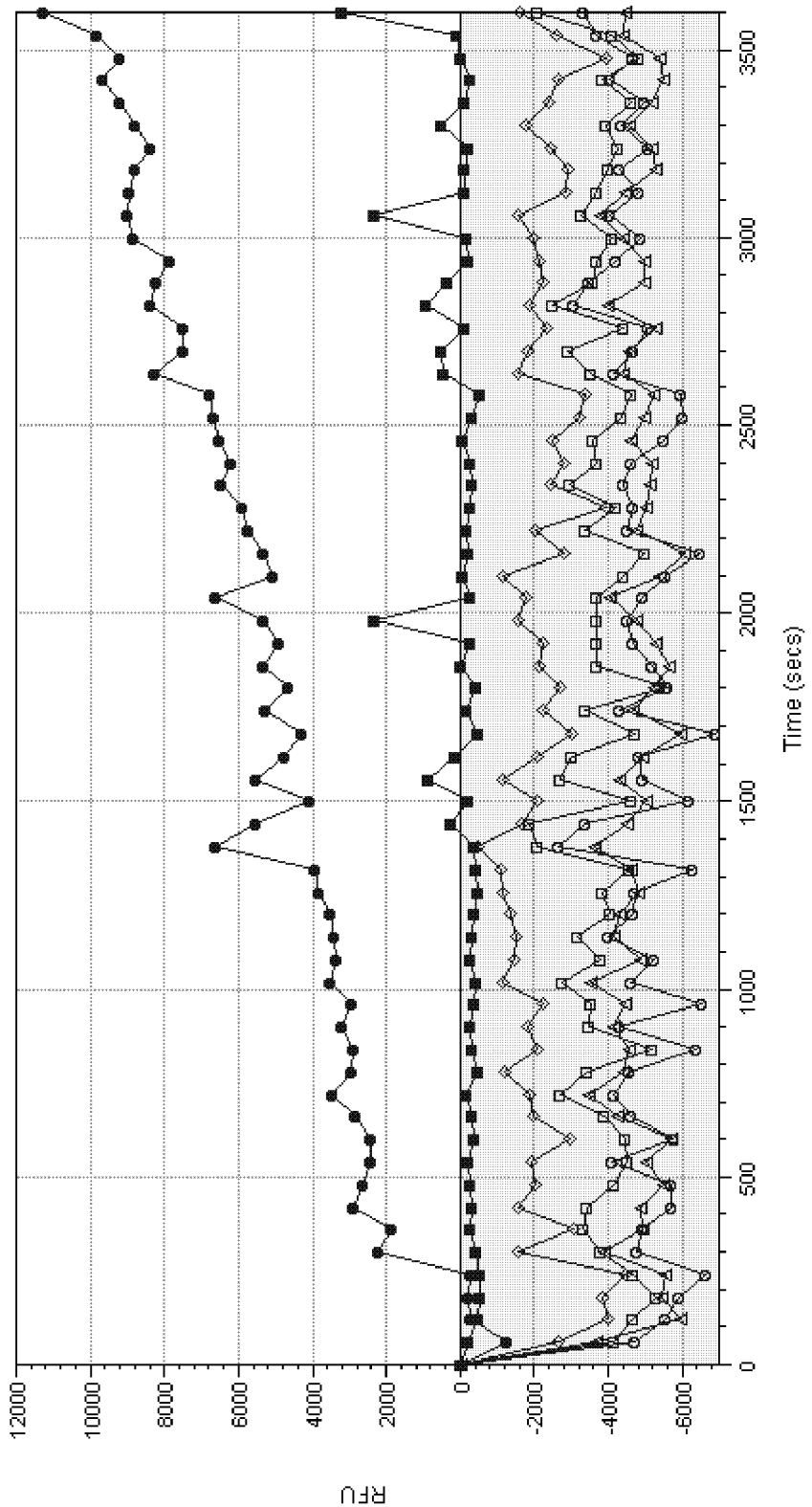
FIG. 17 shows a graphical depiction of a galactose oxidase screen according to at least one embodiment of the present disclosure.

A series of GRAS compounds were tested using the Galactose Oxidase assay protocol described herein. The tested compounds are included in Table I. From the screen of GRAS compounds, four compounds (CDI-039, 040, 042, and 047) were shown to have Galactose Oxidase Inhibitor Activity in dilute (3.5%) saliva (See FIG. 17). FIG. 17 includes the following symbols which are: open circle=Aluminum potassium sulfate dodecahydrate, open square=3-tert-butyl-hydroxyanisole, open triangle=benzoic acid, open diamond=acetic acid, filled circle=fresh saliva, and filled square=water (control blank).

7. Stabilization of Glycosylated Hemoglobin

Figure 18A:
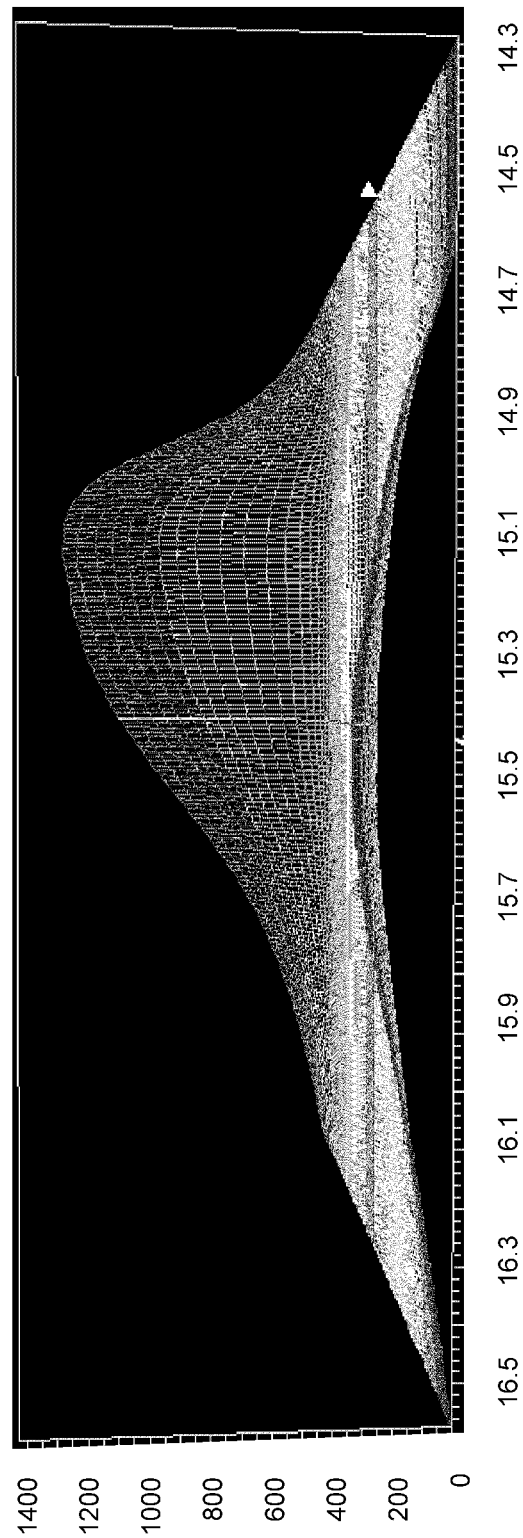
FIG. 18A shows a three dimensional plot of glycated Hemoglobin A1c (HbA1c) analyzed by high pressure liquid chromatography (HPLC) according to at least one embodiment of the present disclosure.
Figure 18B:
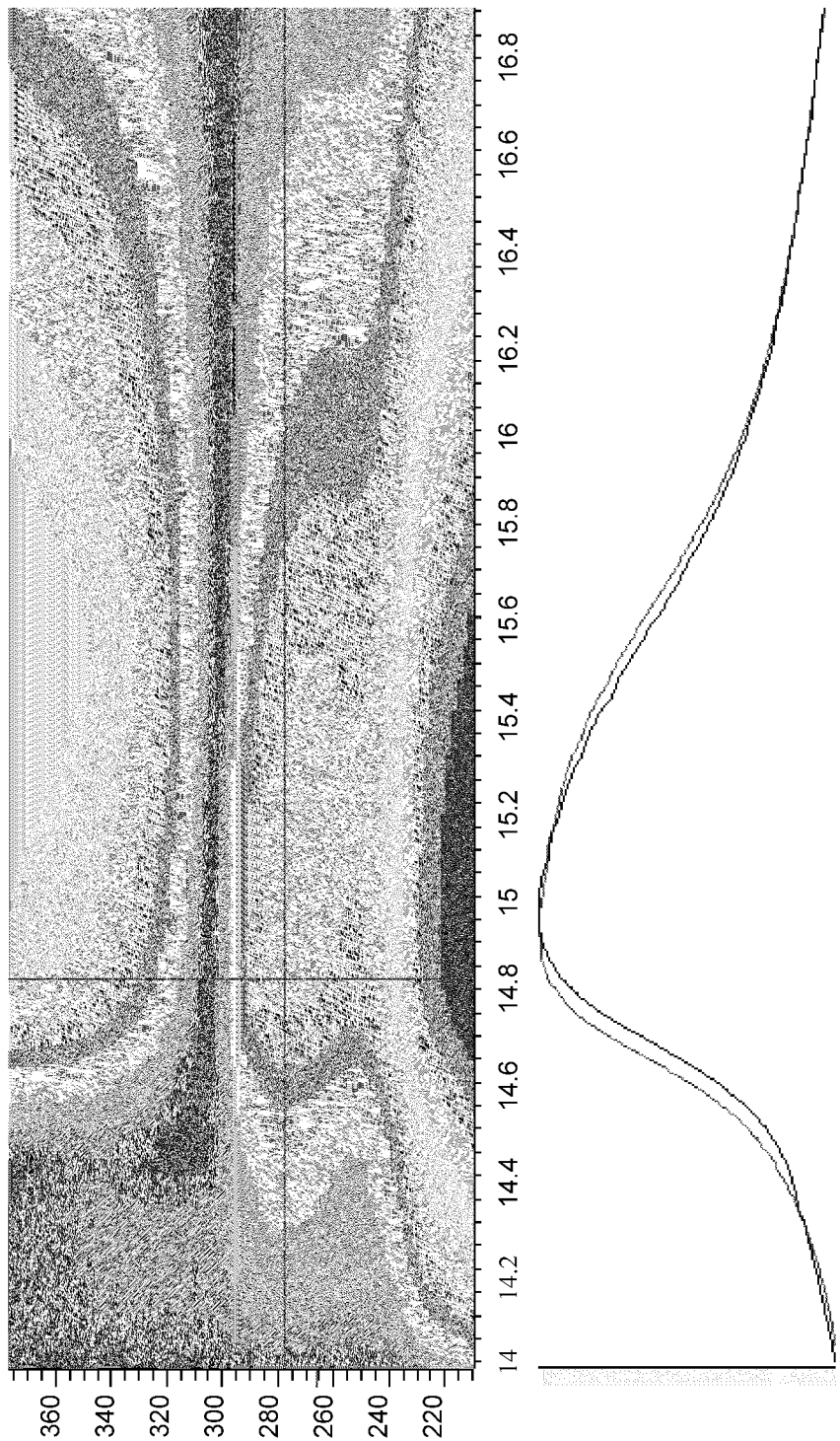
FIG. 18B shows a ultraviolet (UV) image of HbA1c analyzed by HPLC according to at least one embodiment of the present disclosure.
Figure 18C:
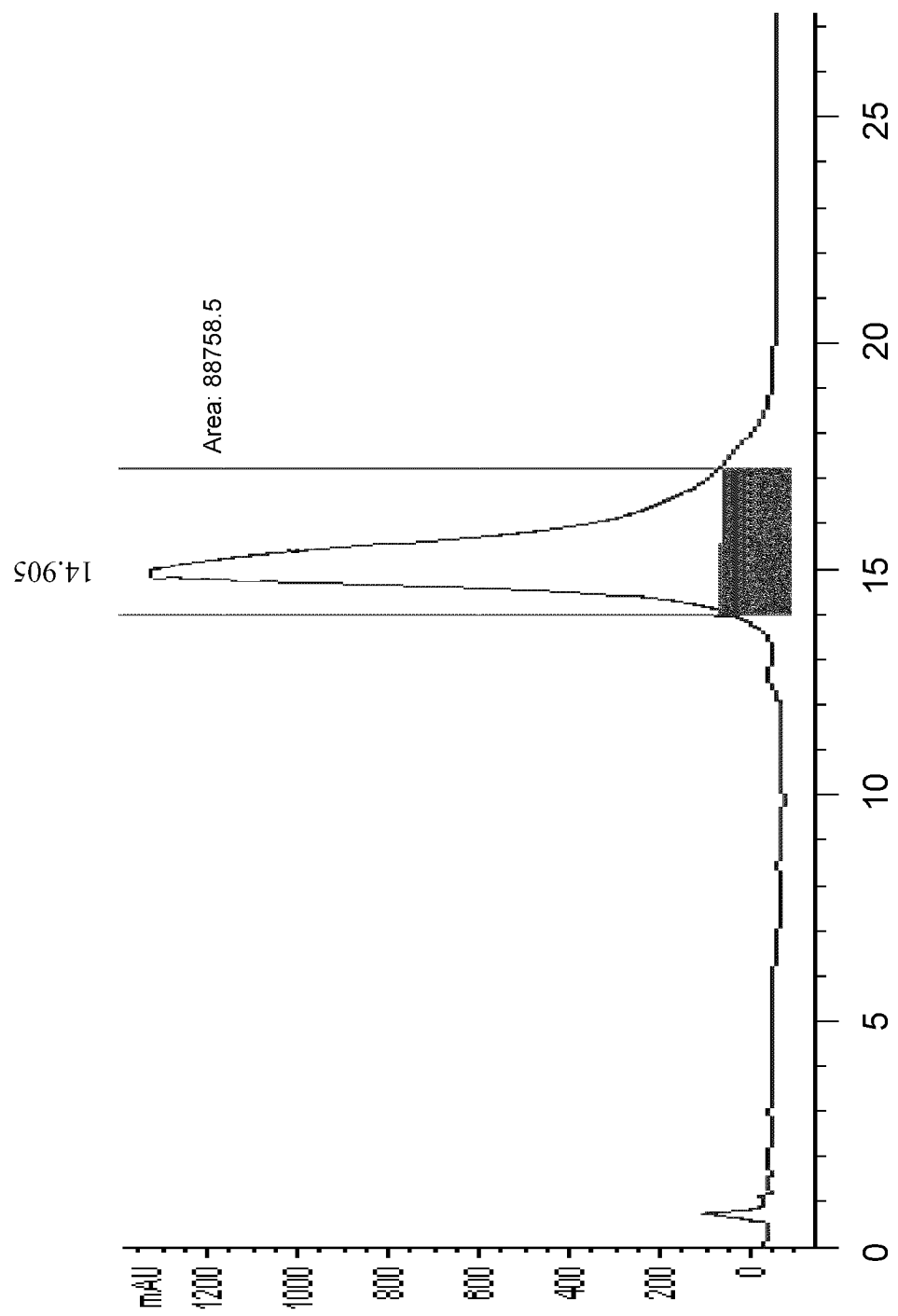
FIG. 18C shows a chromatogram of HbA1c analyzed by HPLC according to at least one embodiment of the present disclosure.
Figure 19A:
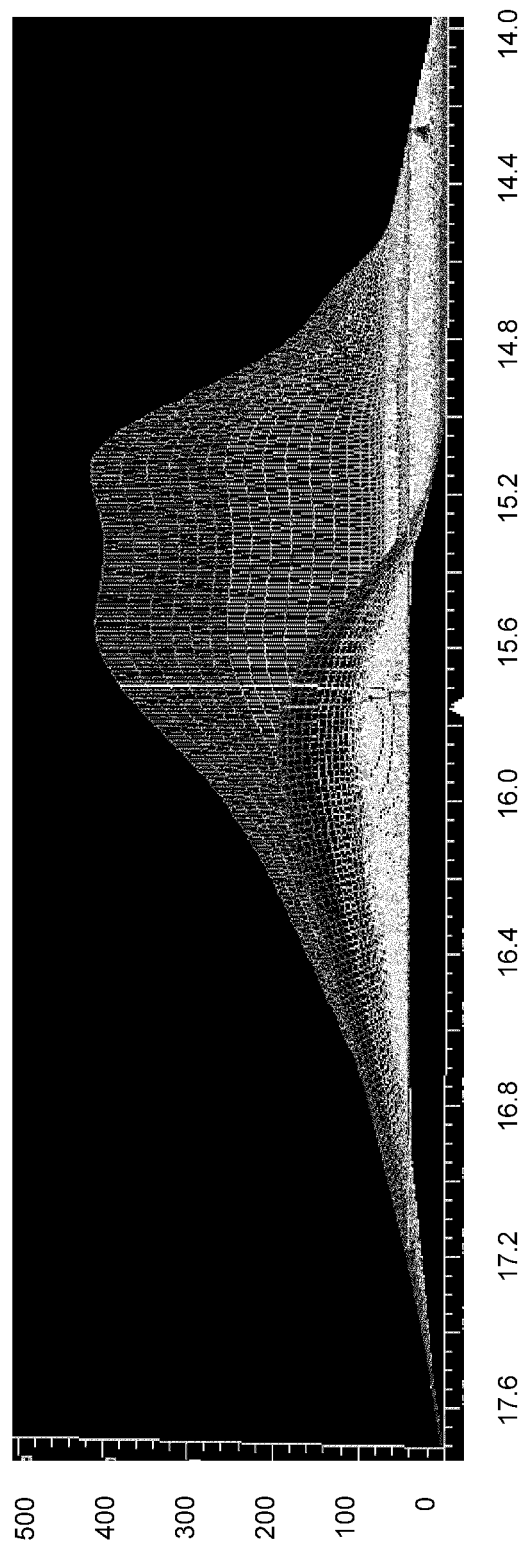
FIG. 19A shows a three dimensional plot of HbA1c analyzed by HPLC following exposure to saliva according to at least one embodiment of the present disclosure.
Figure 19B:
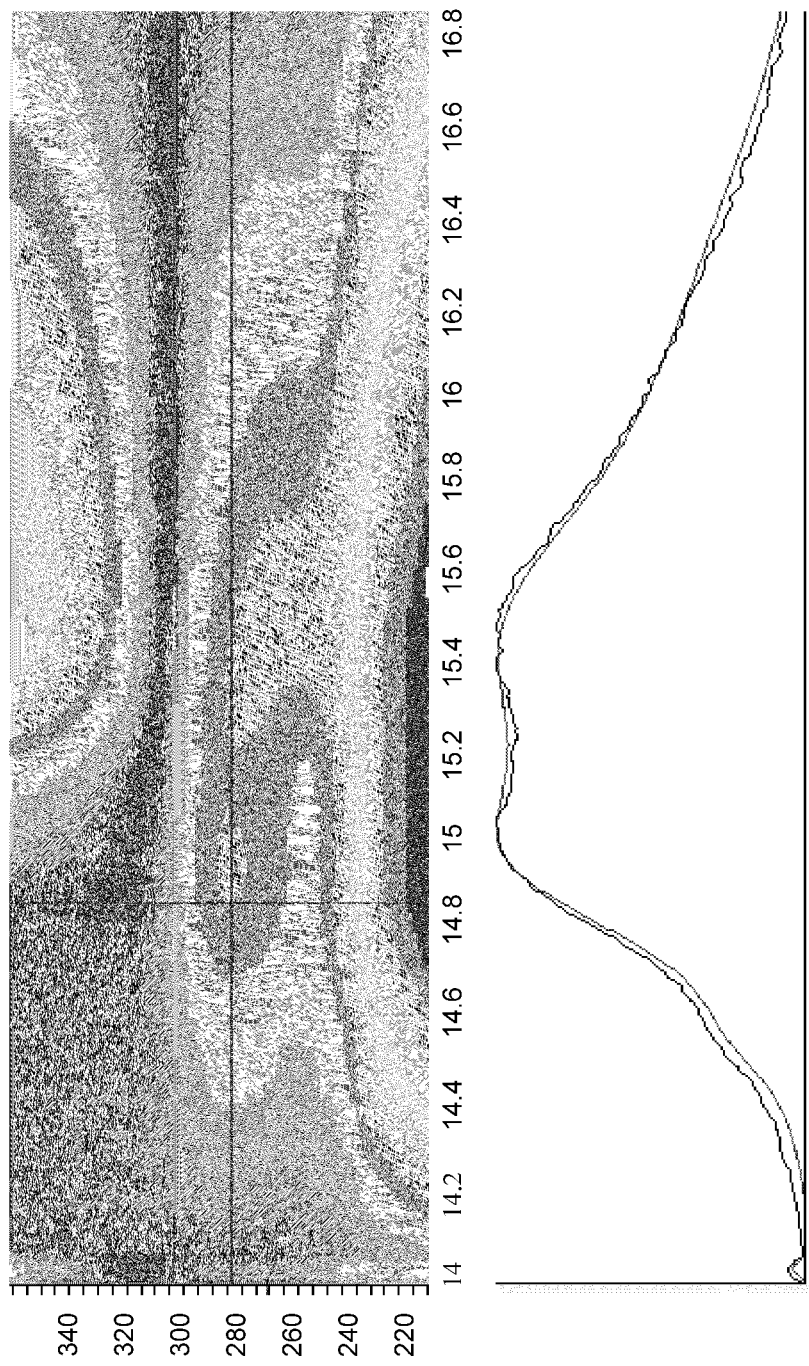
FIG. 19B shows a UV image of HbA1c analyzed by HPLC following exposure to saliva according to at least one embodiment of the present disclosure.
Figure 19C:
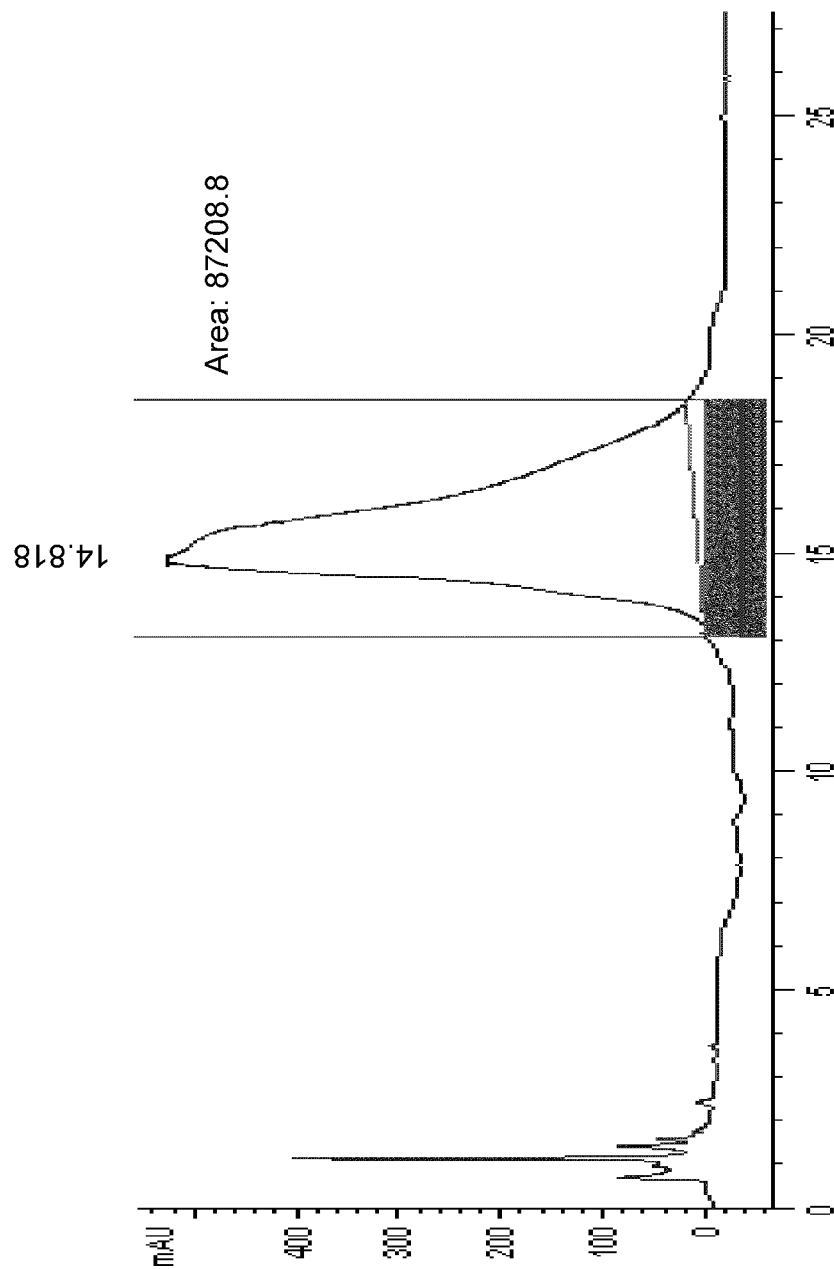
FIG. 19C shows a chromatogram of HbA1c analyzed by HPLC following exposure to saliva according to at least one embodiment of the present disclosure.
Figure 20A:
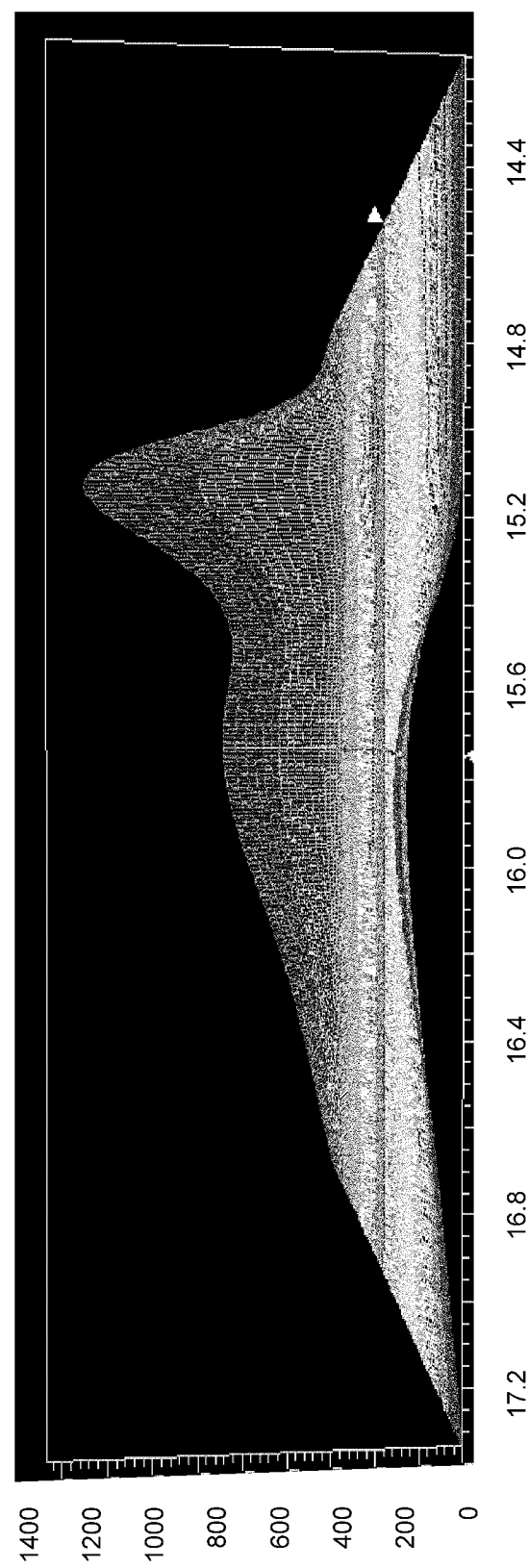
FIG. 20A shows a three dimensional plot of HbA1c analyzed by HPLC following exposure to saliva and a stabilizing mixture according to at least one embodiment of the present disclosure.
Figure 20B:
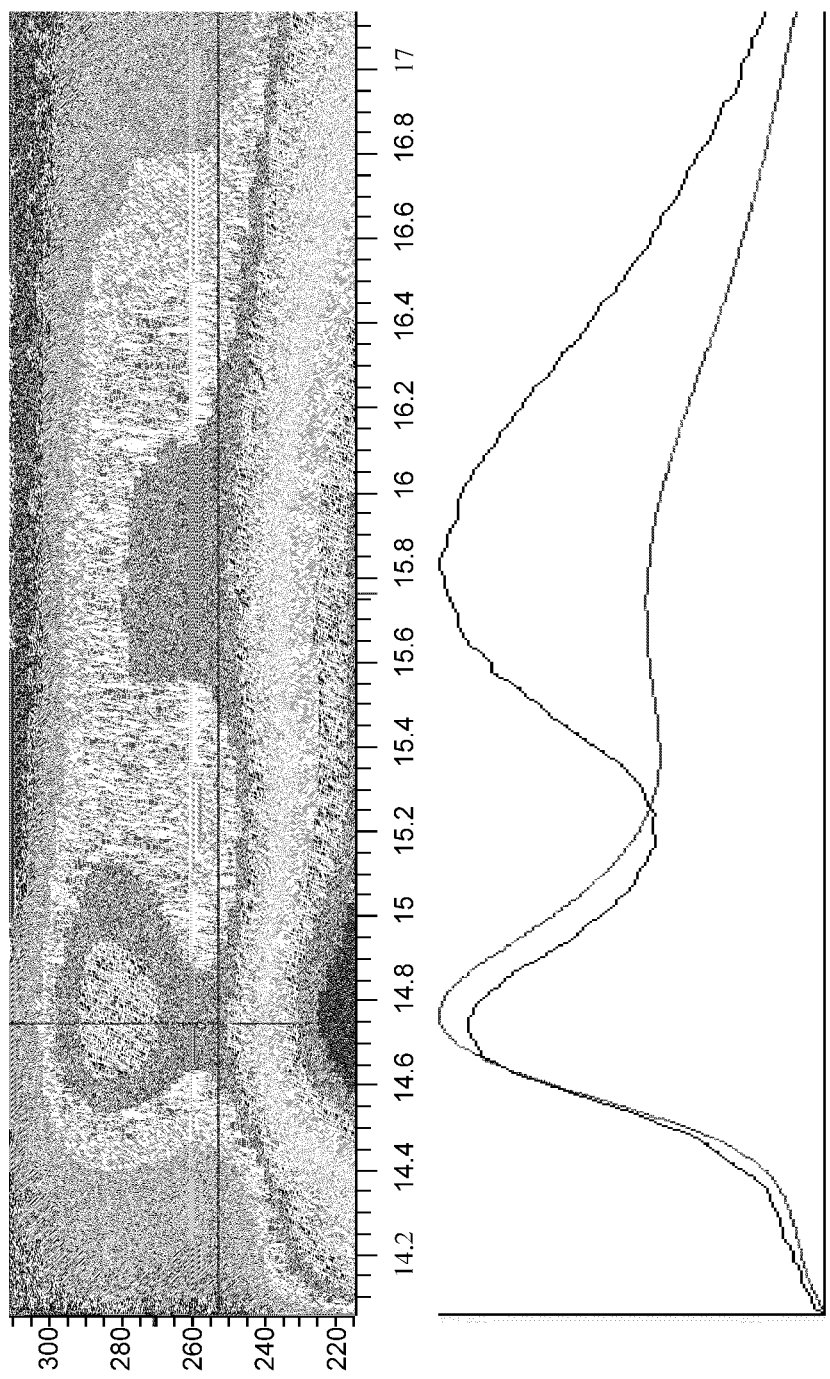
FIG. 20B shows a UV image of HbA1c analyzed by HPLC following exposure to saliva and a stabilizing mixture according to at least one embodiment of the present disclosure.
Figure 20C:
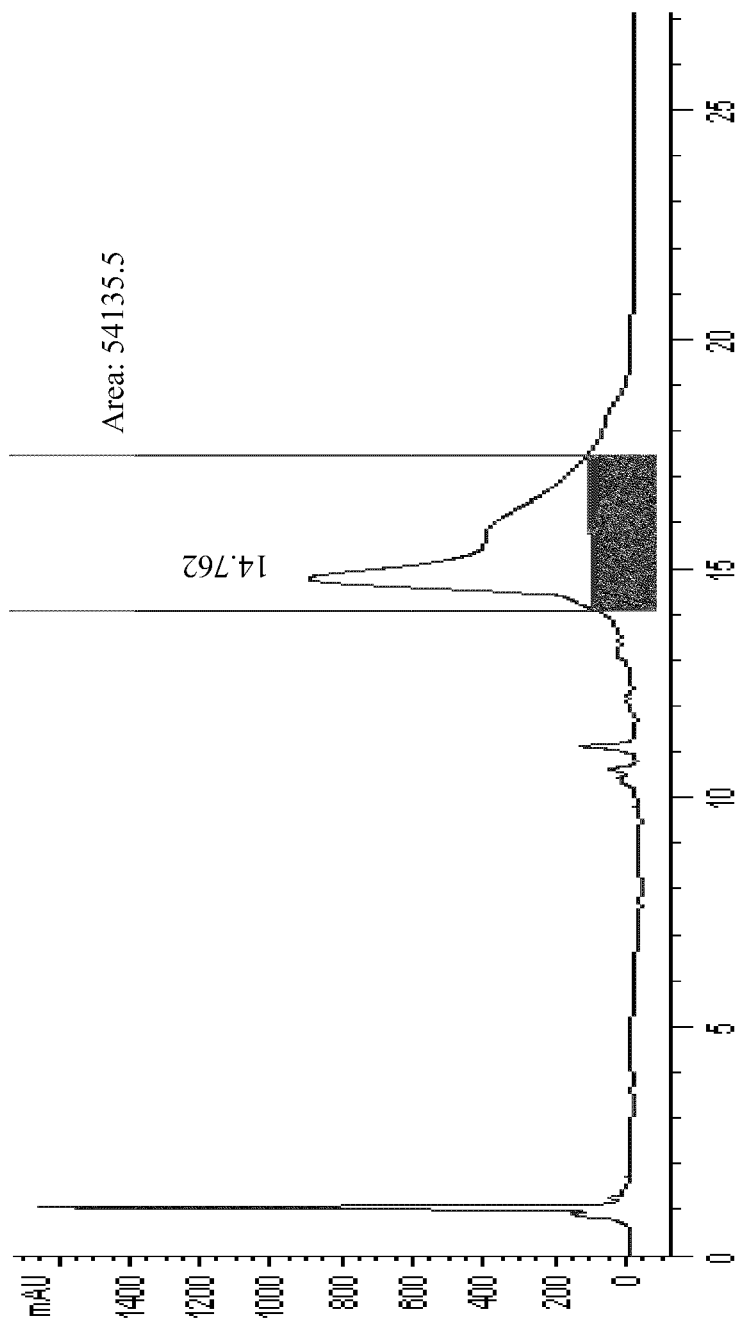
FIG. 20C shows a chromatogram of HbA1c analyzed by HPLC following exposure to saliva and a stabilizing mixture according to at least one embodiment of the present disclosure.
Figure 21A:
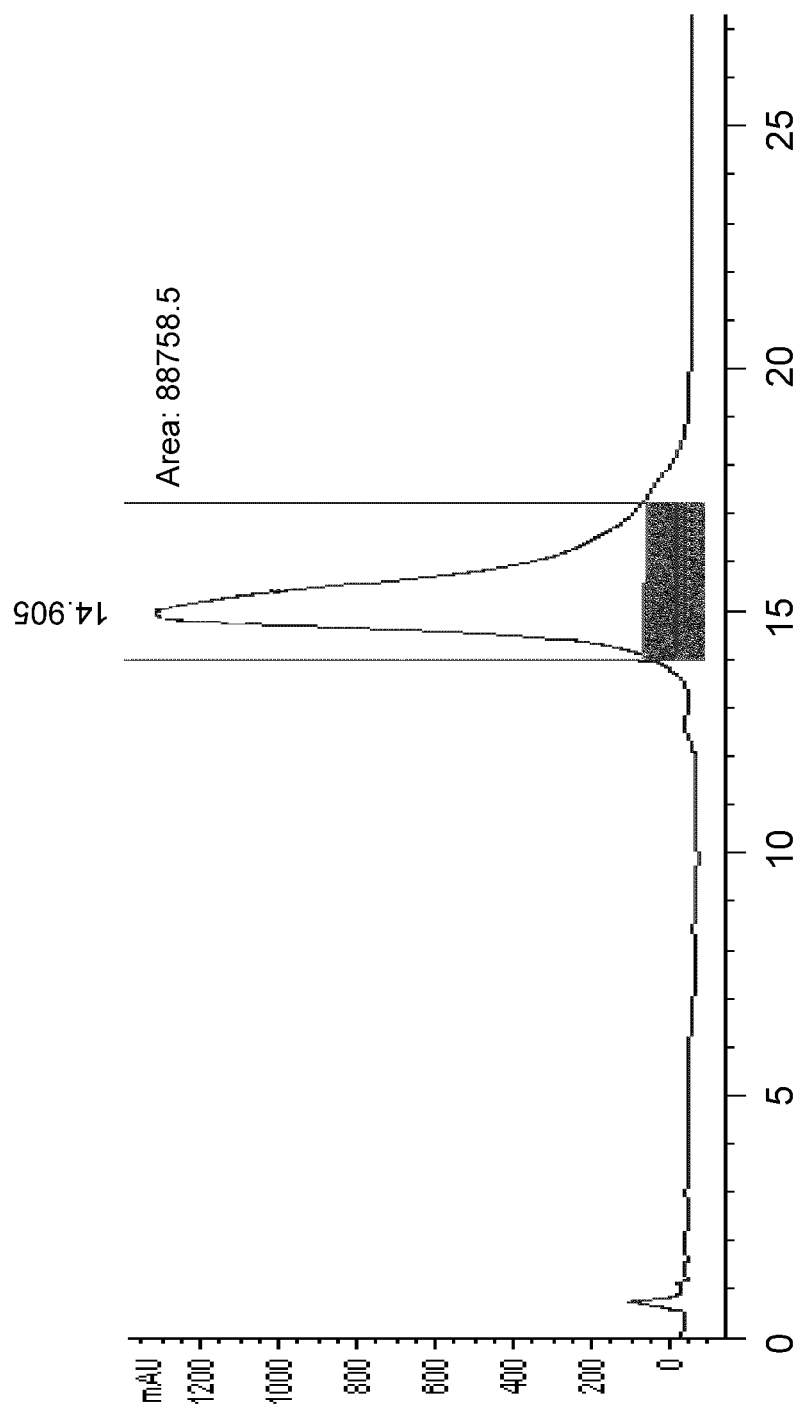
FIG. 21 shows a comparison of chromatograms from HPLC analyzed HbA1c (FIG. 21A), HbA1c+Saliva (FIG. 21B), and HbA1c+Saliva+Stabilizing mixture (FIG. 21C) according to at least one embodiment of the present disclosure.
Figure 21B:
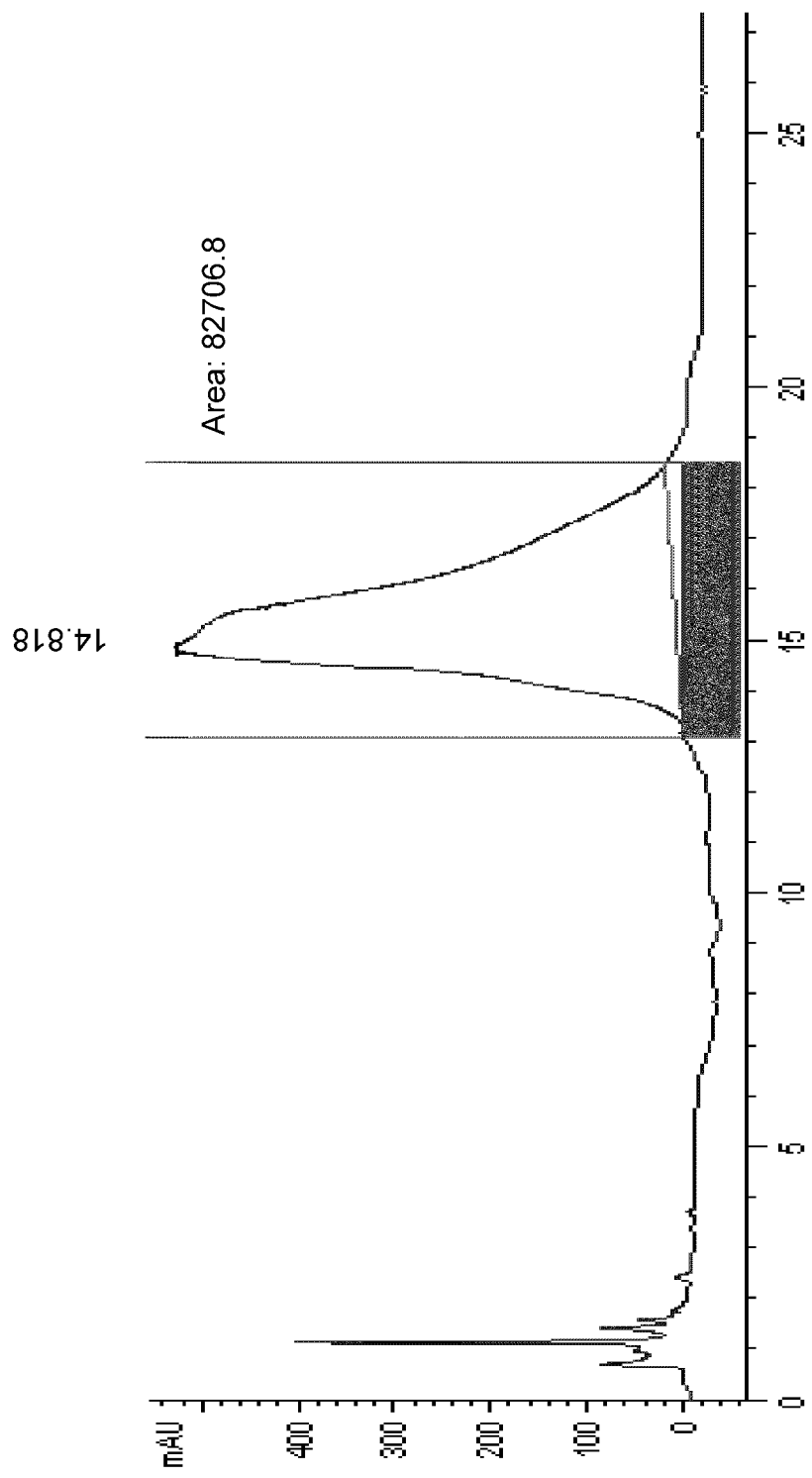
Figure 21C:
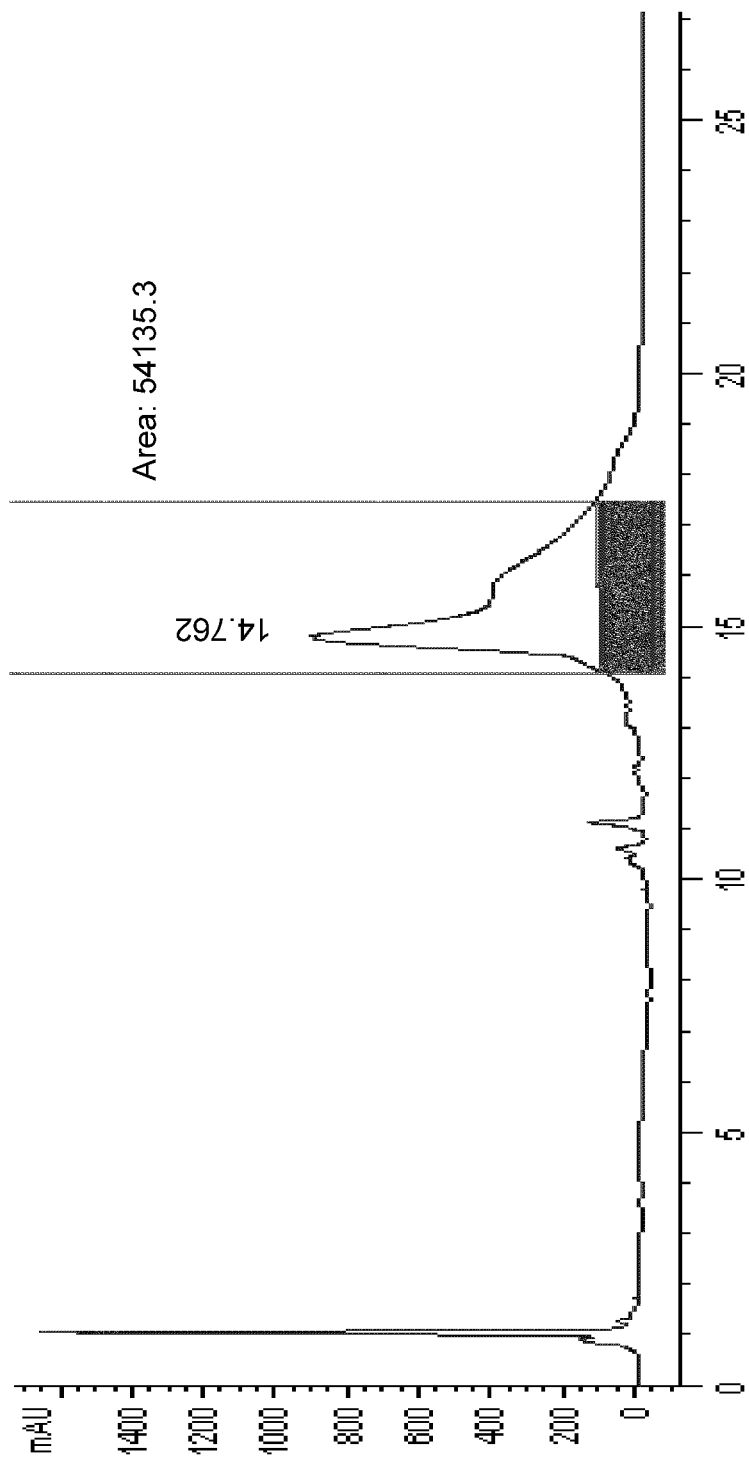
Figure 22A:
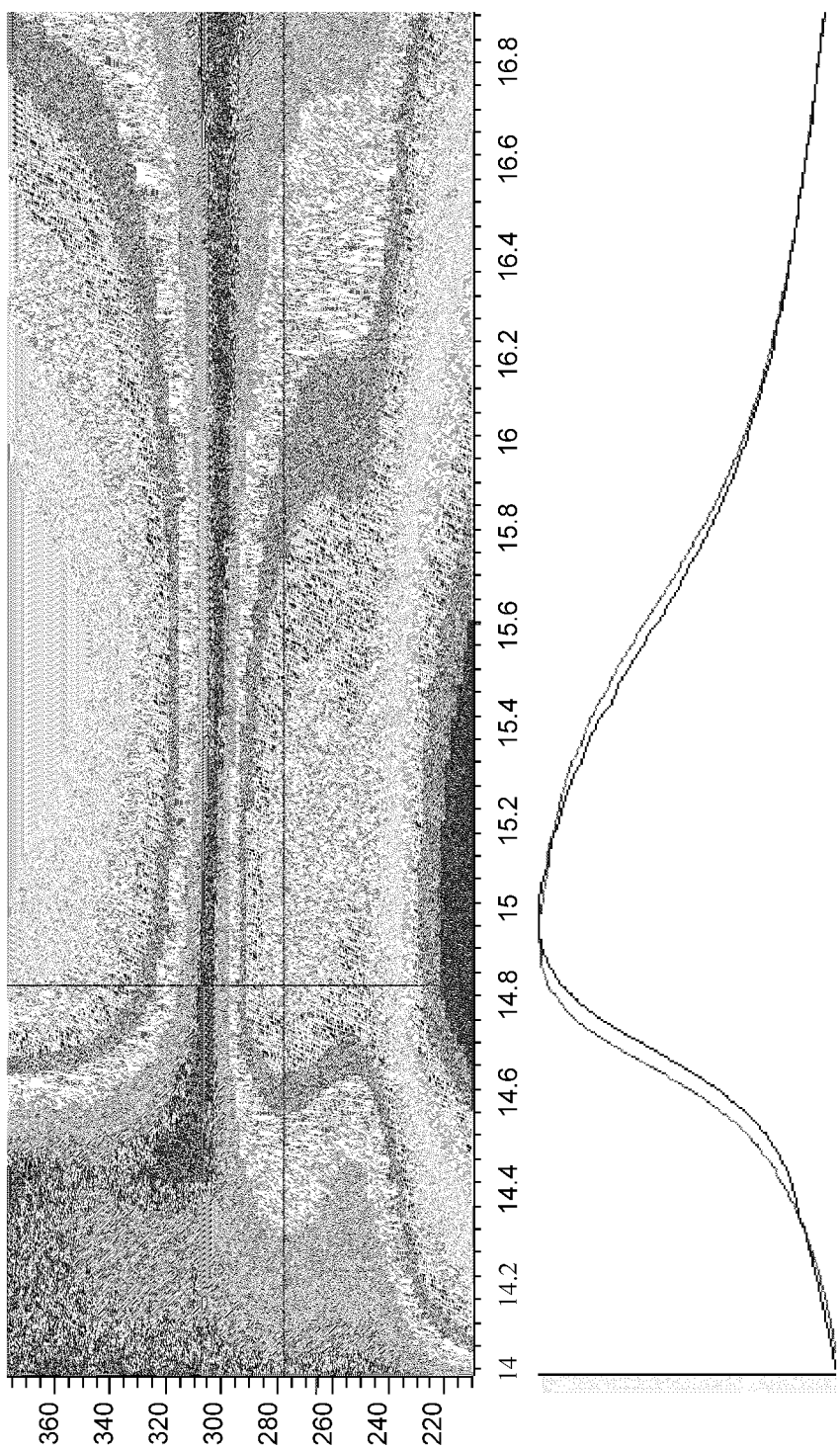
FIG. 22 shows a comparison of UV images from HPLC analyzed HbA1c (FIG. 22A), HbA1c+Saliva (FIG. 22B), and HbA1c+Saliva+Stabilizing mixture (FIG. 22C) according to at least one embodiment of the present disclosure.
Figure 22B:
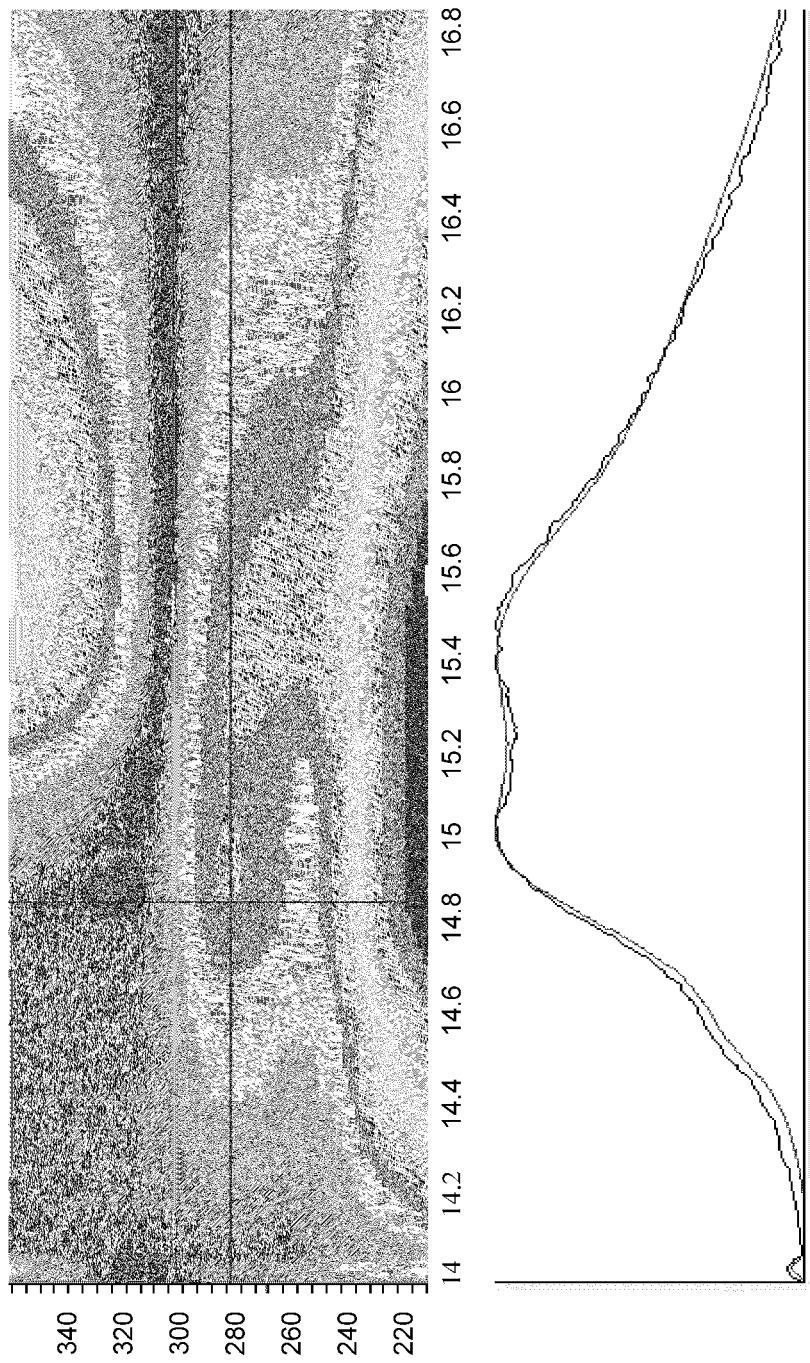
Figure 22C:
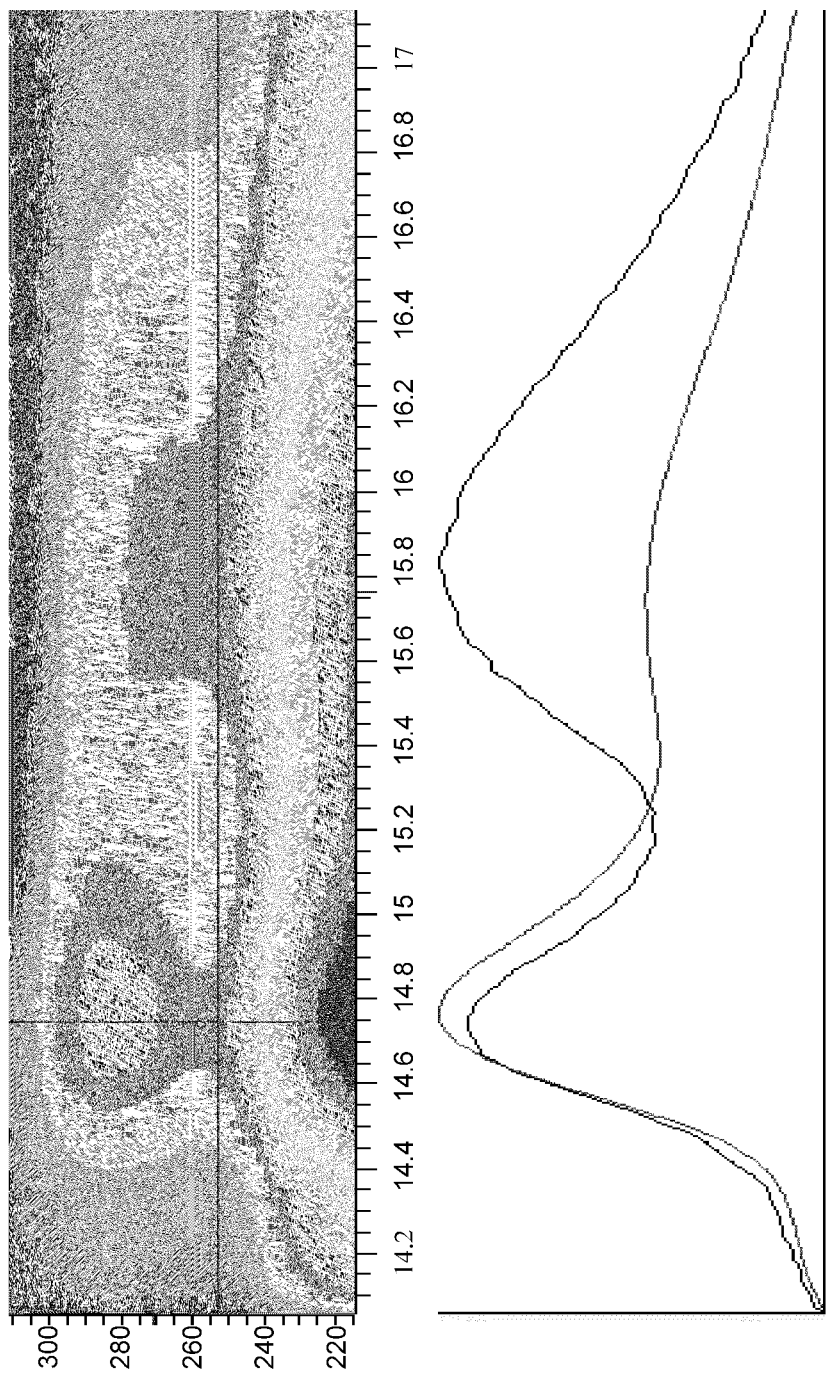
Figure 23A:
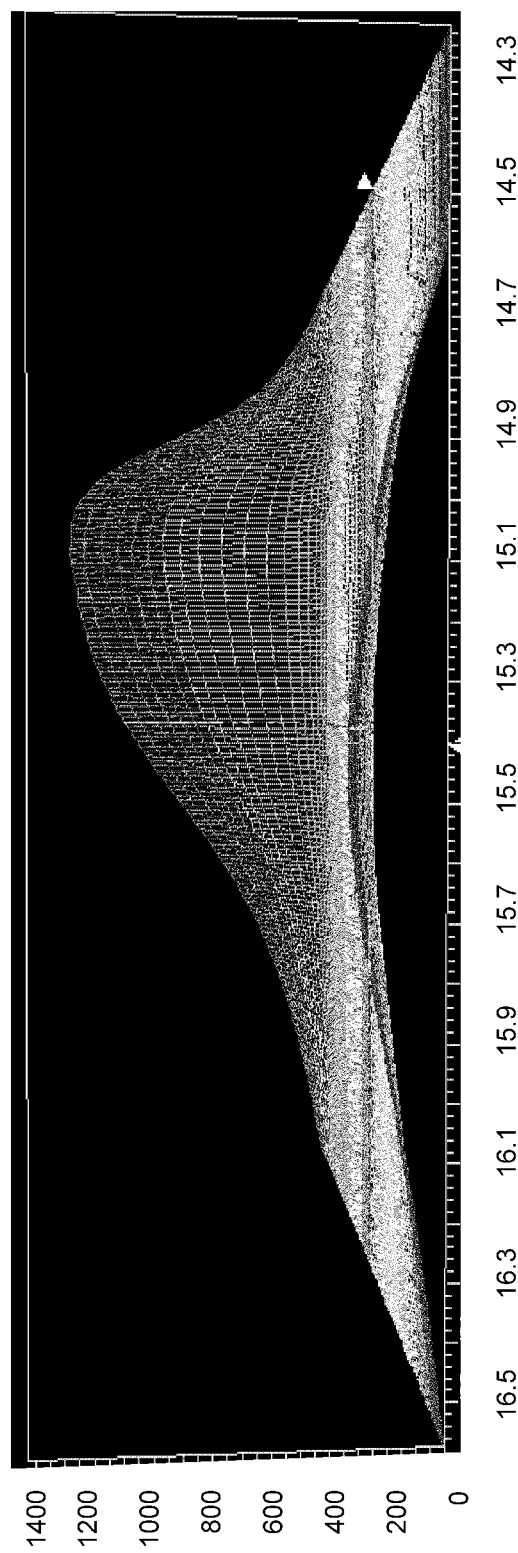
FIG. 23 shows a comparison of three dimensional plots from HPLC analyzed HbA1c (FIG. 23A), HbA1c+Saliva (FIG. 23B), and HbA1c+Saliva+Stabilizing mixture (FIG. 23C) according to at least one embodiment of the present disclosure.
Figure 23B:
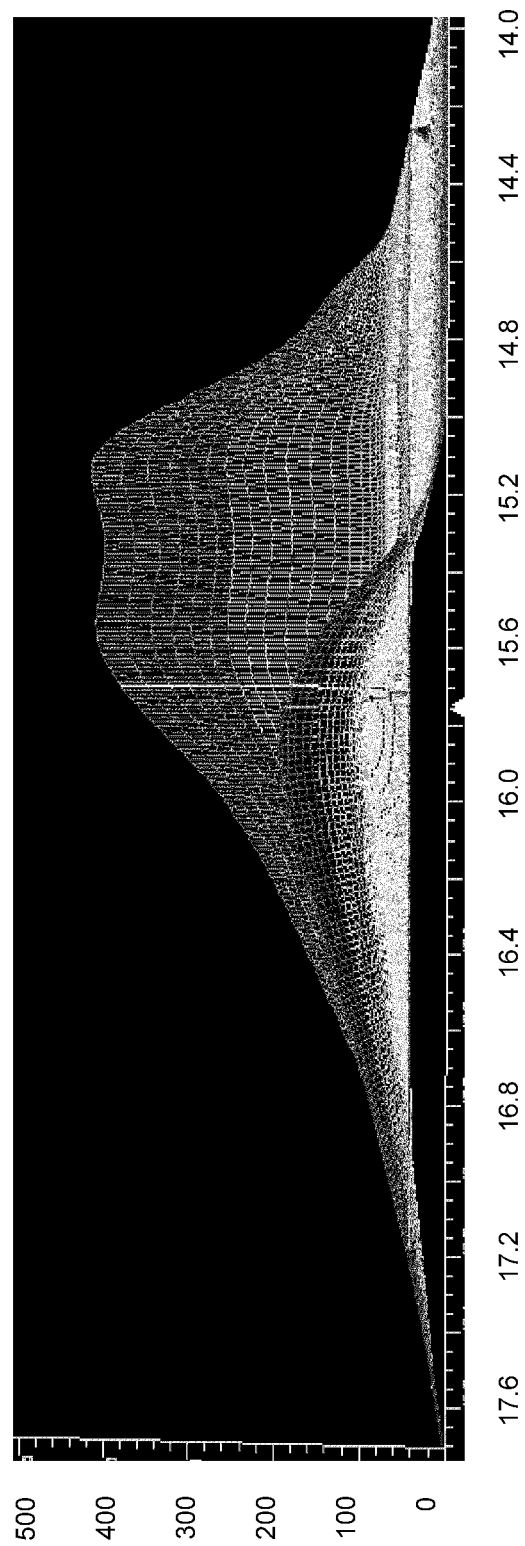
Figure 23C:
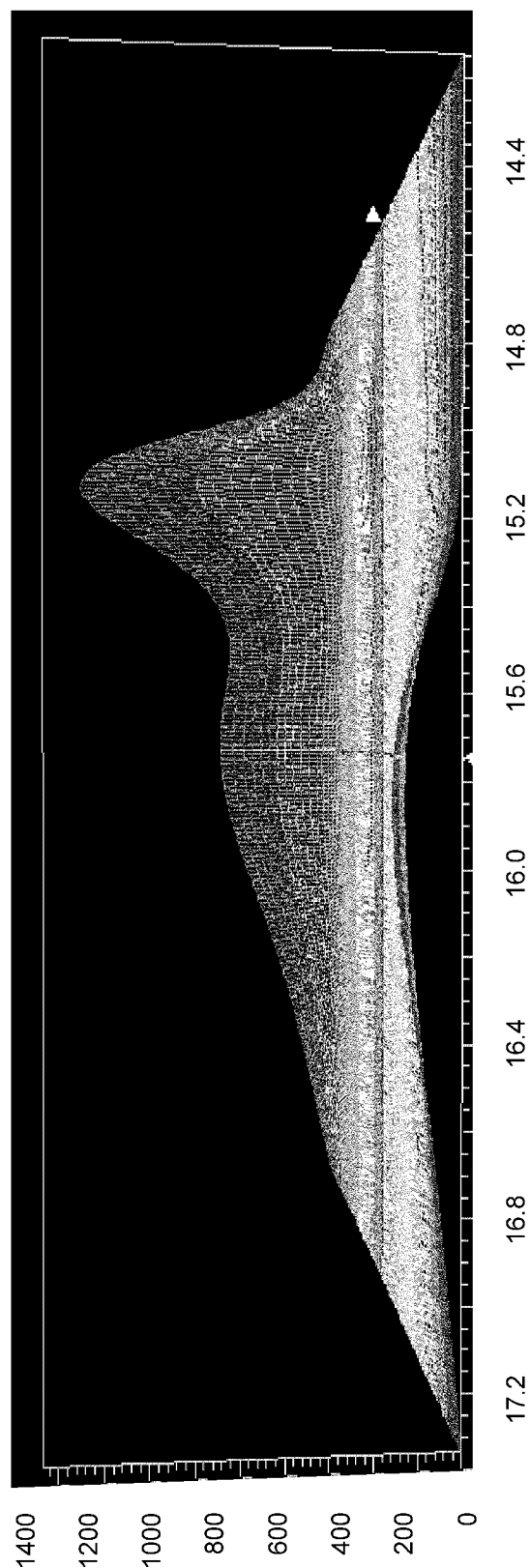

At least one procedure used for the stabilization and detection of glycosylated hemoglobin (HbA1c), as described herein, includes the incubation of HbA1c with a stabilizing agent prior to, or concurrently with, detection. Analysis of samples was conducted on a HPLC 1100 series (Agilent Technologies) with a 2.1×150 (3.5μ) C18 reverse phase column. The mobile phase used was acetonitrile with 6.5 mM Ammonium Carbonate. A HbA1c standard was prepared by dissolving HbA1c (Sigma Aldrich, 405 RM) with 1.0 ml of deionized water. The samples analyzed by HPLC included pure HbA1c (FIG. 18), 100 ml HbA1c mixed with 100 ml of fresh saliva (FIG. 19), and 200 ml HbA1c mixed with 100 ml of fresh saliva and 100 ml of a stabilizing compound comprising aluminum sulfate hydrate, benzoic acid, and aluminum potassium sulfate dodecahydrate (each present in a 1:1:1 ratio) (FIG. 20). While the pure HbA1c sample was analyzed fresh, samples of HbA1c with saliva were incubated overnight at room temperature prior to analysis. For each sample analyzed, the data was displayed through a three dimensional plot (FIGS. 18A, 19A, and 20A), a UV image (FIGS. 18B, 19B, and 20B), and a chromatogram (FIGS. 18C, 19C, and 20C). Additionally, a comparison of the analysis HbA1c in the presence of saliva with and without stabilizing agent is shown in FIGS. 21 (chromatography), 22 (UV image), and 23 (three dimensional plot).

8. HbA1c Protection Assays

A series of GRAS compounds were tested, as shown in FIGS. 18-20, for the ability to protect HbA1c from degradation by components in saliva. The tested compounds are included in Table I. As described above, a stabilizing compound comprising aluminum sulfate hydrate, benzoic acid, and aluminum potassium sulfate dodecahydrate (each present in a 1:1:1 ratio) minimized the degradation of HbA1c, and yielded a defined pattern for HbA1c.

9. Stabilization of Cancer Antigen 19-9

Figure 24A:
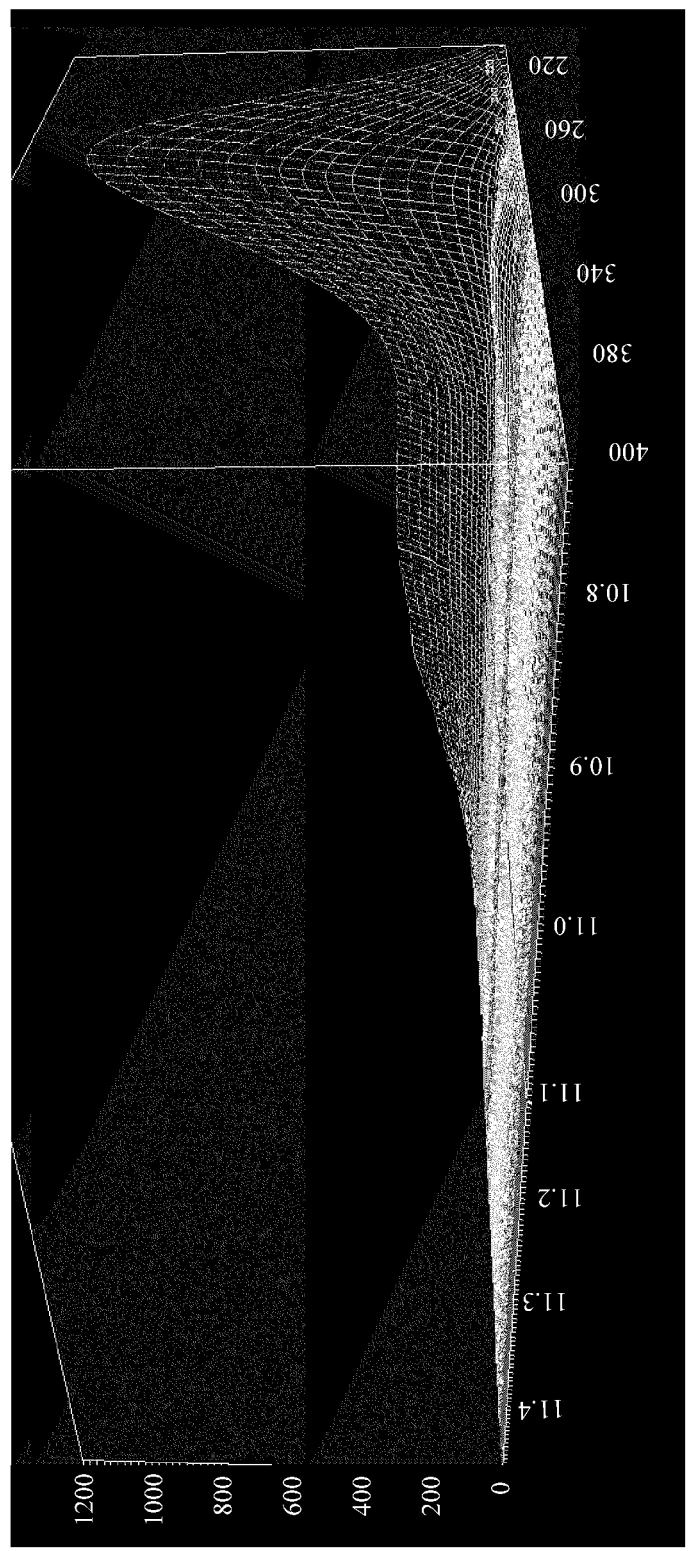
FIG. 24A shows a three dimensional plot of Cancer Antigen 19-9 (CA 19-9) analyzed by high pressure liquid chromatography (HPLC) according to at least one embodiment of the present disclosure.
Figure 24B:
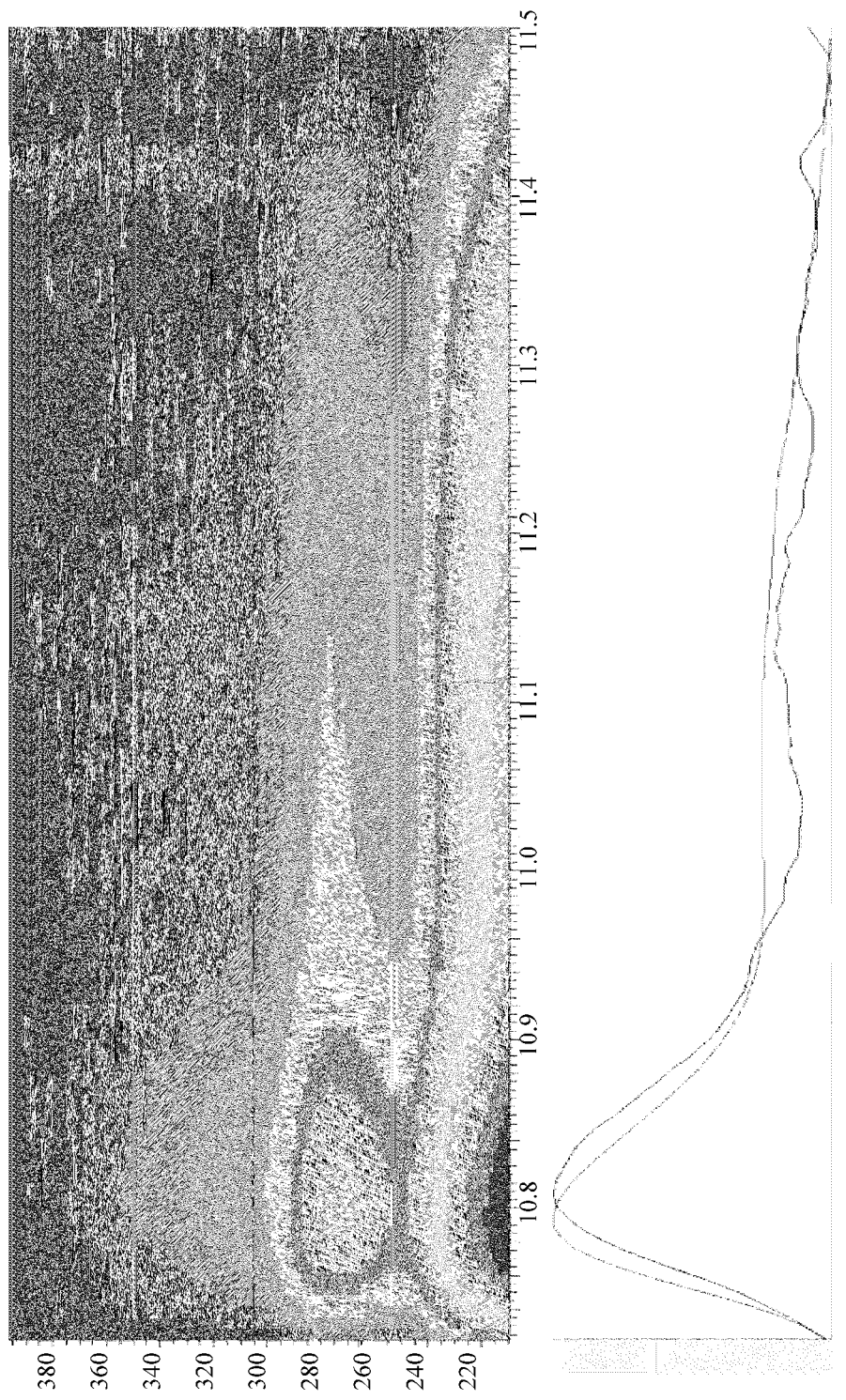
FIG. 24B shows a ultraviolet (UV) image of CA 19-9 analyzed by HPLC according to at least one embodiment of the present disclosure.
Figure 25A:
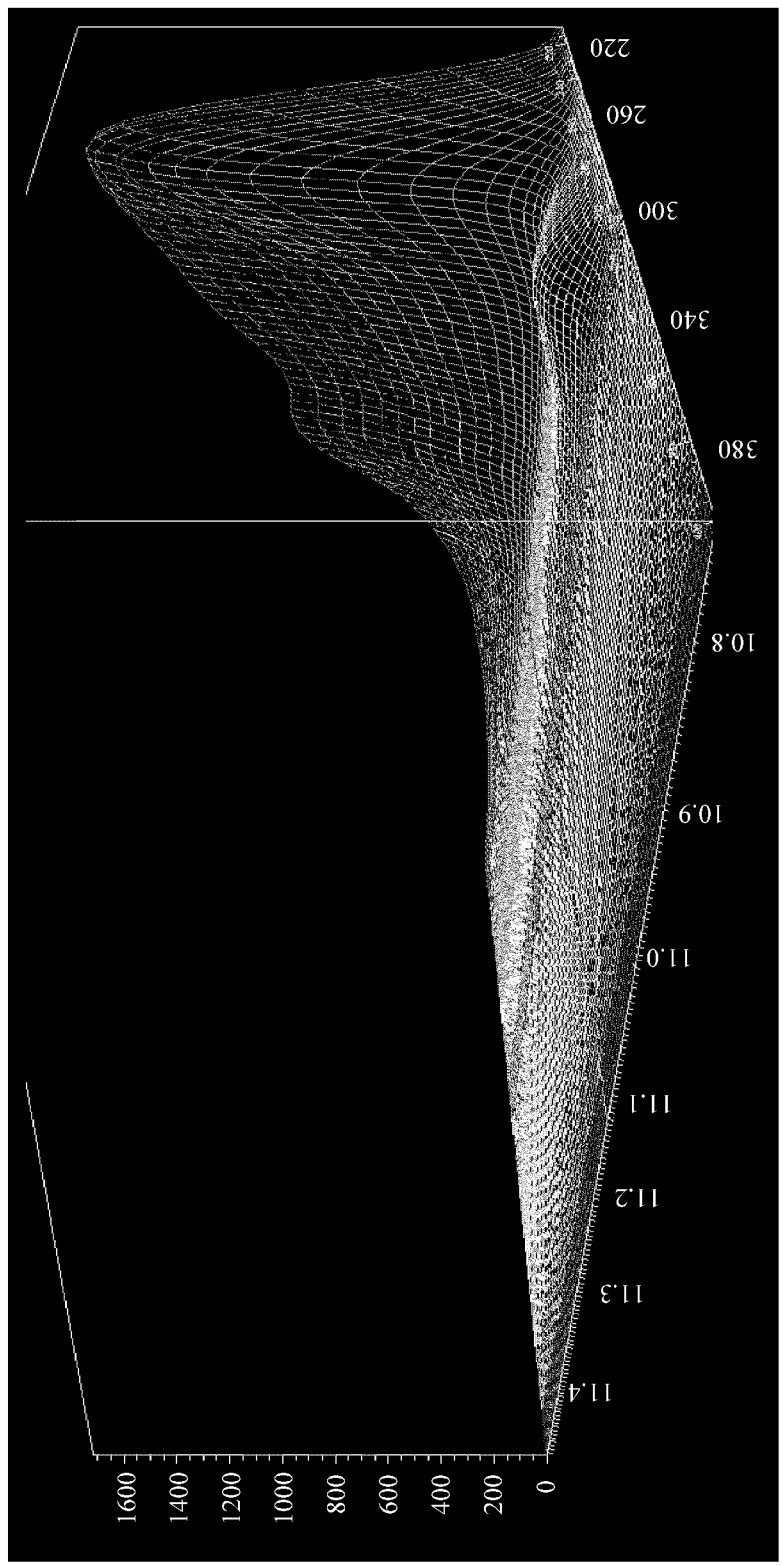
FIG. 25A shows a three dimensional plot of CA 19-9 analyzed by HPLC following exposure to saliva according to at least one embodiment of the present disclosure.
Figure 25B:
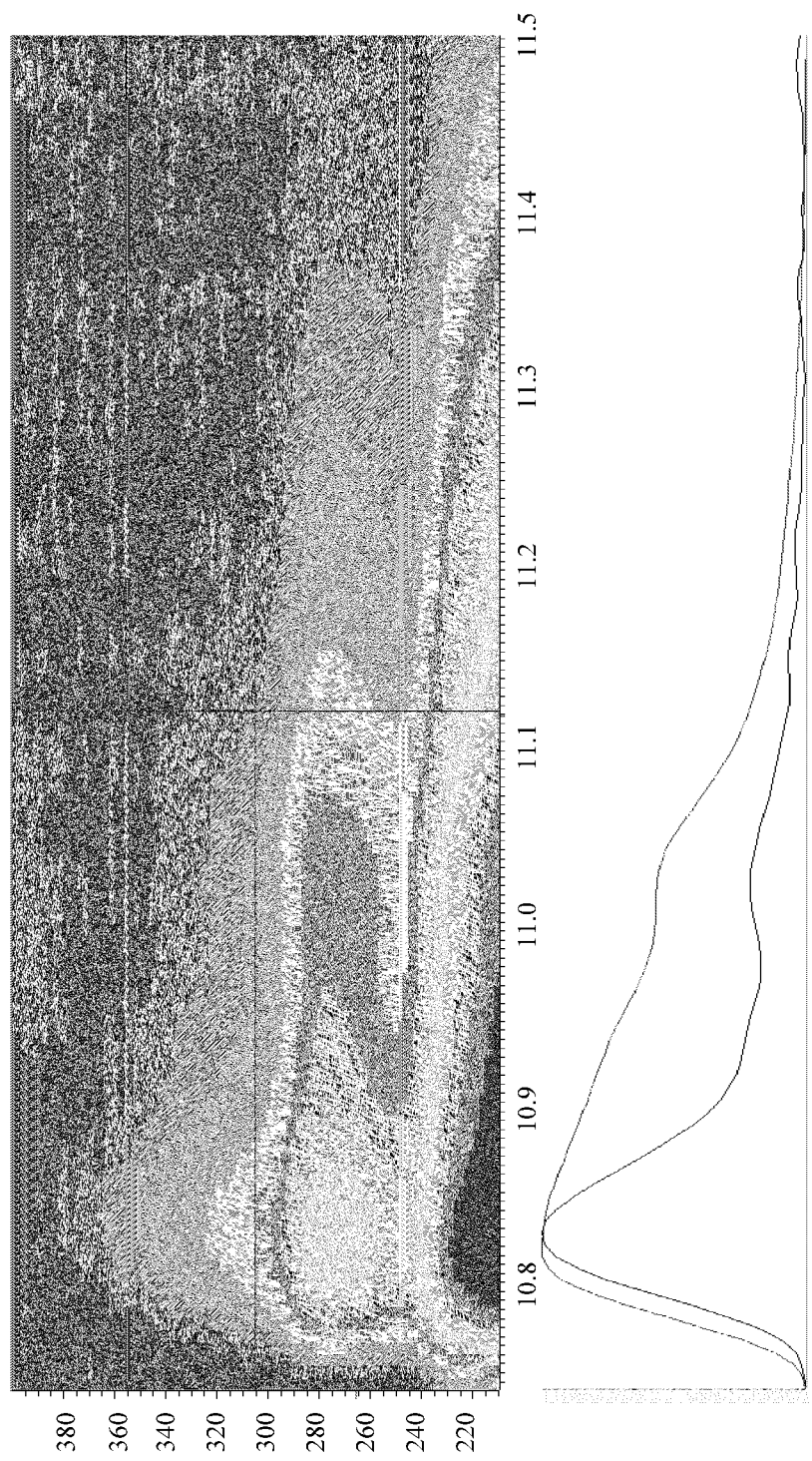
FIG. 25B shows a UV image of CA 19-9 analyzed by HPLC following exposure to saliva according to at least one embodiment of the present disclosure.
Figure 26A:
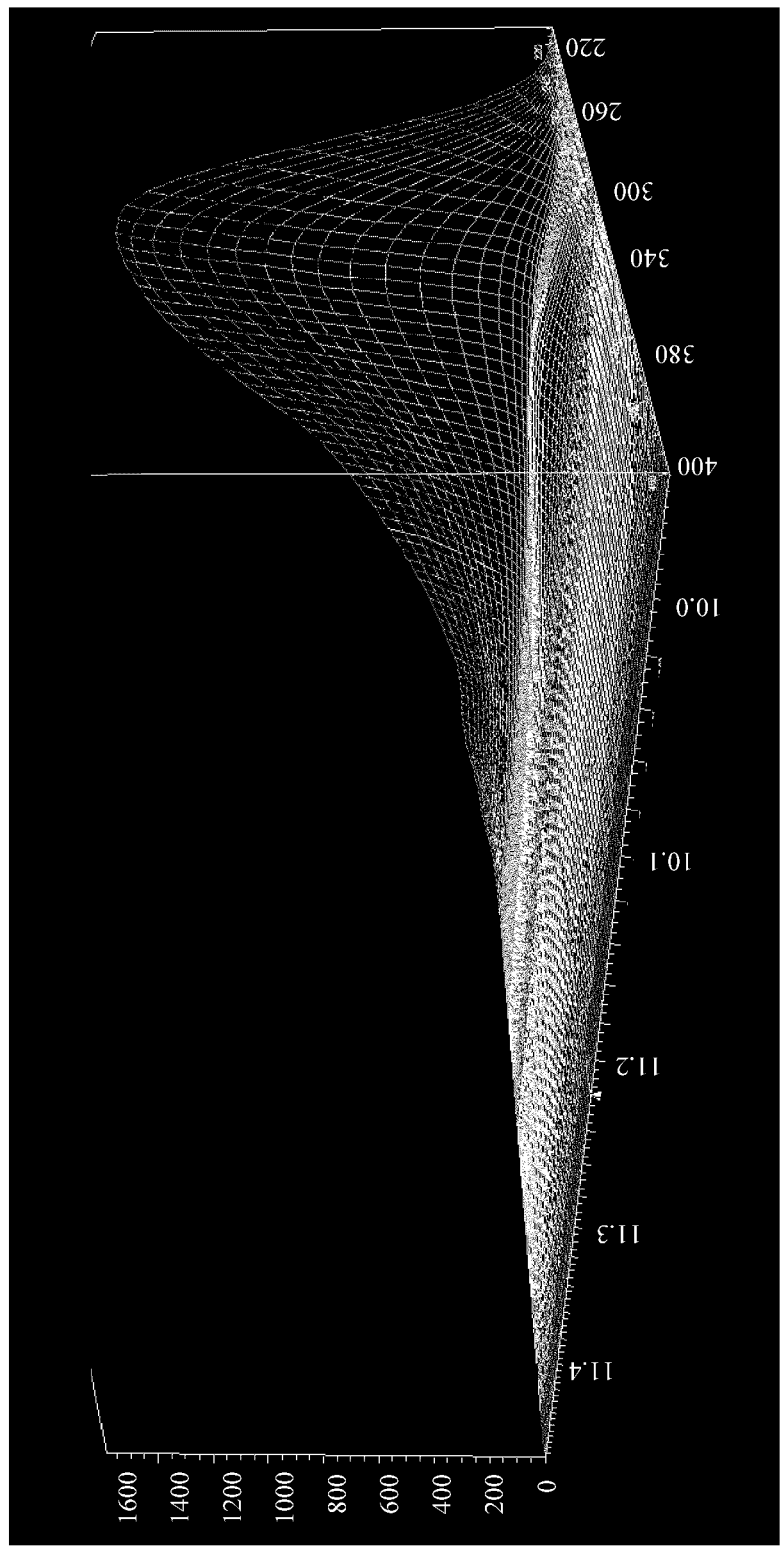
FIG. 26A shows a three dimensional plot of CA 19-9 analyzed by HPLC following exposure to saliva and a stabilizing mixture according to at least one embodiment of the present disclosure.
Figure 26B:
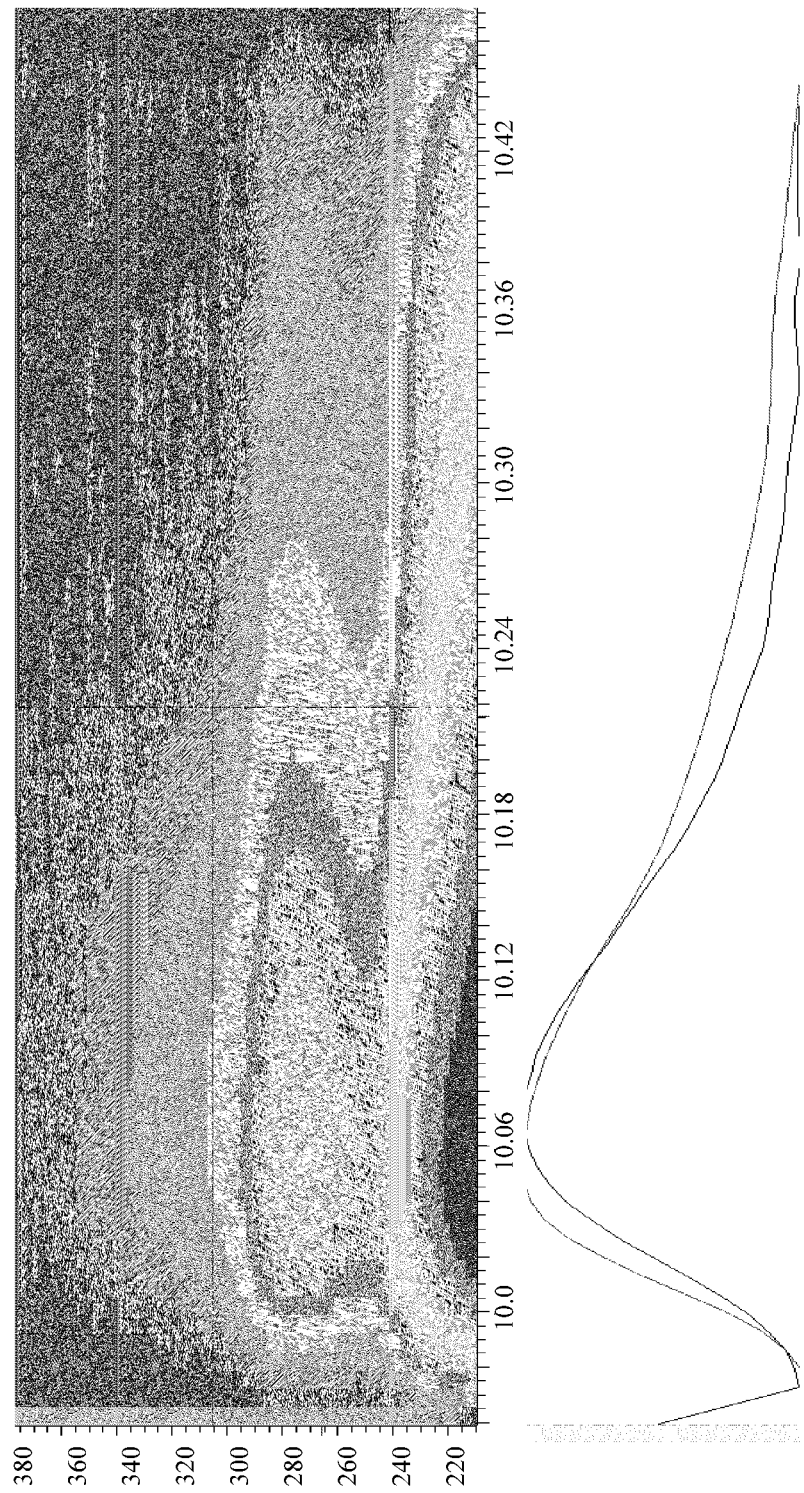
FIG. 26B shows a UV image of CA 19-9 analyzed by HPLC following exposure to saliva and a stabilizing mixture according to at least one embodiment of the present disclosure.
Figure 27A:
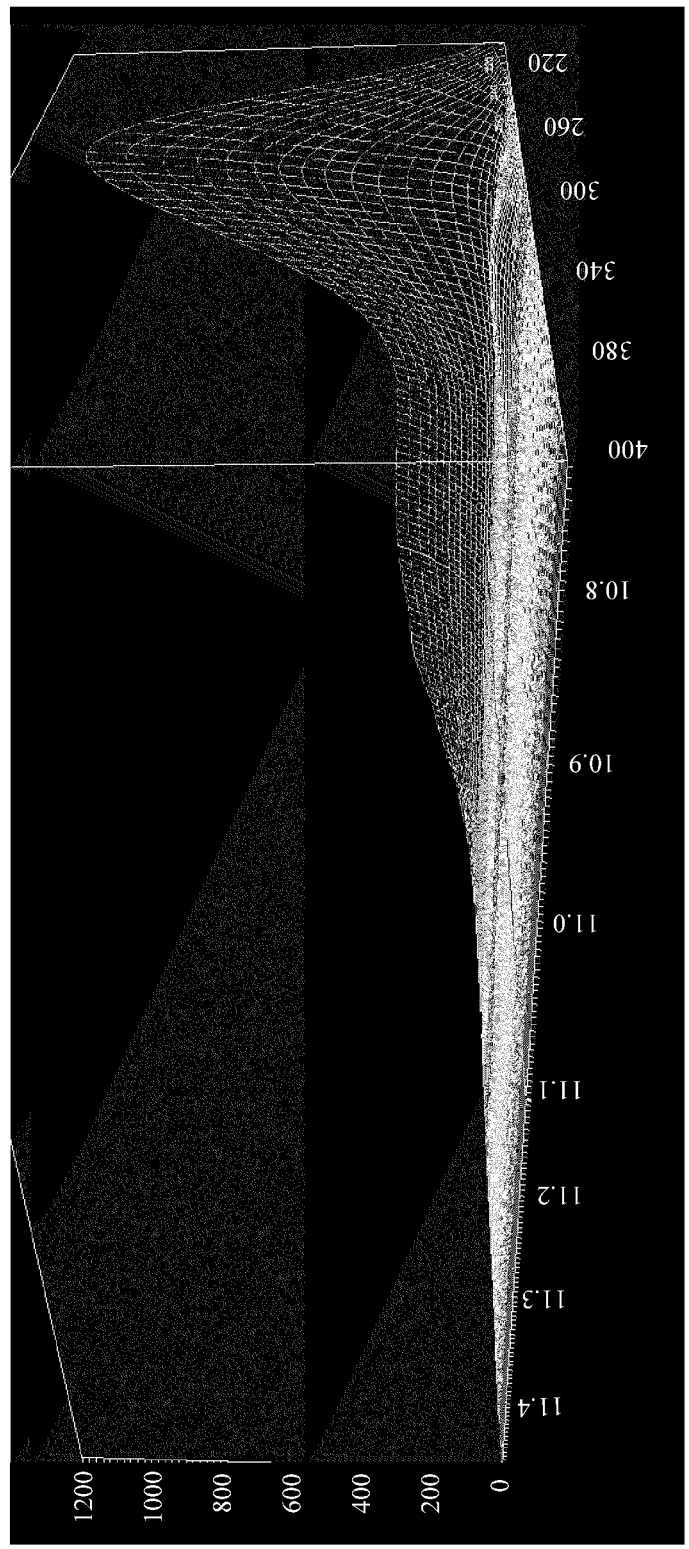
FIG. 27 shows a comparison of three dimensional plots from HPLC analyzed CA 19-9 (FIG. 27A), CA 19-9+Saliva (FIG. 27B), and CA 19-9+Saliva+Stabilizing mixture (FIG. 27C) according to at least one embodiment of the present disclosure.
Figure 27B:
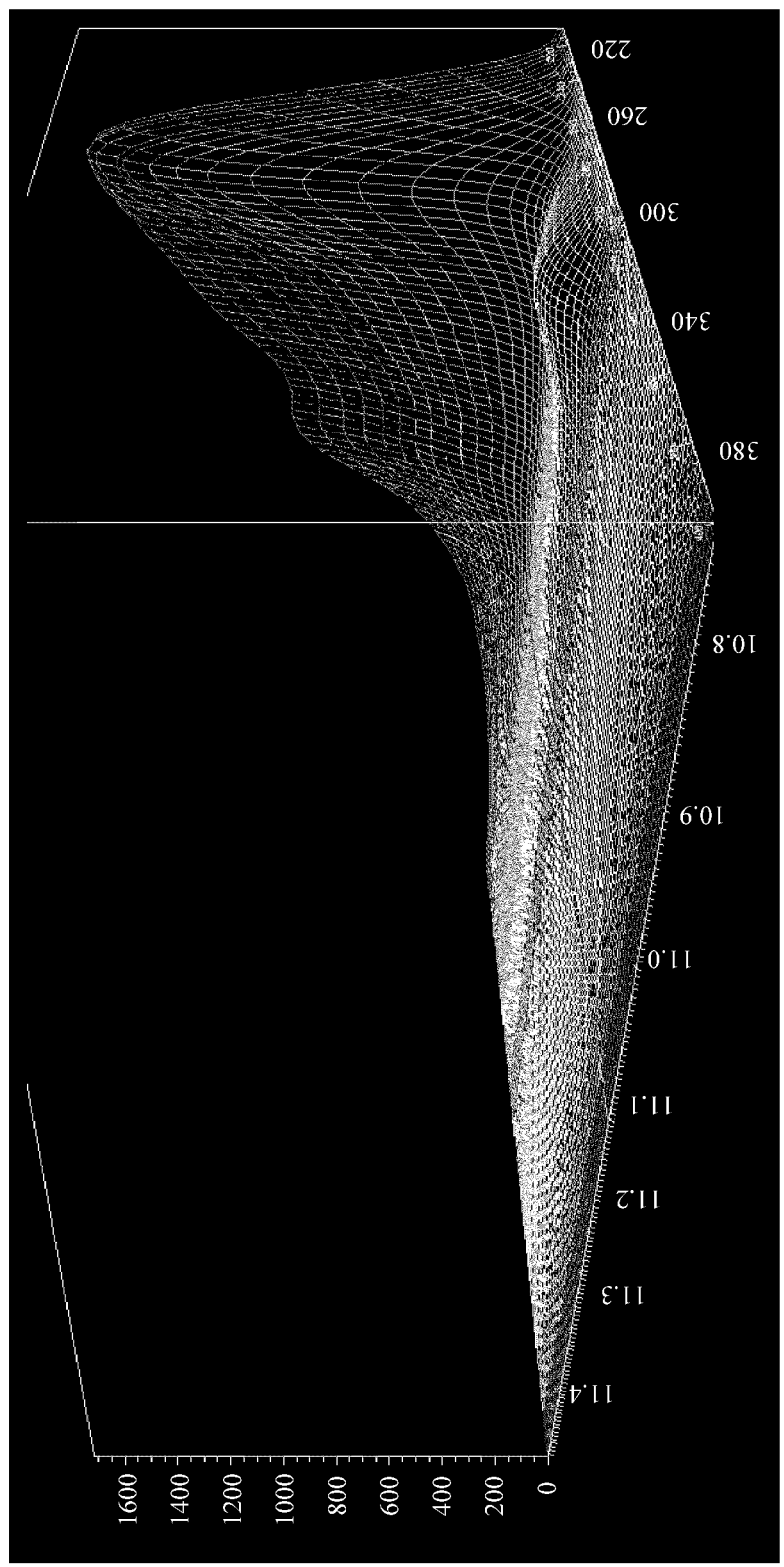
Figure 27C:
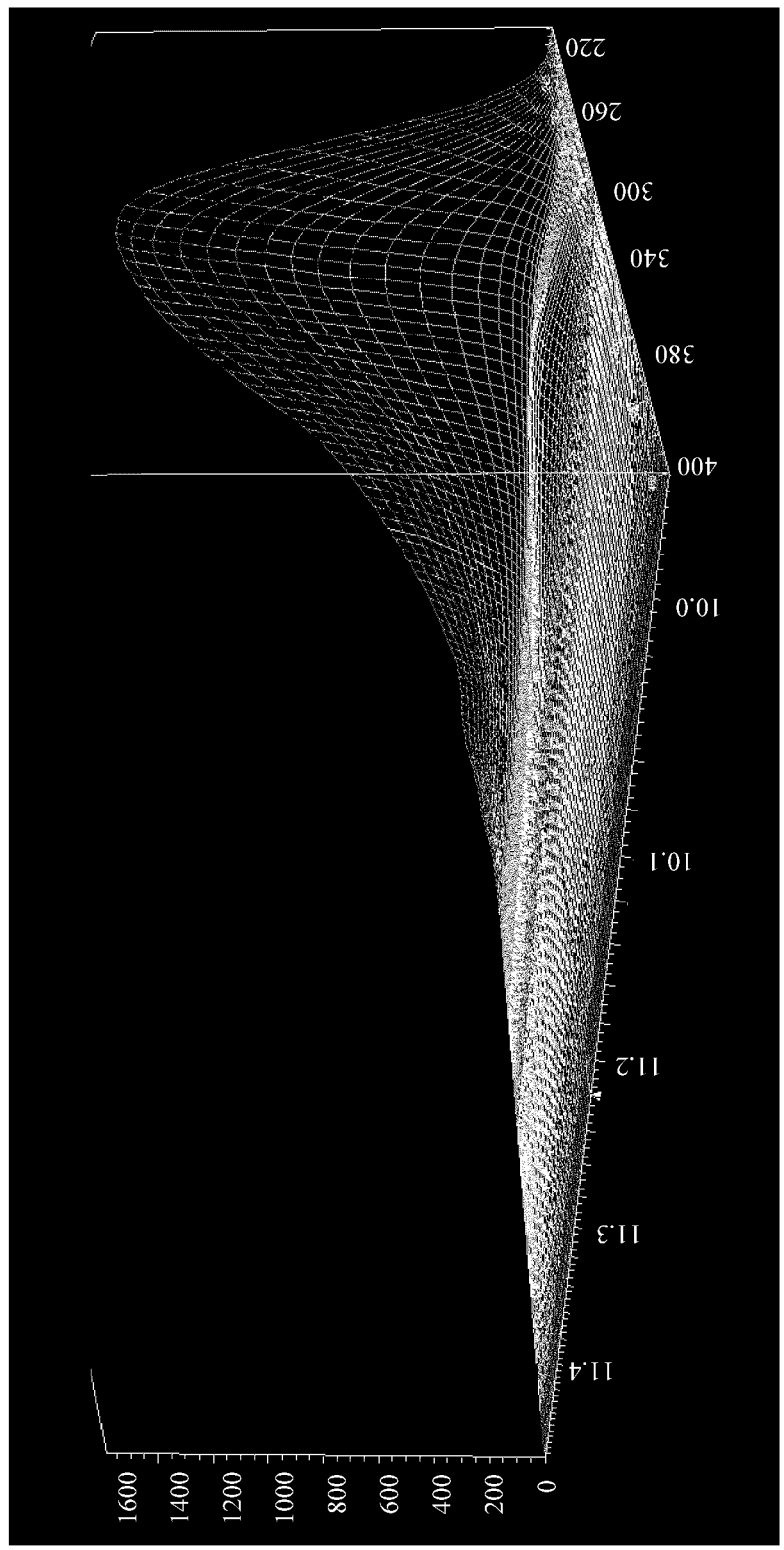
Figure 28B:
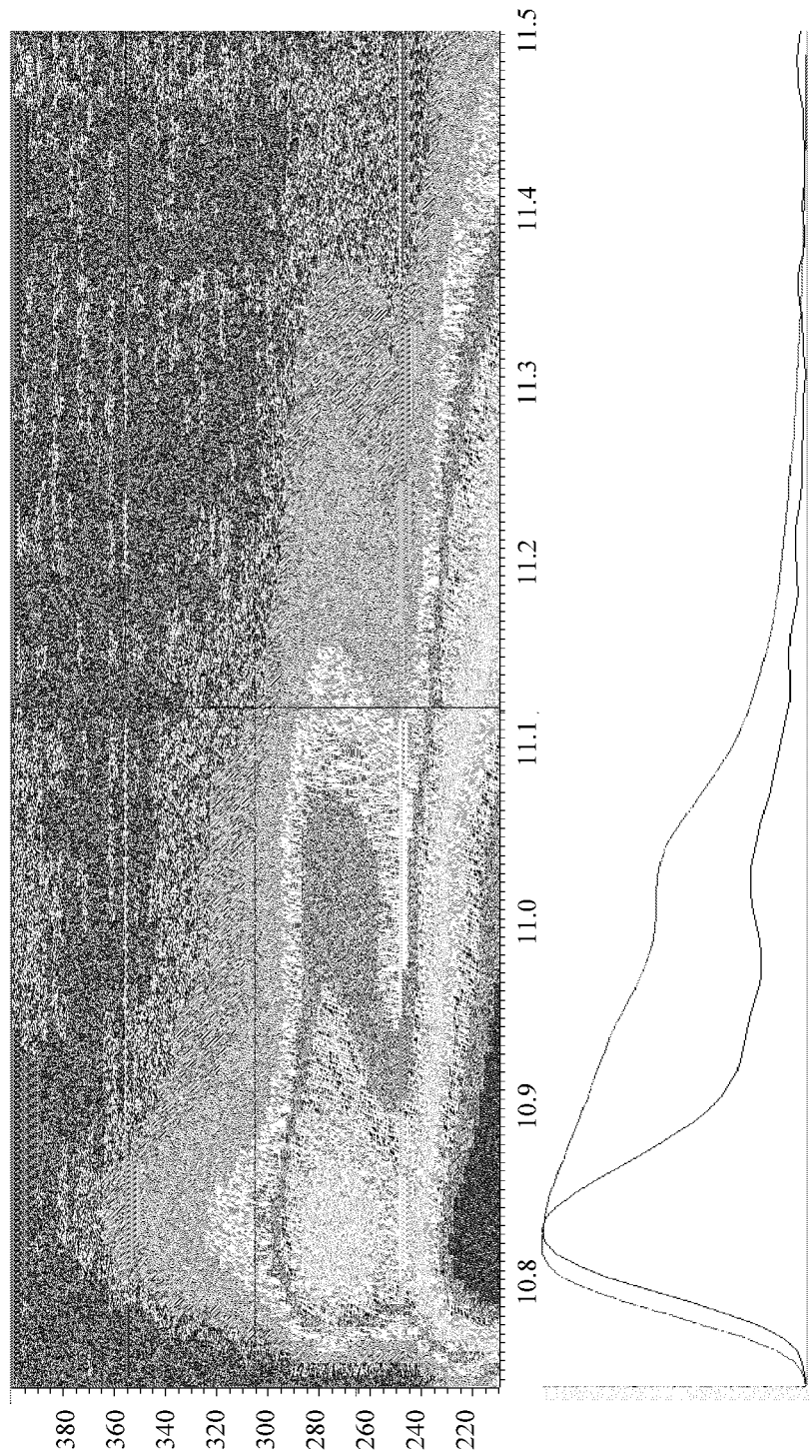
FIG. 28 shows a comparison of UV images from HPLC analyzed CA 19-9 (FIG. 28A), CA 19-9+Saliva (FIG. 28B), and CA 19-9+Saliva+Stabilizing mixture (FIG. 28C) according to at least one embodiment of the present disclosure.
Figure 28C:
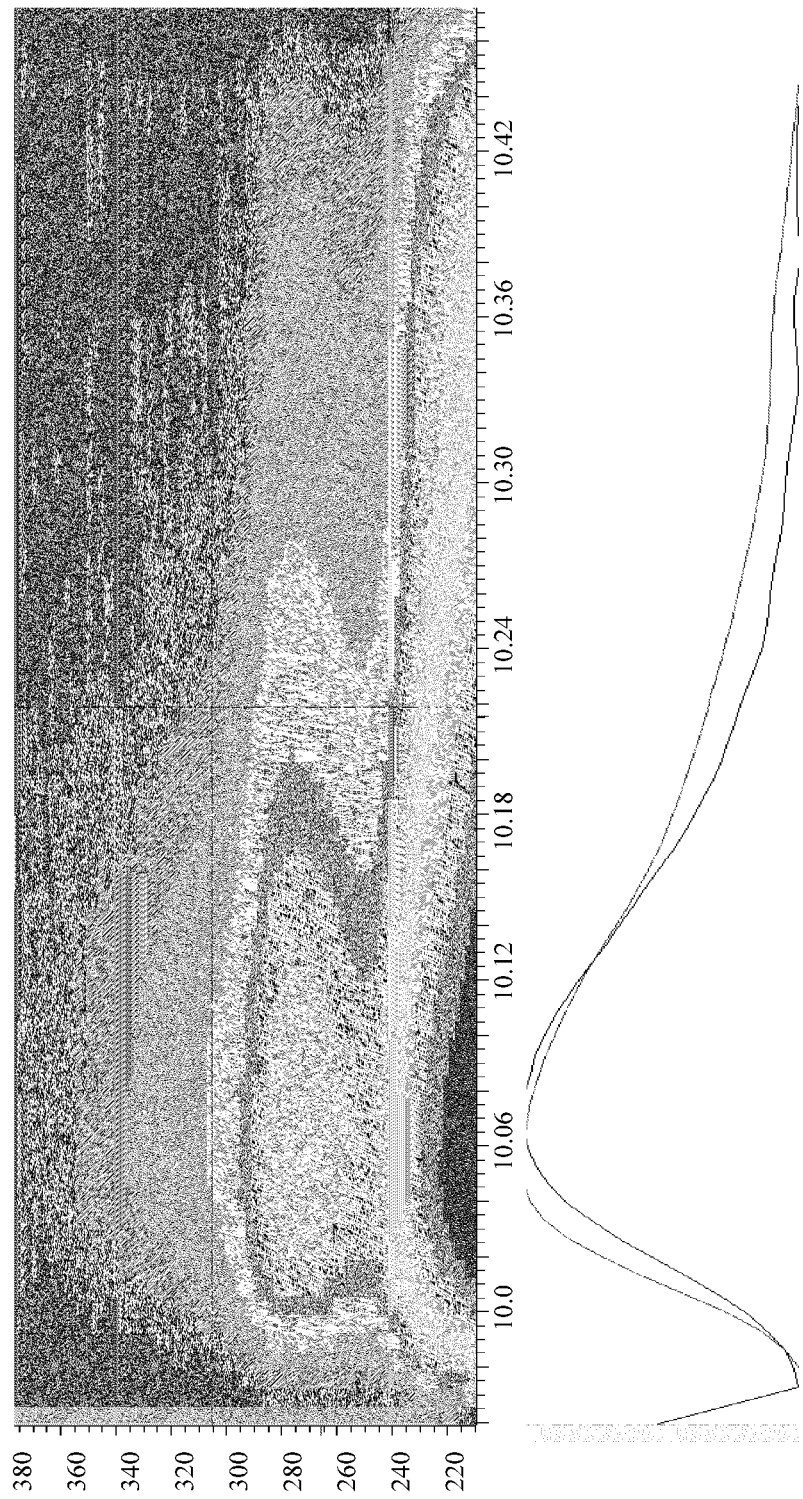
Figure 29:
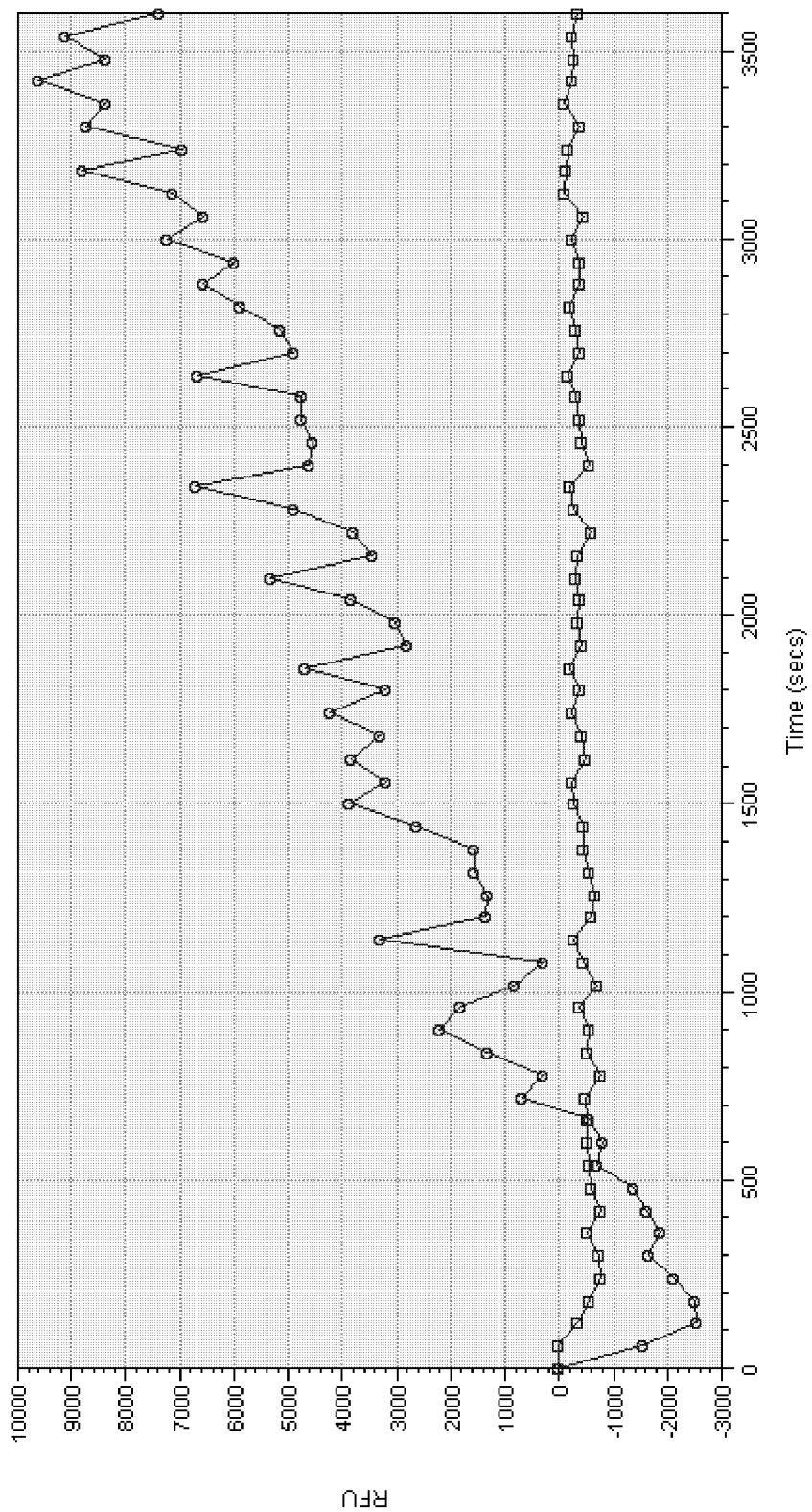
FIG. 29 shows a graphical depiction of Peroxidase activity inhibition by an inhibitor cocktail according to at least one embodiment of the present disclosure.
Figure 30:
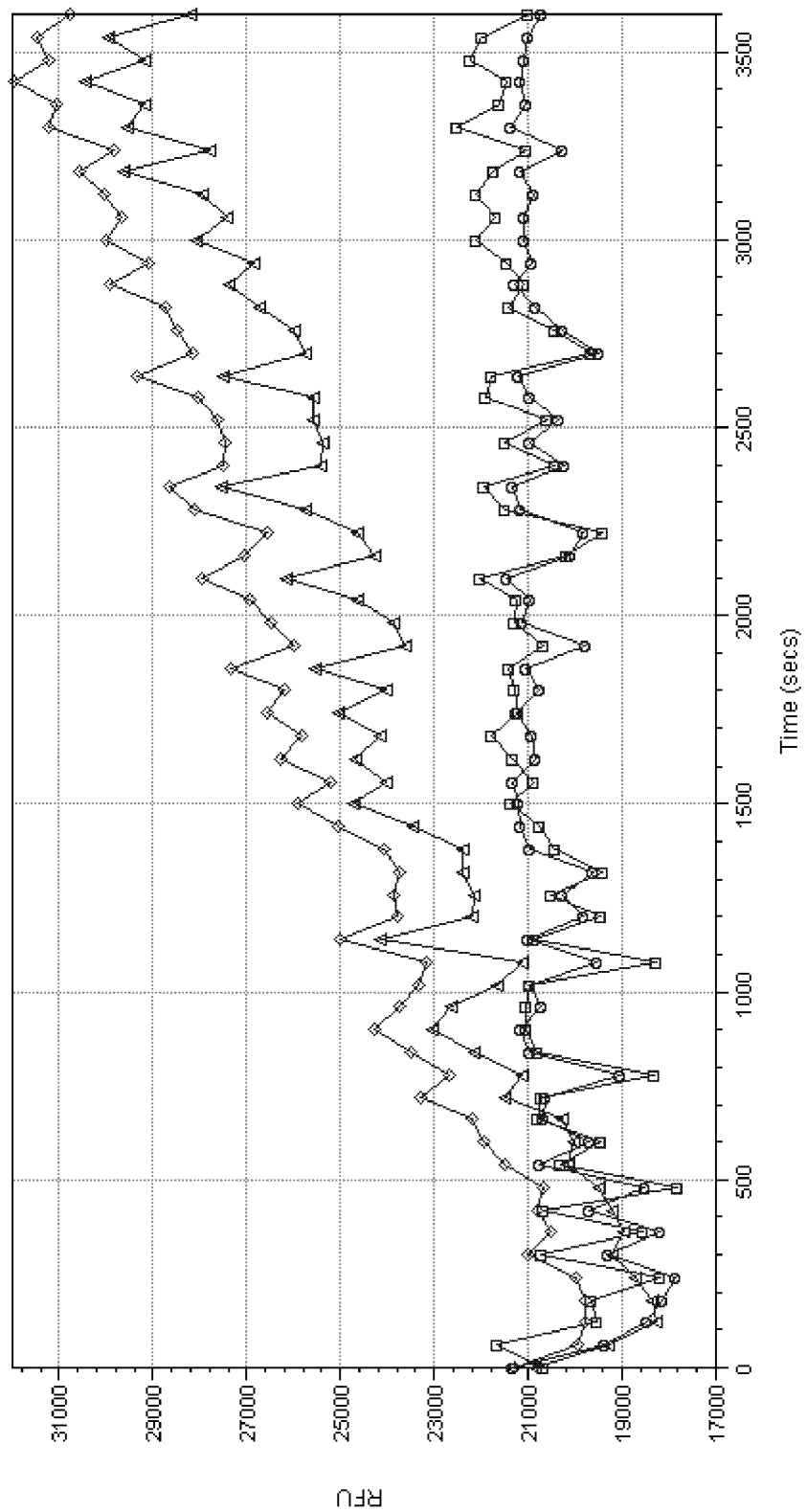
FIG. 30 shows a graphical depiction of Peroxidase activity inhibition by caffeine according to at least one embodiment of the present disclosure.
Figure 31:
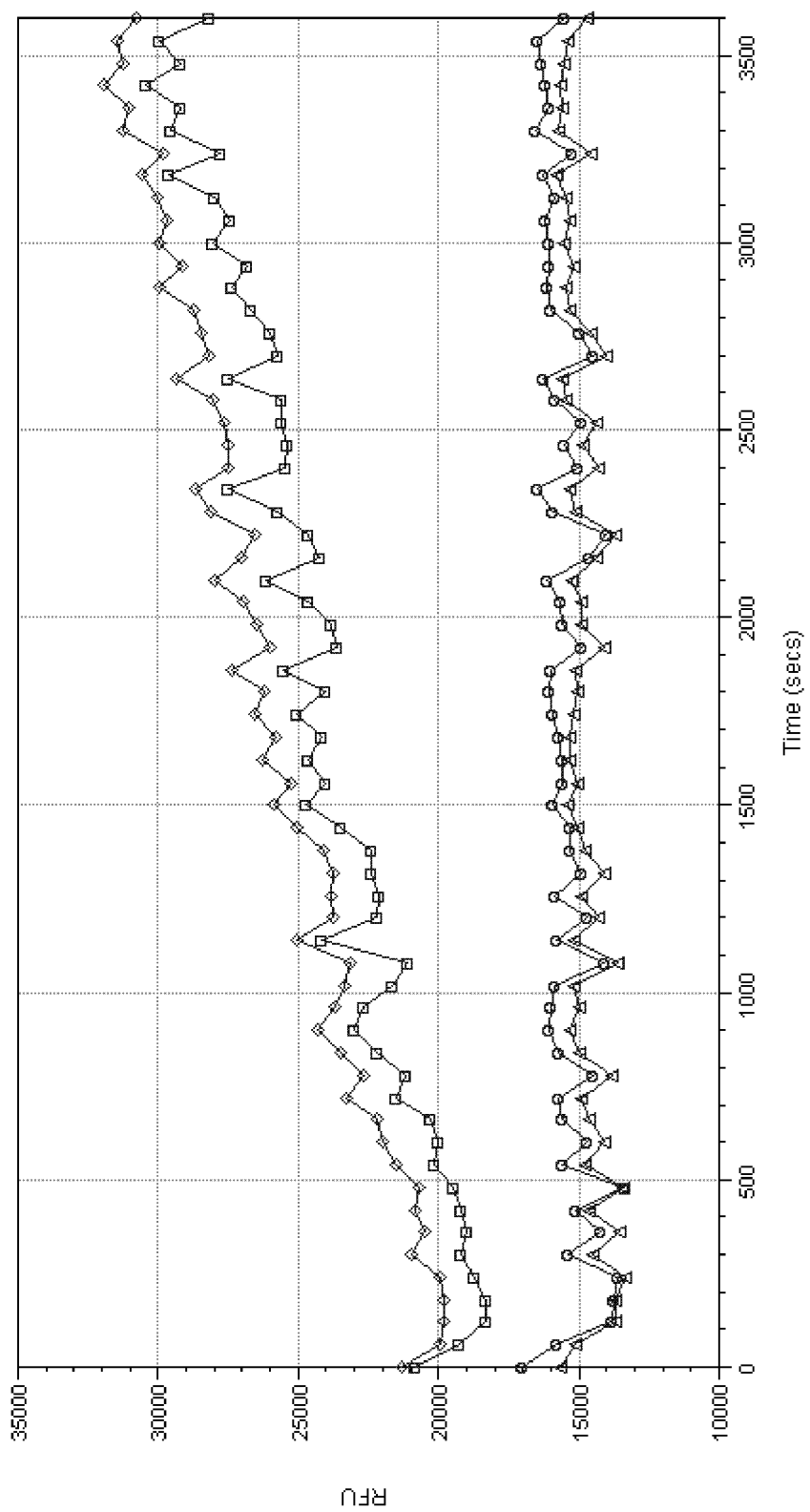
FIG. 31 shows a graphical depiction of Peroxidase activity inhibition by 3-tert-butyl-hydroxyanisole according to at least one embodiment of the present disclosure.
Figure 32:
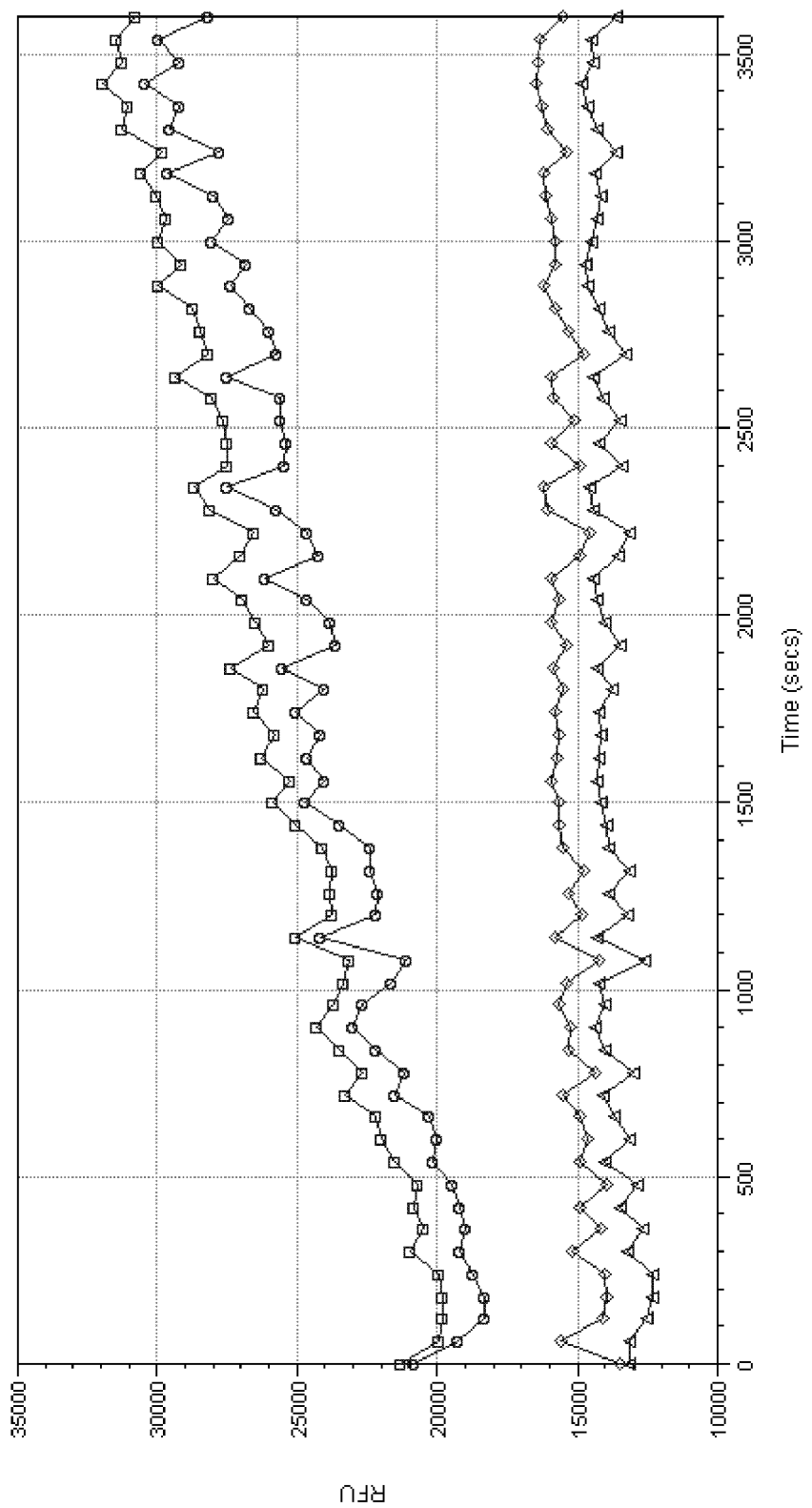
FIG. 32 shows a graphical depiction of Peroxidase activity inhibition by benzoic acid according to at least one embodiment of the present disclosure.
Figure 33:
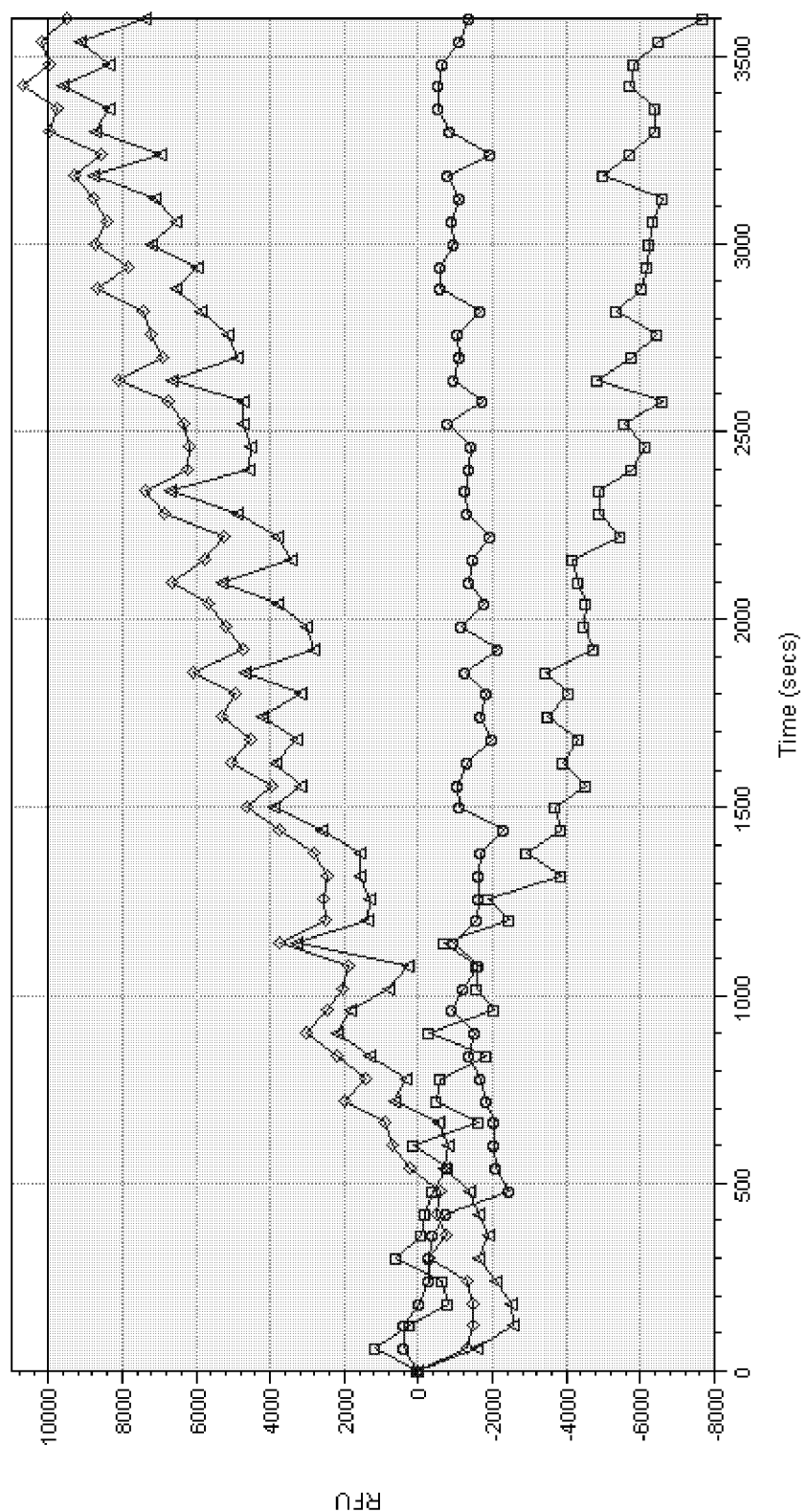
FIG. 33 shows a graphical depiction of Peroxidase activity inhibition by aluminum potassium sulfate dodecahydrate according to at least one embodiment of the present disclosure.

At least one procedure used for the stabilization and detection of Cancer Antigen 19-9 (CA 19-9) as described herein, includes the incubation of CA 19-9 with a stabilizing agent prior to, or concurrently with, detection. Analysis of samples was conducted on a HPLC 1100 series (Agilent Technologies) with a 2.1×150 (3.5μ) C18 reverse phase column. The mobile phase used was acetonitrile with 6.5 mM Ammonium Carbonate. A CA 19-9 standard was prepared by dissolving CA 19-9 with 1.0 ml of deionized water. The samples analyzed by HPLC included pure CA 19-9 (FIG. 24), 100 ml CA 19-9 mixed with 100 ml of fresh saliva (FIG. 25), and 200 ml CA 19-9 mixed with 100 ml of fresh saliva and 100 ml of a stabilizing compound comprising aluminum sulfate hydrate, benzoic acid, and aluminum potassium sulfate dodecahydrate (each present in a 1:1:1 ratio) (FIG. 26). While the pure CA 19-9 sample was analyzed fresh, samples of CA 19-9 with saliva were incubated overnight at room temperature prior to analysis. For each sample analyzed, the data was displayed through a three dimensional plot (FIGS. 24A, 25A, and 26A) and a UV image (FIGS. 24B, 25B, and 26B). Additionally, a comparison of the analysis CA 19-9 in the presence of saliva with and without stabilizing agent is shown in FIGS. 27 (three dimensional plot) and 28 (UV image).

10. CA 19-9 Protection Assays

A series of GRAS compounds were tested, as shown in FIGS. 24-26, for the ability to protect CA 19-9 from degradation by components in saliva. The tested compounds are included in Table I. As described above, a stabilizing compound comprising aluminum sulfate hydrate, benzoic acid, and aluminum potassium sulfate dodecahydrate (each present in a 1:1:1 ratio) minimized the degradation of CA 19-9 in at least one embodiment.

11. Peroxidase Assay

To determine the effect of various GRAS compounds as inhibitors of peroxidase activity, a standard assay using Amplex® Red (Life Technologies), which releases a fluorescent oxidation product. This oxidation product, named resorufin, has an excitation and emission maxima of approximately 571 nm and 585 nm, respectively, and because the extinction coefficient is high (58,000±5,000 cm-1M-1), it allows for the use with fluorometric or spectrophotometric assays.

The test compounds, such as GRAS materials or cocktails of same, were prepared at a concentration of 500 ppm in distilled water. For the assay, 50 μl samples of test compounds were mixed with 20-30 μl of saliva (either "pooled" or "unpooled") prior to the addition of Amplex® Red. Following the mixture of the test compounds with saliva, 50 μl of Amplex® Red/HRP working solution (See Protocol for Invitrogen Assay #A22188, which is incorporated herein in its entirety), which has a concentration of 100 μM of Amplex® Red, is added to the test compound/saliva mixture. Following the initiation of the reaction, each mixture is measured at 1 minute intervals using a spectrophotmeter (such as a Molecular Devices M5 reader) for excitation in the range of 530-560 nm and fluorescence emission detection at approximately 590 nl, or for absorption at approximately 560 nm. Reactions were allowed to run for 30 minutes during these assays.

12. Peroxidase Protection Assays

A series of GRAS compounds and cocktails of GRAS compounds were tested, as shown in FIGS. 29-33, for the ability to inhibit degradation of a peroxidase-sensitive marker by components in saliva. Various embodiments of the tested compounds are included in Table I. As described above, a stabilizing compound/cocktail comprising aluminum sulfate hydrate, benzoic acid, and aluminum potassium sulfate dodecahydrate (each present in a 1:1:1 ratio) minimized the degradation of a peroxidase sensitive marker in at least one embodiment (FIG. 29, open circle=blank control, open square=stabilizing cocktail). Further, inhibition assays were also conducted with caffeine (FIG. 30, CDI #33; Key: open circle=pooled saliva, open square=unpooled saliva, open triangle=caffeine, open triangle=caffeine (repeat)), 3-tert-butyl-hydroxyanisole (FIG. 31, CDI #39; Key: open circle=pooled saliva, open square=unpooled saliva, open triangle=3-tert-butyl-hydroxyanisole, open triangle=3-tert-butyl-hydroxyanisole (repeat)), benzoic acid (FIG. 32, CDI #16; Key: open circle=pooled saliva, open square=unpooled saliva, open triangle=benzoic acid, open triangle=benzoic acid (repeat)), and aluminum potassium sulfate dodecahydrate (FIG. 33, CDI #42; Key: open circle=pooled saliva, open square=unpooled saliva, open triangle=aluminum potassium sulfate dodecahydrate, open triangle=aluminum potassium sulfate dodecahydrate (repeat)), each of which showed significant peroxidase inhibition capabilities.

13. Diagnostic Devices

Figure 34:
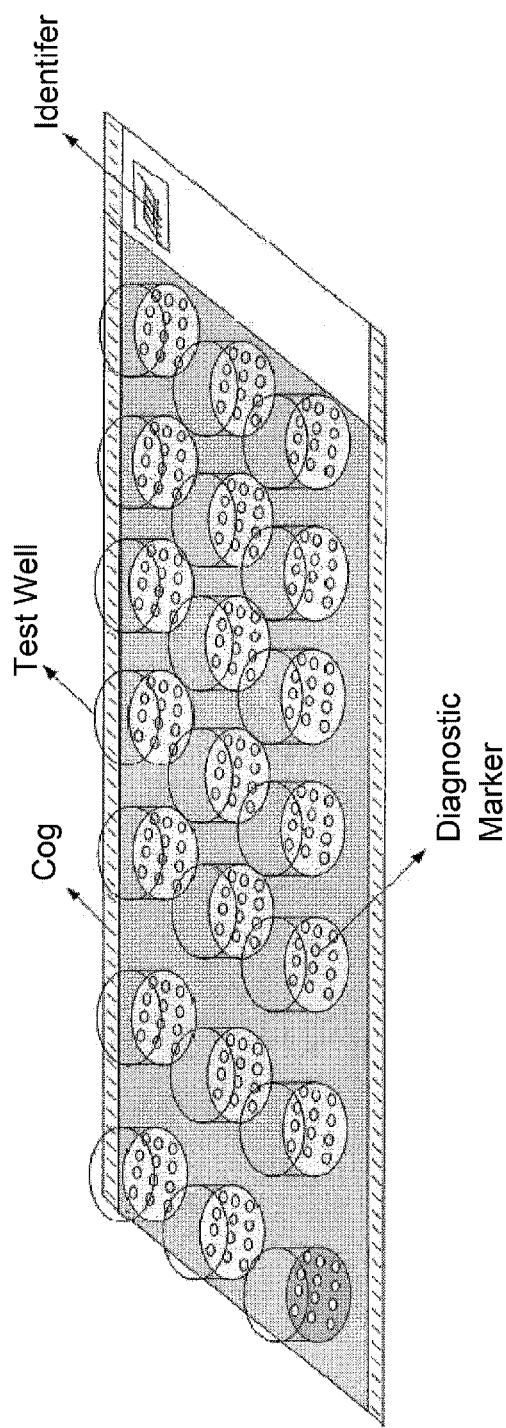
FIG. 34 shows a schematic of a diagnostic system, according to at least one embodiment of the present disclosure.

In an example of a diagnostic device, as shown in FIG. 34, a test slide with 28 test wells are spotted with 12 to 18 sets of diagnostic markers. These reagents may include diagnostic markers, or controls for the diagnosis. The diagnostic device, in this example, has four diagnostic markers spotted in duplicate, along with two positive and two negative control marker. Each marker is spotted with a competitor, such as anti-haptin, which binds the capture antigen particle to the marker. The device may have four different hatpin/anti-haptin systems to serve as the generic capture system. A unique haptin may be conjugated to a fully paramagnetic particle (PmMp). The PmMp is also coated with a capture monoclonal antibody (MAb) specific for the marker. A second particle (polystyrene microparticle with Europium) is conjugated with the second or detection MAb. In the diagnostic device shown in FIG. 34, the hash marks on the side of the diagnostic device (slide) are indentations molded into the plastic, which may be used as cog grooves. Additionally the slide is designed to fit into a processor that may have more than one processing station, as shown in FIG. 36.

Figure 36:
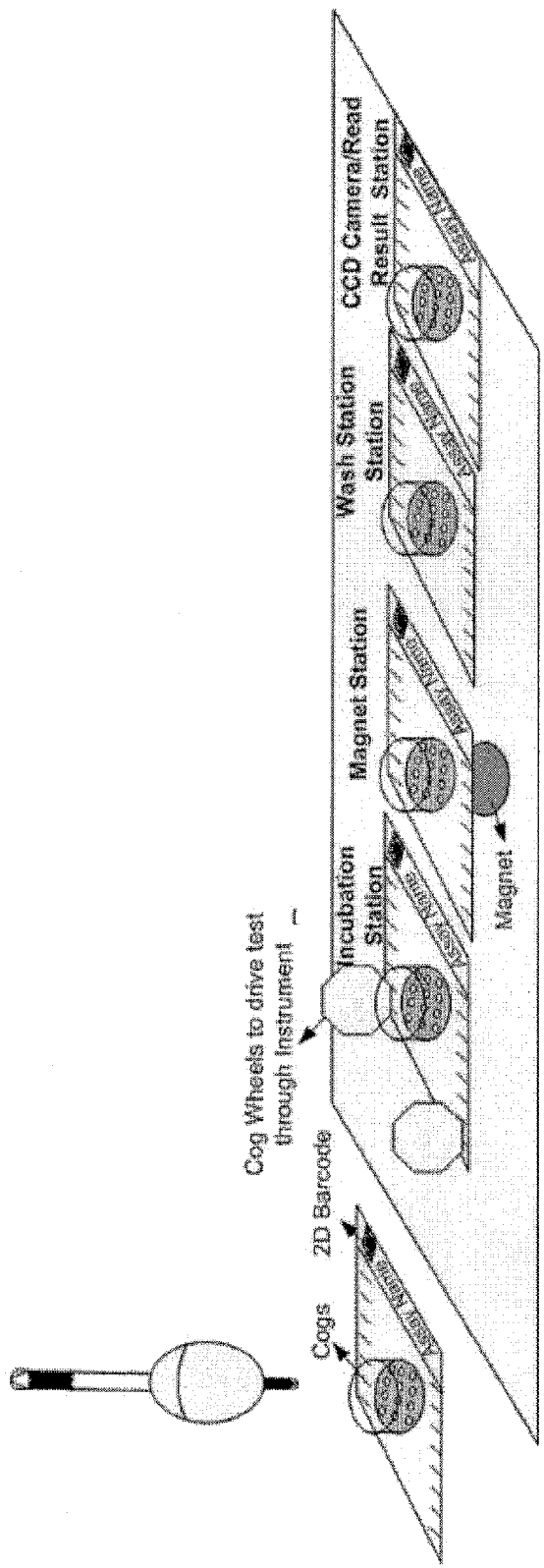
FIG. 36 shows a graphical depiction of a fluid collection device, according to at least one embodiment of the present disclosure.

In performing a method of detecting a diagnostic marker using an embodiment of the diagnostic device, such as that in FIGS. 34 and 36, the user adds a pre-determined amount of specimen (such as 120 µl) to a specimen diluent (such as 40 to 120 µl), and adds the mixture to each test well. Following addition of the diluted specimen, the test slide is incubated at 37° C. for about 5 to about 15 minutes with agitation. Following the incubation period, the test wells move over a magnetic source that brings the PmMp to the bottom of the well, so that there is maximal binding of the PmMp with the anti-haptin bound in the test well. Next, specimen and assay reagents are removed, wash buffer is added and aspirated off. Lastly, each well is scanned using a visualization device, such as a CCD camera, and then the fluroescent signal (or other signal) of each marker is determined.

14. Fluid Collection Device.

Figure 35:
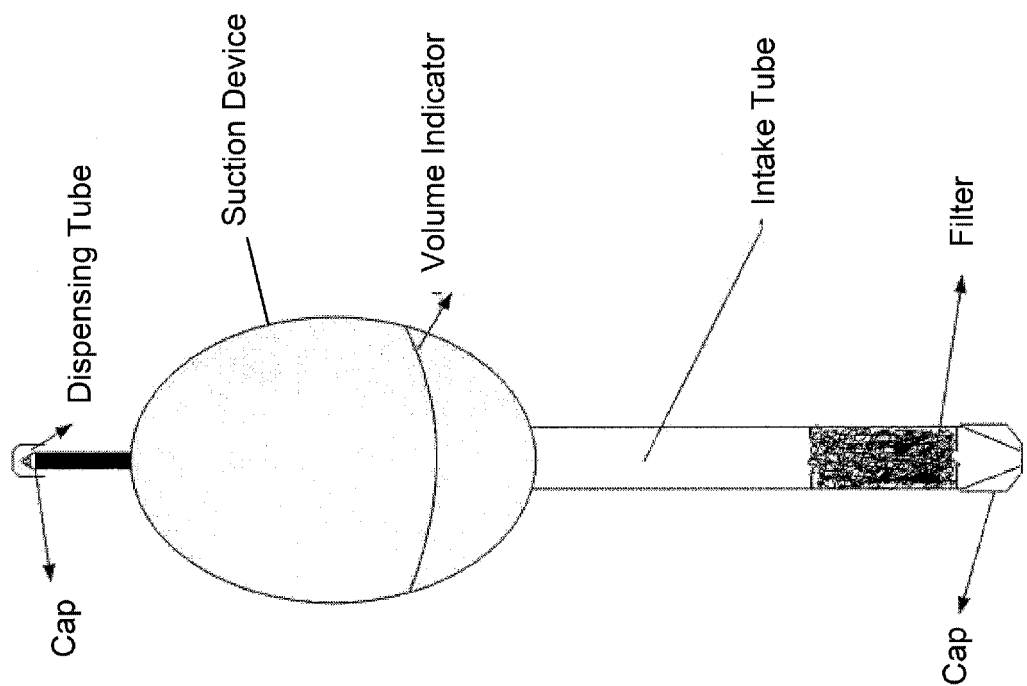
FIG. 35 shows a graphical representation of an assay component, according to at least one embodiment of the present disclosure.

An example of a collection device for the collection of an bodily fluids is depicted in FIG. 35. In this example, the collection device is capable of collecting at least 500 µl of bodily fluid, such as saliva. The cap is first removed from the tube. Squeezing the bulb provides suction adequate to pull an amount of saliva into the bulb. In some cases, a filter may be included in the tube to remove unwanted materials (such as particulate and mucous). The filter may be of any known filter material, such as rayon, that is appropriate for the purposes described herein. Following the obtaining of the bodily fluid in the collection device, a cap is placed on the tube, and a second cap is removed from a dispensing tube. The dispensing tube is in fluid communication with the bulb and is sized and shaped to allow for drops of a predetermined size to be formed when the bulb is squeezed. For example, the dispensing tube may allow drops of 30 µl to be formed when the bulb is squeezed.

While various embodiments of the systems, methods, and compositions of the present disclosure have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for screening biomarkers in bodily fluids in the presence of stabilization agents, comprising a detection platform, comprising:
   a plurality of detection sites each capable of receiving a disease state diagnostic biomarker, comprising a biological molecule indicative of a disease state, one or more of a plurality of stabilization agents, wherein the one or more of the stabilizing agents is comprising citric acid sodium hydroxide (Fixanal® Buffer 6.0 (Sigma-Aldrich Co.)), acetic acid, aluminum hydroxide bentonite, aluminum sulfate hydrate, aluminum potassium sulfate dodecahydrate, benzoic acid, caffeine, and 3-tert-butyl-hydroxvanisole, or a combination thereof; and an indicator labeled detection agent;
   a detection device capable of determining a binding characteristic between the indicator labeled detection agent and the disease state diagnostic biomarker in the detection sites;
   a computer database capable of receiving a plurality of binding characteristics, the plurality of binding characteristics comprising at least one binding property of a diagnostic biomarker molecule to said indicator labeled detection agent;
   a processor operably coupled to the computer database and the detection device, the processor having been programmed to:
      determine the binding characteristic of the indicator labeled detection agent to the disease state diagnostic biomarker in each of the plurality of detection sites;
      compare the binding characteristic among each of the plurality of detection sites to order the level of effect of the one or more from a plurality of stabilizing agents assayed on the binding characteristic between the indicator labeled detection agent and the disease state diagnostic agent;
      generate a binding report using the compared binding characteristics; and
      select the most effective one of said plurality of stabilizing agents at an amount or concentration sufficient to completely or substantially prevent or reduce degradation or inactivation of the disease state biomarker.

2. The system of claim 1, wherein the one or more stabilizing agent is selected from the group consisting of a protease inhibitor, a DNase inhibitor, and a RNase inhibitor.

3. The system of claim 1, wherein the one or more stabilizing agent prevents the degradation or inactivation of the disease state diagnostic biomarker for at least a twenty four hour period following interaction with said diagnostic agent.

4. The system of claim 1, wherein the disease state diagnostic biomarker is selected from the group consisting of a protein, a glycoprotein, a nucleic acid, an enzyme, an enzyme inhibitor, and a metabolite.

5. The system of claim 1, wherein one or more of the plurality of stabilizing agents is present in an amount or concentration sufficient to completely or substantially inactivate or reduce the activity of, an enzyme selected from the group consisting of an amylase, a lysozyme, a peroxidase, a glycosidase, an esterase, a protease, and a peptidase.

6. The system of claim 1, wherein the plurality of stabilizing agents are each present in approximately the same concentration.

7. The system of claim 1, wherein the one or more of the plurality of stabilizing agents is capable of inhibiting degradation of the diagnostic marker to an inhibitory degree, wherein the inhibitory degree is selected from the group consisting of at least about 40%, at least about 45%, at least about 50%, at least about 55%, at least about 60%, at least about 65%, at least about 70%, at least about 75%, at least about 80%, at least about 85%, at least about 90%, at least about 95%, and at least about 99%.

8. The system of claim 1, wherein the one or more of the plurality of stabilizing agents has a concentration selected from the group consisting of about 200 parts per million (ppm) to about 2000 ppm, about 400 ppm to about 1600 ppm, about 600 ppm to about 1400 ppm, about 800 ppm to about 1200 ppm, and about 400 ppm to about 600 ppm.

9. The system of claim 1, wherein one or more of the plurality of stabilizing agents is present in an amount or concentration sufficient able to inhibit or reduce the degradation or inactivation of the diagnostic marker for an inhibitory period selected from the group consisting of at least one minute, at least about five minutes, at least about ten minutes, at least about fifteen minutes, at least about thirty minutes, at least about one hour, at least about two hours, at least about four hours, and at least about eight hours.

10. The system of claim 1, wherein the disease state diagnostic biomarker is selected from the group consisting of Aldose reductase, Angiogenin, Annexin A1, B-cell activating factor (BAFF), B-cell lymphoma 2 (BCL2)-like 2, Beta Human chorionic gonadotropin, Ca15-3, Calcyclin, Calvasculin, Cancer Antigen CA 19-9, Cancer Antigen CA 15-3, Cathepsin D, Caveolin-1, Chromogranin A, Alpha-crystallin B chain (CRYAB), Endostatin, Eotaxin-2, Epithelial cell adhesion molecule (EpCAM), Ezrin, fatty acid binding protein 4 (FABP4), Galectin-3, y-glutamylcysteine ligase regulatory chain (GCLR), Gelsolin, Glucose 6-phosphate (G6P), Glycoprotein 130 (gp130), Glutathione S-transferase Mu 1 (GSTM1), Hepsin, High-mobility group protein B1 (HMGB-1), Insulin-like growth factor binding protein 1 (IGFBP-1), Insulin-like growth factor binding protein 4 (IGFBP-4), Insulin-like growth factor binding protein 5 (MI-BP-5), Insulin-like growth factor binding protein 6 (IGFBP-6), LGL, latency associated peptide (LAP), macrophage stimulating protein (MSP), MHC class I polypeptide-related sequence A (MICA), Nucleoside diphosphate kinase B (NME2), Neuron-specific Enolase (NSE), Osteopontin, Osteoprotegerin, Pepsinogen, Peroxiraloxin, Phosphoserine aminotransferase (PSAT1), Prostate Specific Antigen, Receptor tyrosine-protein kinase (EibB3), Serpin B3, Vascular smooth muscle cell growth factor R2 (VSGF R2/KDR), Vascular endothelial growth factor R3 (VEGF R3/Flt-4), Thyroglobulin, Tyrosine kinase with immunoglobulin-like and EGF-like domains 2 (TIE-2), Tissue plasminogen activator (tPA), Transforming growth factor beta (TGF-.beta.1), Tumor necrosis factor receptor 1 (TNF-R1), urokinase-type Plasminogen Activator (uPA), urokinase-type Plasminogen Activator Receptor (uPAR), Brca1, Brca11, kallikreins, e-cadherin, Hox peptide, and Engrailed-2.

11. The system of claim 1, wherein the disease state comprises: a bacterial or a mammalian infection by a bacterial species; a viral or a mammalian infection by a viral species; a fungal or a mammalian infection by a fungal species; a parasite or a mammalian infection by a parasitic species; a diabetic condition; a cardiovascular disease; or a cancerous or precancerous condition.

12. The system of claim 1, wherein said bodily fluids or fractions thereof, comprise saliva, mucous secretions, tears, sweat, bile, semen, urine, vaginal secretions, exhalations, anal secretions, blood, plasma, serum, lymph, or mixtures thereof.

* * * * *